(12) United States Patent
Kehrel et al.

(10) Patent No.: US 9,316,650 B2
(45) Date of Patent: Apr. 19, 2016

(54) DETECTION AND REMOVAL OF MISFOLDED PROTEINS/PEPTIDES

(75) Inventors: Beate Kehrel, Rheine (DE); Martin Brodde, Havixbeck (DE)

(73) Assignee: OXPROTECT GMBH, Muenster (DE)

( * ) Notice: Subject to any disclaimer, the term of this patent is extended or adjusted under 35 U.S.C. 154(b) by 0 days.

(21) Appl. No.: 13/984,850

(22) PCT Filed: Feb. 10, 2012

(86) PCT No.: PCT/EP2012/052330
§ 371 (c)(1),
(2), (4) Date: Aug. 10, 2013

(87) PCT Pub. No.: WO2012/107567
PCT Pub. Date: Aug. 16, 2012

(65) Prior Publication Data
US 2014/0044796 A1    Feb. 13, 2014

(30) Foreign Application Priority Data

Feb. 10, 2011   (DE) .................... 10 2011 003 944

(51) Int. Cl.
  G01N 33/68    (2006.01)
  C12N 9/68    (2006.01)
  C12N 9/64    (2006.01)

(52) U.S. Cl.
  CPC .......... *G01N 33/6845* (2013.01); *C12N 9/6435* (2013.01); *C12N 9/6489* (2013.01); *G01N 33/6896* (2013.01); *G01N 2333/4709* (2013.01); *G01N 2800/2814* (2013.01); *G01N 2800/7047* (2013.01)

(58) Field of Classification Search
None
See application file for complete search history.

(56) References Cited

U.S. PATENT DOCUMENTS

| | | | |
|---|---|---|---|
| 2003/0073138 A1 | 4/2003 | Kientsch-Engel et al. | |
| 2003/0211519 A1 | 11/2003 | Davidson | |
| 2004/0138127 A1 | 7/2004 | Davidson et al. | |
| 2005/0053993 A1 | 3/2005 | Davidson | |
| 2006/0147557 A1* | 7/2006 | Wu et al. | 424/725 |
| 2010/0322856 A1* | 12/2010 | Hardy et al. | 424/1.69 |

FOREIGN PATENT DOCUMENTS

| | | |
|---|---|---|
| CA | 2453140 A1 | 4/2002 |
| CA | 2493539 A1 | 2/2004 |
| DE | 60202008 T2 | 12/2005 |
| DE | 102010043733 A1 | 5/2012 |
| EP | 1328289 A2 | 7/2003 |
| EP | 1380290 A1 | 1/2004 |
| EP | 1820806 A1 | 8/2007 |
| EP | 2007800 A1 | 12/2008 |
| EP | 2058000 A1 | 5/2009 |
| WO | 2004013176 A1 | 2/2004 |
| WO | 2005039616 A1 | 5/2005 |
| WO | 2006039173 A2 | 4/2006 |
| WO | 2007008073 A2 | 1/2007 |
| WO | 2008047370 A2 | 4/2008 |
| WO | 2010052715 A2 | 5/2010 |

OTHER PUBLICATIONS

Reches, M., et al., "Molecular Self-Assembly of Peptide Nanostructures: Mechanism of Association and Potential Uses", "Current Nanoscience", 2006, pp. 105-111, vol. 2, No. 2.

Reijerkerk, A., et al., "Amyloid Endostatin Induces Endothelial Cell Detachment by Stimulation of the Plasminogen Activation System", "Molecular Cancer Research", Jun. 2003, pp. 561-568, vol. 1.

Rosenberg, A., "Effects of Protein Aggregates: An Immunologic Perspective", "The AAPS Journal", Aug. 4, 2006, pp. E501-E507, vol. 8, No. 3, Article 59.

Rosenson, R., et al., "Randomized trial of an inhibitor of secretory phospholipase A2 on atherogenic lipoprotein subclasses in statin-treated patients with coronary heart disease", "European Heart Journal", Nov. 16, 2010, pp. 999-1005, vol. 32.

Rothwell, P., et al., "Effect of daily aspirin on long-term risk of death due to cancer: analysis of individual patient data from randomised trials", "Lancet", Dec. 7, 2010, pp. 31-41, vol. 377.

Rudolph, V. et al., "Myeloperoxidase acts as a profibrotic mediator of atrial fibrillation", "Nature Medicine", Mar. 21, 2010, pp. 470-474 and Online Methods, vol. 16, No. 4.

Scheibel, T., et al., "Conducting nanowires built by controlled self-assembly of amyloid fibers and selective metal deposition", "PNAS", Apr. 15, 2003, pp. 4527-4532, vol. 100, No. 8.

Scheinost, J., et al., "Chapter 28: Role of Oxidative Stress in Protein Misfolding and/or Amyloid Formation", "Protein Misfolding Diseases: Current and Emerging Principles and Therapies (Eds. Ramirez-Alvarado, M., et al.)", Jun. 9, 2010, pp. 615-630, Publisher: John Wiley and Sons, Inc., Published in: Hoboken, NJ.

Scott, H., "Protein-misfolding in neurodegenerative disease", "Internet Journal of Neurology", Jul. 2009, pp. 1-9, vol. 11, No. 2.

(Continued)

*Primary Examiner* — Karlheinz R Skowronek
*Assistant Examiner* — Roy Teller
(74) *Attorney, Agent, or Firm* — Hultquist, PLLC; Steven J. Hultquist; Mary B. Grant

(57) ABSTRACT

The invention concerns the field of detecting and quantifying misfolded proteins/peptides. In particular the detection and quantification of misfolded proteins/peptides in body fluids, on cell surfaces of humans and mammals, the detection of misfolded proteins/peptides in reagents to be tested for scientific research and/or diagnostic use and in pharmaceutical medication or their additives and it concerns as well the removal of misfolded proteins/peptides from reagents to be tested for scientific research and/or for diagnostic purposes and from pharmaceutical medication or their additives. Furthermore the invention includes substances to identify and methods to detect bio-films, a method to examine hemocompatibility of materials and a method to optimize therapeutical products, and to provide reagents microorganisms to charge with for more reliable diagnostics and quality control of biopharmaceuticals and identification substances for the screening for preliminary stages of amyloids that can be used for technical purposes.

36 Claims, 25 Drawing Sheets

(56) References Cited

OTHER PUBLICATIONS

Selkoe, D., "The Origins of Alzheimer Disease: A is for Amyloid", "JAMA", Mar. 22/29, 2000, pp. 1615-1617, vol. 283, No. 12.
Sie, M., et al., "Human recombinant insulin and amyloidosis an unexpected association", "The Netherlands Journal of Medicine", Mar. 2010, pp. 138-140, vol. 68, No. 3.
Stefani, M., et al., "Protein aggregation and aggregate toxicity: new insights into protein folding, misfolding diseases and biological evolution", "J. Mol. Med.", Aug. 27, 2003, pp. 678-699, vol. 81.
Stefani, M., "Generic Cell Dysfunction in Neurodegenerative Disorders: Role of Surfaces in Early Protein Misfolding, Aggregation, and Aggregate Cytotoxicity", "The Neuroscientist", 2007, pp. 519-531, vol. 13, No. 5.
Strittmatter, W., et al., "Apolipoprotein E: High-avidity binding to beta-amyloid and increased frequency of type 4 allele in late-onset familial Alzheimer disease", "Proc. Natl. Acad. Sci. USA", Mar. 1993, pp. 1977-1981, vol. 90.
Strittmatter, W., et al., "Binding of human apolipoprotein E to synthetic amyloid beta peptide: Isoform-specific effects and implications for late-onset Alzheimer disease", "Proc. Natl. Acad. Sci. USA", Sep. 1993, pp. 8098-8102, vol. 90.
Sugiyama, S., et al., "Hypochlorous Acid, a Macrophage Product, Induces Endothelial Apoptosis and Tissue Factor Expression: Involvement of Myeloperoxidase-Mediated Oxidant in Plaque Erosion and Thrombogenesis", "Arterioscler Thromb Vasc Biol.", May 13, 2004, pp. 1309-1314, vol. 24.
Sutherland, W., et al., "Hypochlorous acid and low serum paraoxonase activity in haemodialysis patients: an in vitro study", "Nephrol Dial Transplant", 2004, pp. 75-82, vol. 19.
Sweeny, J., et al., "Antiplatelet drug resistance. Part 1: mechanisms and clinical measurements", "Nature Reviews: Cardiology", Apr. 2009, pp. 273-282, vol. 6.
Tang, W., et al., "Plasma Myeloperoxidase Predicts Incident Cardiovascular Risks in Stable Patients Undergoing Medical Management for Coronary Artery Disease", "Clinical Chemistry", Jan. 2011, pp. 33-39, vol. 57, No. 1.
Taylor, D., et al., "Role of lipid rafts in the processing of the pathogenic prion and Alzheimers amyloid-beta proteins", "Seminars in Cell & Developmental Biology", Jul. 24, 2007, pp. 638-648, vol. 18.
Thuerauf, D., et al., "Activation of the Unfolded Protein Response in Infarcted Mouse Heart and Hypoxic Cultured Cardiac Myocytes", "Circ Res.", Jun. 22, 2006, pp. 275-282, vol. 99.
Topol, E., et al., "Catapulting clopidogrel pharmacogenomics forward", "Nature Medicine", Jan. 2011, pp. 40-41, vol. 17, No. 1.
Van Der Zwan, L., et al., "Hyperglycemia and Oxidative Stress Strengthen the Association Between Myeloperoxidase and Blood Pressure", "Hypertension", Apr. 12, 2010, pp. 1366-1372, vol. 55.
Wang, W., "Protein aggregation and its inhibition in biopharmaceutics", "International Journal of Pharmaceutics", 2005, pp. 1-30, vol. 289.
Watson, L., et al., "Overexpression of the 78-kDa Glucose-regulated Protein/Immunoglobulin-binding Protein (GRP78/BiP) Inhibits Tissue Factor Procoagulant Activity", "J. Biol. Chem.", Mar. 5, 2003, pp. 17438-17447, vol. 278, No. 19.
Westermark, P., et al., "Fibril in senile systemic amyloidosis is derived from normal transthyretin", "Proc. Natl. Acad. Sci. USA", Apr. 1990, pp. 2843-2845, vol. 87.
Westermark, G., et al., "Staining Methods for Identification of Amyloid in Tissue", "Methods Enzymol.", 1999, pp. 3-25, vol. 309.
Wilhelmus, M., et al., "Heat Shock Proteins and Amateur Chaperones in Amyloid-Beta Accumulation and Clearance in Alzheimers Disease", "Mol Neurobiol", Jul. 6, 2007, pp. 203-216, vol. 35.
Wille, H., et al., "Separation of Scrapie Prion Infectivity from PrP Amyloid Polymers", "J. Mol. Biol.", 1996, pp. 608-621, vol. 259.
Williams, D., "Revisiting the Definition of Biocompatibility", "Medical Device Technology", Oct. 2003, pp. 10-13, vol. 14, No. 8.
Wilson, M., et al., "Potential roles of abundant extracellular chaperones in the control of amyloid formation and toxicity", "Molecular Biosystems", Nov. 19, 2007, pp. 42-52, vol. 4, No. 1.
Xu, S., "Aggregation drives misfolding in protein amyloid fiber formation", "Amyloid", Jun. 2007, pp. 119-131, vol. 14, No. 2.
Xu, Z., et al., "Interaction of nano-$TiO_2$ with lysozyme: insights into the enzyme toxicity of nanosized particles", "Environ Sci Pollut Res", Apr. 24, 2009, pp. 798-806, vol. 17.
Ye, R., et al., "Grp78 Heterozygosity Promotes Adaptive Unfolded Protein Response and Attenuates Diet-Induced Obesity and Insulin Resistance", "Diabetes", Jan. 2010, pp. 6-16, vol. 59.
Yerbury, J., et al., "The Acute Phase Protein Haptoglobin is a Mammalian Extracellular Chaperone with an Action Similar to Clusterin", "Biochemistry", Jul. 21, 2005, pp. 10914-10925, vol. 44, No. 32.
Yerbury, J., et al., "Quality control of protein folding in extracellular space", "EMBO Reports", 2005, pp. 1131-1136, vol. 6, No. 12.
Yumlu, S., et al., "Localized insulin-derived amyloidosis in patients with diabetes mellitus: a case report", "Human Pathology", 2009, pp. 1655-1660, vol. 40.
Zhang, Y., et al., "Cell Surface Relocalization of the Endoplasmic Reticulum Chaperone and Unfolded Protein Response Regulator GRP78/BiP", "J. Biol. Chem.", Mar. 5, 2010, pp. 15065-15075, vol. 285, No. 20.
Zhou, J., et al., "Association of Multiple Cellular Stress Pathways With Accelerated Atherosclerosis in Hyperhomocysteinemic Apolipoprotein E-Deficient Mice", "Circulation", Jun. 21, 2004, pp. 207-213, vol. 110.
Zhou, J., et al., "Activation of the Unfolded Protein Response Occurs at All Stages of Atherosclerotic Lesion Development in Apolipoprotein E-Deficient Mice", "Circulation", Apr. 4, 2005, pp. 1814-1821, vol. 111.
Hotamisligil, G., "Endoplasmic reticulum stress and atherosclerosis", "Nature Medicine", Apr. 2010, pp. 396-399, vol. 16, No. 4.
Ratner, B., "The catastrophe revisited: Blood compatibility in the 21st Century", "Biomaterials", Aug. 8, 2007, pp. 5144-5147, vol. 28.
Anfinsen, C., "Nobel Lecture: Studies on the Principles That Govern the Folding of Protein Chains", "Chemistry", Dec. 11, 1972, pp. 55-71.
Cherny, I., et al., "Amyloids: Not Only Pathological Agents but Also Ordered Nanomaterials", "Angew. Chem. Int. Ed.", 2008, pp. 4062-4069, vol. 47.
Shah-Derler, B., et al., "Chapter 7: Blut", "Medizintechnik—Life Science Engineering", 2008, pp. 147-154, Publisher: Springer.
Shah-Derler, B., et al., "Chapter 7: Blut", "Medizintechnik—Life Science Engineering", 2008, pp. 147-154 (Partial English Translation p. 152), Publisher: Springer.
Janson, J., et al., "The Mechanism of Islet Amyloid Polypeptide Toxicity is Membrane Disruption by Intermediate-Sized Toxic Amyloid Particles", "Diabetes", Mar. 1999, pp. 491-498, vol. 48.
Jaross, W., et al., "Biological effects of secretory phospholipase A2 group IIA on lipoproteins and in atherogenesis", "European Journal of Clinical Investigation", 2002, pp. 383-393, vol. 32.
Kayed, R., et al., "Conformational Transitions of Islet Amyloid Polypeptide (IAPP) in Amyloid Formation in Vitro", "J. Mol. Biol.", 1999, pp. 781-796, vol. 287.
Koch, C., et al., "Duration of Red-Cell Storage and Complications after Cardiac Surgery", "N Engl J Med", Mar. 20, 2008, pp. 1229-1239, vol. 358.
Kranenburg, O., et al, "Tissue-Type Plasminogen Activator is a Multiligand Cross-beta Structure Receptor", "Current Biology", Oct. 29, 2002, pp. 1833-1839, vol. 12.
Kugiyama, K., et al., "Circulating Levels of Secretory Type II Phospholipase A2 Predict Coronary Events in Patients with Coronary Artery Disease", "Circulation", 1999, pp. 1280-1284, vol. 100.
Kugiyama, K., et al., "Prognostic Value of Plasma Levels of Secretory Type II Phospholipase A2 in Patients With Unstable Angina Pectoris", "Am J Cardiol", Oct. 1, 2000, pp. 718-722, vol. 86.
Larsen, P., et al., "Amyloid adhesins are abundant in natural biofilms", "Environmental Microbiology", 2007, pp. 3077-3090, vol. 9, No. 12.
Lausevic, Z., et al., "Predicting multiple organ failure in patients with severe trauma", "Can J Surg", Apr. 2008, pp. 97-102, vol. 51, No. 2.
Lee, E., et al., "GRP78 as a Novel Predictor of Responsiveness to Chemotherapy in Breast Cancer", "Cancer Res", Aug. 15, 2006, pp. 7849-7853, vol. 66, No. 16.

(56) References Cited

OTHER PUBLICATIONS

Levinthal, J., et al., "Serum Induced Changes in the Fine Structure of Primary Chick Embryo Cultures", "Experimental Cell Research", 1968, pp. 667-672, vol. 52.

Liu, H., et al., "Rosiglitazone inhibits hypercholesterolaemia-induced myeloperoxidase upregulation—a novel mechanism for the cardioprotective effects of PPAR agonists", "Cardiovascular Research", Nov. 14, 2008, pp. 344-352, vol. 81.

Liu, C., et al., "In Vivo Interrogation of the Molecular Display of Atherosclerotic Lesion Surfaces", "American Journal of Pathology", Nov. 2003, pp. 1859-1871, vol. 163, No. 5.

Liu, P., et al., "Prognostic value and the changes of plasma levels of secretory type II phospholipase A2 in patients with coronary artery disease undergoing percutaneous coronary intervention", "European Heart Journal", 2003, pp. 1824-1832, vol. 24.

Loh, S., "The missing Zinc: p53 misfolding and cancer", "Metallomics", May 18, 2010, pp. 442-449, vol. 2.

Lu, M., et al., "Anti-Citrullinated Protein Antibodies Bind Surface-Expressed Citrullinated Grp78 on Monocyte/Macrophages and Stimulate Tumor Necrosis Factor alpha Production", "Arthritis and Rheumatism", May 2010, pp. 1213-1223, vol. 62, No. 5.

Maas, C., et al., "A Role for Protein Misfolding in Immunogenicity of Biopharmaceuticals", "J. Biol. Chem.", Nov. 29, 2006, pp. 2229-2236, vol. 282, No. 4.

Maas, C., et al., "Misfolded proteins activate Factor XII in humans, leading to kallikrein formation without initiating coagulation", "The Journal of Clinical Investigation", Sep. 2008, pp. 3208-3218, vol. 118, No. 9.

Maas, C., et al., "Identification of fibronectin type I domains as amyloid-binding modules on tissue-type plasminogen activator and three homologs", "Amyloid", Sep. 2008, pp. 166-180, vol. 15, No. 3.

Mallat, Z. et al, "Lipoprotein-Associated and Secreted Phospholipases A2 in Cardiovascular Disease: Roles as Biological Effectors and Biomarkers", "Circulation", Nov. 23, 2010, pp. 2183-2200, vol. 122.

Marcinowski, M., et al., "Substrate discrimination of the chaperone BiP by autonomous and cochaperone-regulated conformational transitions", "Nature Structural and Molecular Biology", Jan. 9, 2011, pp. 150-158, vol. 18, No. 2.

Matsuzaki, T., et al, "Insulin resistance is associated with the pathology of Alzheimer disease: The Hisayama Study", "Neurology", Aug. 25, 2010, pp. 764-770, vol. 75.

Matthijsen, R., et al., "Myeloperoxidase is Critically Involved in the Induction of Organ Damage after Renal Ischemia Reperfusion", "The American Journal of Pathology", Dec. 2007, pp. 1743-1752, vol. 171, No. 6.

Mattsson, N., et al., "Metabolic Syndrome and Carotid Intima-Media Thickness in Young Adults: Roles of Apolipoprotein B, Apolipoprotein A-I, C-Reactive Protein, and Secretory Phospholipase A2: The Cardiovascular Risk in Young Finns Study", "Arterioscler Thromb Vasc Biol.", Jun. 10, 2010, pp. 1861-1866, vol. 30.

Maurer-Stroh, S., et al., "Exploring the sequence determinants of amyloid structure using position-specific scoring matrices", "Nature Methods", Feb. 14, 2010, pp. 237-242 and Online Methods (Correction and Addendum Published Sep. 29, 2010, vol. 7, No. 10), vol. 7, No. 3.

McFarland, B., et al., "Plasminogen Kringle 5 Induces Apoptosis of Brain Microvessel Endothelial Cells: Sensitization by Radiation and Requirement for GRP78 and LRP1", "Cancer Res", Jun. 23, 2009, pp. 5537-5545, vol. 69.

Merlini, G., et al., "Mechanisms of Disease: Molecular Mechanisms of Amyloidosis", "N Engl J Med", Aug. 7, 2003, pp. 583-596, vol. 349.

Merlini, G., et al., "The systemic amyloidoses: clearer understanding of the molecular mechanisms offers hope for more effective therapies", "Journal of Internal Medicine", 2004, pp. 159-178, vol. 255.

Merritt, K., et al., "Use of an enzyme linked immunosorbent assay (ELISA) for quantification of proteins on the surface of materials", "Journal of Biomedical Materials Research", 1988, pp. 99-109, vol. 22.

Meuwese, M., et al., "Serum Myeloperoxidase Levels are Associated With the Future Risk of Coronary Artery Disease in Apparently Healthy Individuals", "J Am Coll Cardiol", Jul. 10, 2007, pp. 159-165, vol. 50, No. 2.

Mintz, P., et al., "Fingerprinting the circulating repertoire of antibodies from cancer patients", "Nature Biotechnology", Dec. 23, 2002, pp. 57-63, vol. 21.

Misra, U., et al., "Heterotrimeric Gaq11 Co-Immunoprecipitates With Surface-Anchored GRP78 From Plasma Membranes of alpha2M Stimulated Macrophages", "Journal of Cellular Biochemistry", 2008, pp. 96-104, vol. 104.

Misra, U., et al., "Ligation of Prostate Cancer Cell Surface GRP78 Activates a Proproliferative and Antiapoptotic Feedback Loop", "J. Biol. Chem.", Nov. 5, 2010, pp. 1248-1259, vol. 286, No. 2.

Moscatta, T., et al., "Plasma Concentrations of Myeloperoxidase Predict Mortality After Myocardial Infarction", "Journal of the American College of Cardiology", May 22, 2007, pp. 1993-2000, vol. 49, No. 20.

Molins, B., et al., "Glucose-Regulated Protein 78 and Platelet Deposition: Effect of Rosuvastatin", "Arterioscler Thromb Vasc Biol.", Apr. 1, 2010, pp. 1246-1252, vol. 30.

Myoishi, M., et al., "Increased Endoplasmic Reticulum Stress in Atherosclerotic Plaques Associated With Acute Coronary Syndrome", "Circulation", Aug. 20, 2007, pp. 1226-1233, vol. 116.

Naiki, H., et al., "Molecular Pathogenesis of Protein Misfolding Diseases: Pathological Molecular Environments Versus Quality Control Systems Against Misfolded Proteins", "J. Biochem.", Jul. 30, 2009, pp. 751-756, vol. 146, No. 6.

Naruko, T., et al., "Increased expression and plasma levels of myeloperoxidase are closely related to the presence of angiographically-detected complex lesion morphology in unstable angina", "Heart", Nov. 2010, pp. 1716-1722 (Erratum published Dec. 2010 in vol. 96, No. 4, pp. 2044-2045), vol. 96.

Obici, L., et al., "The New Apolipoprotein A-I Variant Leu174 Ser Causes Hereditary Cardiac Amyloidosis, and the Amyloid Fibrils Are Constituted by the 93-Residue N-Terminal Polypeptide", "American Journal of Pathology", Sep. 1999, pp. 695-702, vol. 155, No. 3.

Oezcan, U., "Chemical Chaperones Reduce ER Stress and Restore Glucose Homeostasis in a Mouse Model of Type 2 Diabetes", "Science", Aug. 25, 2006, pp. 1137-1140, vol. 313.

Onoue, S., et al., "Mishandling of the Therapeutic Peptide Glucagon Generates Cytotoxic Amyloidogenic Fibrils", "Pharmaceutical Research", Jul. 2004, pp. 1274-1283, vol. 21, No. 7.

Park, S., et al., "The Generation of a 17 kDa Neurotoxic Fragment: An Alternative Mechanism by which Tau Mediates beta-Amyloid-Induced Neurodegeneration", "J Neurosci.", Jun. 1, 2005, pp. 5365-5375, vol. 25, No. 22.

Patrick, D., et al., "Secretory phospholipase A2 activity correlates with postinjury multiple organ failure", "Crit Care Med", 2001, pp. 989-993, vol. 29, No. 5.

Philo, J., "A Critical Review of Methods for Size Characterization of Non-Particulate Protein Aggregates", "Current Pharmaceutical Biotechnology", 2009, pp. 359-372, vol. 10, No. 4.

Porela, P., et al., "Level of circulating phospholipase A2 in prediction of the prognosis of patients with suspected myocardial infarction", "Basic Res Cardiol", 2000, pp. 413-417, vol. 95.

Puchtler, H., et al., "On the Binding of Congo Red by Amyloid", "J Histochem Cytochem", 1962, pp. 355-364, vol. 10, No. 3.

Raiter, A., et al., "Activation of GRP78 on Endothelial Cell Membranes by an ADAM15-Derived Peptide Induces Angiogenesis", "J. Vasc. Res.", Feb. 6, 2010, pp. 399-411, vol. 47.

Rakhit, R., et al., "Oxidation-induced Misfolding and Aggregation of Superoxide Dismutase and Its Implications for Amyotrophic Lateral Sclerosis", "J. Biol. Chem.", Sep. 27, 2002, pp. 47551-47556, vol. 277, No. 49.

Ratner, R., et al., "Persistent Cutaneous Insulin Allergy Resulting From High-Molecular-Weight Insulin Aggregates", "Diabetes", Jun. 1990, pp. 728-733, vol. 39.

(56) References Cited

OTHER PUBLICATIONS

Ahmad, A., et al., "Partially Folded Intermediates in Insulin Fibrillation", "Biochemistry", 2003, pp. 11404-11416, vol. 42.
Ali, Z., et al., "Association of Serum Myeloperoxidase with Peripheral Arterial Disease", "Vasc Med.", Aug. 2009, pp. 215-220, vol. 14, No. 3.
Anfinsen, C., "Untersuchungen ueber die Ursachen der Faltung von Proteinketten (Nobel-Vortrag)", "Angewandte Chemie", 1973, pp. 1065-1124, vol. 85, No. 24.
Anfinsen, C., "Untersuchungen ueber die Ursachen der Faltung von Proteinketten (Nobel-Vortrag)", "Angewandte Chemie", 1973, pp. 1065-1124 (Partial Machine Translation pp. 1065-1066), vol. 85, No. 24.
Asatryan, L., et al., "LDL phospholipid hydrolysis produces modified electronegative particles with an unfolded apoB-100 protein", "Journal of Lipid Research", Oct. 16, 2004, pp. 115-122, vol. 46.
Baldus, S., et al., "Myeloperoxidase Serum Levels Predict Risk in Patients With Acute Coronary Syndromes", "Circulation", Sep. 2, 2003, pp. 1440-1445, vol. 108.
Benson, M., "LECT2 amyloidosis", "Kidney International", May 2010, pp. 757-759, vol. 77.
Bertling, A., et al., "Staphylococcal Extracellular Adherence Protein Induces Platelet Activation by Stimulation of Thiol Isomerases", "Arterioscler Thromb Vasc Biol.", Apr. 26, 2012, pp. 1979-1990, vol. 32.
Bhattacharjee, G., et al., "Regulation of Tissue Factor-Mediated Initiation of the Coagulation Cascade by Cell Surface Grp78", "Arterioscler Thromb Vasc Biol.", Jun. 9, 2005, pp. 1737-1743, vol. 25.
Boekholdt, S., et al., "Serum Levels of Type II Secretory Phospholipase A2 and the Risk of Future Coronary Artery Disease in Apparently Healthy Men and Women: The EPIC-Norfolk Prospective", "Arterioscler Thromb Vasc Biol.", Feb. 3, 2005, pp. 839-846, vol. 25.
Bouma, B., et al., "Glycation Induces Formation of Amyloid Cross-beta Structure in Albumin", "J. Biol. Chem.", Aug. 8, 2003, pp. 41810-41819, vol. 278, No. 43.
Bouman, H., et al., "Paraoxonase-1 is a major determinant of clopidogrel efficacy", "Nature Medicine", Dec. 19, 2010, pp. 110-116 and Online Methods (Erratum published Sep. 7, 2011, vol. 17, No. 9, p. 1153), vol. 17, No. 1.
Brange, J., et al., "Toward Understanding Insulin Fibrillation", "Journal of Pharmaceutical Sciences", May 1997, pp. 517-525, vol. 86, No. 5.
Brennan, M., et al., "Comprehensive Peroxidase-Based Hematologic Profiling for the Prediction of 1-Year Myocardial Infarction and Death", "Circulation", Jun. 21, 2010, pp. 70-79, vol. 122.
Brignull, H., et al., "Chapter 15: The stress of misfolded proteins: C. elegans models for neurodegenerative disease and aging", "Adv Exp Med Biol", 2007, pp. 167-189, vol. 594.
Bystroem, R., et al., "Disordered Proteins: Biological Membranes as Two-Dimensional Aggregation Matrices", "Cell Biochem Biophys", Oct. 31, 2008, pp. 175-189, vol. 52.
Casserly, I., et al., "Convergence of atherosclerosis and Alzheimers disease: inflammation, cholesterol, and misfolded proteins", "Lancet", Apr. 3, 2004, pp. 1139-1146, vol. 363.
Chelbi, S., et al., "Expressional and Epigenetic Alterations of Placental Serine Protease Inhibitors: SERPINA3 is a Potential Marker of Preeclampsia", "Hypertension", Nov. 6, 2006, pp. 76-83, vol. 49.
Chen, J., et al., "HMG-CoA reductase inhibitors activate the unfolded protein response and induce cytoprotective GRP78 expression", "Cardiovascular Research", Jun. 12, 2008, pp. 138-150, vol. 80.
Cherny, I., et al., "Amyloide: nicht nur pathologische Substanzen, sondern auch geordnete Nanomaterialien", "Angew. Chem.", May 19, 2008, pp. 4128-4136, vol. 120.
Cherny, I., et al., "Amyloide: nicht nur pathologische Substanzen, sondern auch geordnete Nanomaterialien", "Angew. Chem.", May 19, 2008, pp. 4128-4136 (Machine Translation Abstract), vol. 120.
Cohen, F., et al., "Structural Clues to Prion Replication", "Science", Apr. 22, 1994, pp. 530-531, vol. 264.
Costerton, J., et al., "Microbial Biofilms", "Annu. Rev. Microbial.", 1995, pp. 711-745, vol. 49.
Cromwell, M., et al., "Protein Aggregation and Bioprocessing", "The AAPS Journal", Sep. 15, 2006, pp. E572-E579, vol. 8, No. 3, Article 66.
Davidson, D., et al., "Kringle 5 of Human Plasminogen Induces Apoptosis of Endothelial and Tumor Cells through Surface-Expressed Glucose-Regulated Protein 78", "Cancer Res", Jun. 1, 2005, pp. 4663-4672, vol. 65.
Deng, W., et al., "Aspirin and salicylate bind to immunoglobulin heavy chain binding protein (BiP) and inhibit its ATPase activity in human fibroblasts", "FASEB J.", 2001, pp. 2463-2470, vol. 15.
De Ridder, G., et al., "Autoantibodies against cell surface GRP78 promote tumor growth in a murine model of melanoma", "Melanoma Research", Dec. 15, 2010, pp. 35-43, vol. 21, No. 1.
Dickhout, J., et al., "Increased Endoplasmic Reticulum Stress in Atherosclerotic Plaques Associated With Acute Coronary Syndrome: A Balancing Act Between Plaque Stability and Rupture", "Circulation", 2007, pp. 1214-1216, vol. 116.
Dische, F., et al., "Insulin as an amyloid-fibril protein at sites of repeated insulin injections in a diabetic patient", "Diabetologia", 1988, pp. 158-161, vol. 31.
Drueeke, T., "Beta2-Microglobulin and amyloidosis", "Nephrol Dial Transplant", 2000, pp. 17-24, vol. 15, Suppl 1.
Feaver, R., et al., "GRP78 Upregulation by Atheroprone Shear Stress Via p38-, alpha2beta1-Dependent Mechanism in Endothelial Cells", "Arterioscler Thromb Vasc Biol.", Jun. 12, 2008, pp. 1534-1541, vol. 28.
Ferrante, G., et al., "High Levels of Systemic Myeloperoxidase Are Associated With Coronary Plaque Erosion in Patients With Acute Coronary Syndromes: A Clinicopathological Study", "Circulation", Nov. 29, 2010, pp. 2505-2513, vol. 122.
Gagnon, P., et al., "Editorial: Aggregation detection and removal in biopharmaceutical proteins", "Current Pharmaceutical Biotechnology", 2009, p. 347 vol. 10, No. 4.
Gebbink, M., et al., "Do antiangiogenic protein fragments have amyloid properties?", "Blood", May 27, 2004, pp. 1601-1605, vol. 104.
Gebbink, M., et al., "Amyloids a Functional Coat for Microorganisms", "Nature Reviews: Microbiology", Apr. 2005, pp. 333-341, vol. 3.
Gebbink, M., et al., "Physiological responses to protein aggregates: Fibrinolysis, coagulation and inflammation (new roles for old factors)", "FEBS Letters", Jun. 13, 2009, pp. 2691-2699, vol. 583.
Gillmore, J., et al., "Amyloid load and clinical outcome in AA amyloidosis in relation to circulating concentration of serum amyloid A protein", "Lancet", Jul. 7, 2001, pp. 24-29, vol. 358.
Giovannini, S., et al., "Myeloperoxidase Levels and Mortality in Frail Community-Living Elderly Individuals", "J Gerontol A Biol Sci Med Sci", Jan. 11, 2010, pp. 369-376, vol. 65A, No. 4.
Glenner, G., et al., "Amyloid Fibril Proteins: Proof of Homology with umminoglobulin Light Chains by Sequence Analyses", "Science", Jun. 11, 1971, pp. 1150-1151, vol. 172.
Greco, G., et al., "Generation in Human Plasma of Misfolded, Aggregation-Prone Electronegative Low Density Lipoprotein", "Biophysical Journal", Jul. 2009, pp. 628-635, vol. 97.
Hall-Stoodley, L., et al., "Bacterial Biofilms: From the Natural Environment to Infectious Diseases", "Nature Reviews: Microbiology", Feb. 2004, pp. 95-108, vol. 2.
Hamedi, M., et al., "Electrochemical Devices Made from Conducting Nanowire Networks Self-Assembled from Amyloid Fibrils and Alkoxysulfonate PEDOT", "Nano Letters", May 9, 2008, pp. 1736-1740, vol. 8, No. 6.
Hardy, B., et al., "Peptide-binding heat shock protein GRP78 protects cardiomyocytes from hypoxia-induced apoptosis", "J Mol Med", Jul. 28, 2010, pp. 1157-1167, vol. 88.
Henry, P., et al., "24-hour time-dependent aspirin efficacy in patients with stable coronary artery disease", "Thromb Haemost", Dec. 7, 2010, pp. 336-344, vol. 105.
Herczenik, E., et al., "Activation of Human Platelets by Misfolded Proteins", "Arterioscler Thromb Vasc Biol.", May 17, 2007, pp. 1657-1665, vol. 27.

(56) References Cited

OTHER PUBLICATIONS

Hermeling, S., et al., "Structure-Immunogenicity Relationships of Therapeutic Proteins", "Pharmaceutical Research", Jun. 2004, pp. 897-903, vol. 21, No. 6.

Ho, L., et al., "Diet-induced insulin resistance promotes amyloidosis in a transgenic mouse model of Alzheimers disease", "FASEB Journal", Mar. 19, 2004, pp. 902-904, vol. 18, No. 7.

Hoffstrom, B., et al, "Inhibitors of protein disulfide isomerase suppress apoptosis induced by misfolded proteins", "Nat Chem Biol.", Oct. 31, 2010, pp. 900-906, vol. 6, No. 12.

Horn, M., et al., "Human neutrophil alpha-defensins induce formation of fibrinogen and thrombospondin-1 amyloid-like structures and activate platelets via glycoprotein IIb/IIIa", "Journal of Thrombosis and Haemostasis", Apr. 2012, pp. 647-661, vol. 10.

Eto, K., et al., "RGD-independent Binding of Integrin alpha9beta1 to the ADAM-12 and -15 Disintegrin Domains Mediates Cell-Cell Interaction", "The Journal of Biological Chemistry", Aug. 15, 2000, pp. 34922-34930, vol. 275, No. 45.

Hatcher, K., et al., "Cryptic Peptides of the Kringle Domains Preferentially Bind to Disease-Associated Prion Protein", "Journal of Alzheimer's Disease", 2009, pp. 421-431, vol. 16.

Mays, C., et al., "Plasminogen stimulates propagation of protease-resistant prion protein in vitro", "The FASEB Journal", Dec. 2010, pp. 5102-5112, vol. 24.

\* cited by examiner

Figure 1 continuance
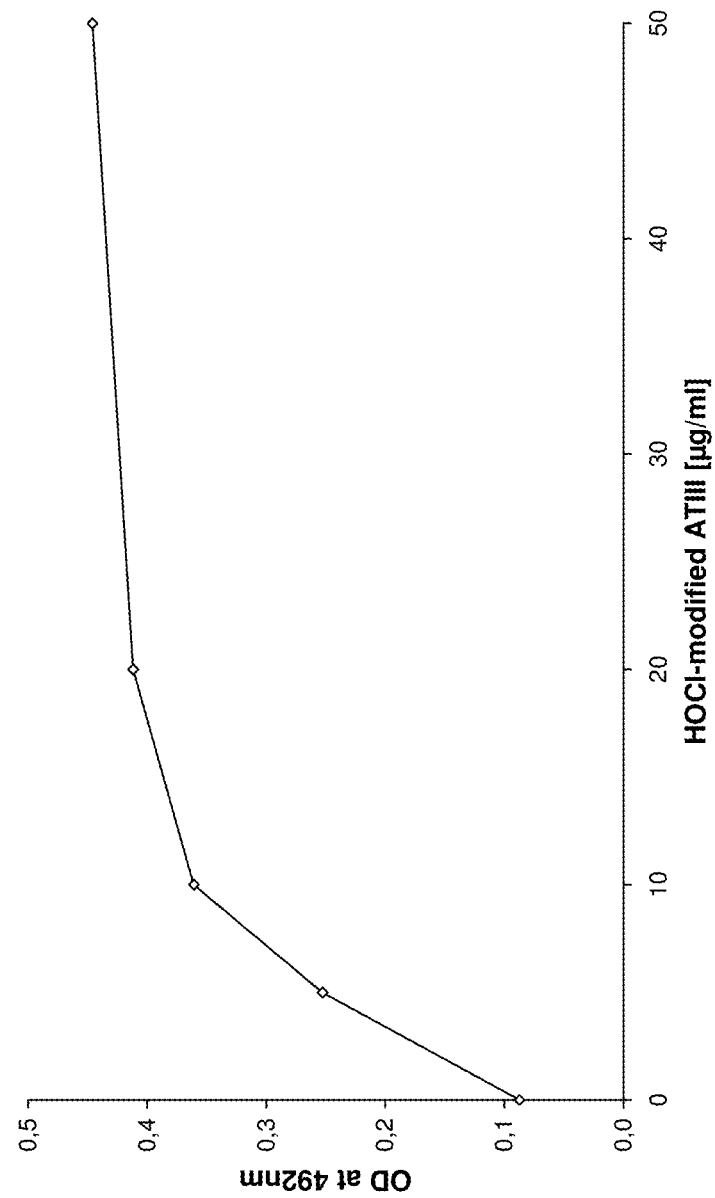

Figure 3 continuance
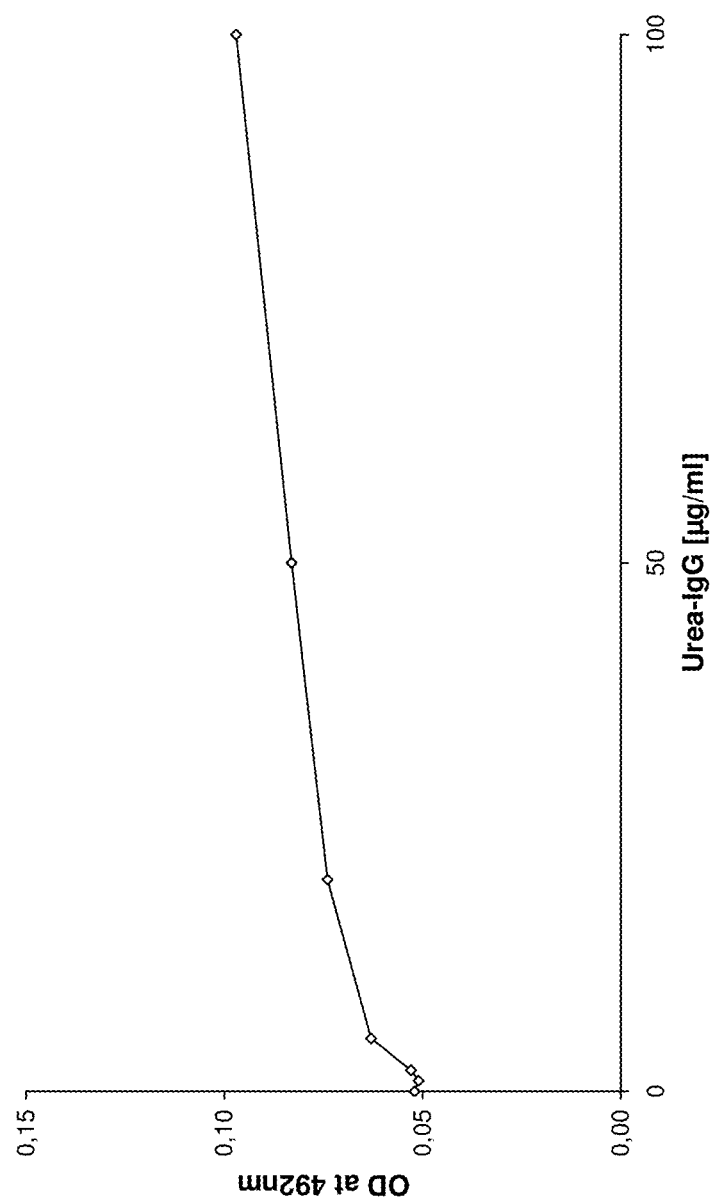

Figure 6

Binding of GPV-fragment to PRKLYDY

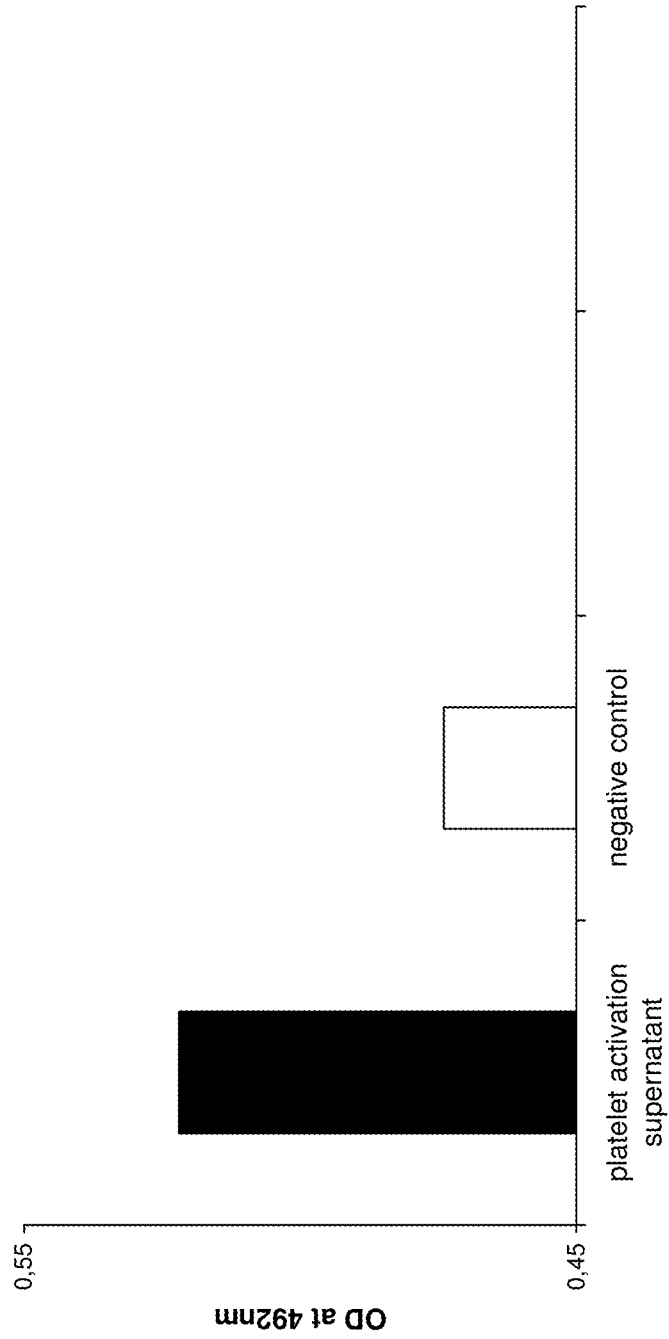
Figure 6 continuance

Figure 8 continuance

Figure 10 continuance

Figure 12

Binding of GPV-fragment to HWRRAHLLPRLP

| | OD at 492nm |
|---|---|
| platelet activation supernatant | ~0.4 |
| negative control | ~0.3 |
| 5µg/ml GPV-fragment | ~0.7 |
| 10µg/ml GPV-fragment | ~0.95 |

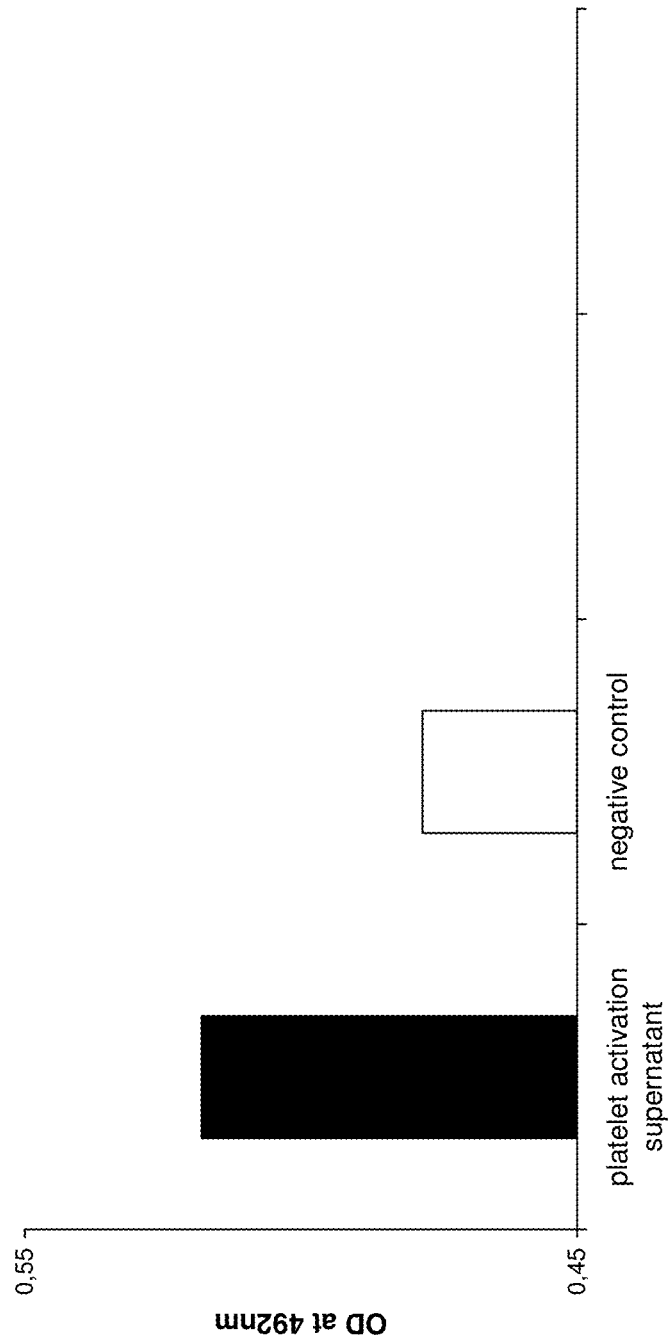
Figure 12 continuance

Figure 13

Binding of HOCl-modified ATIII to HWRRAHLLPRLP

Figure 14 continuance
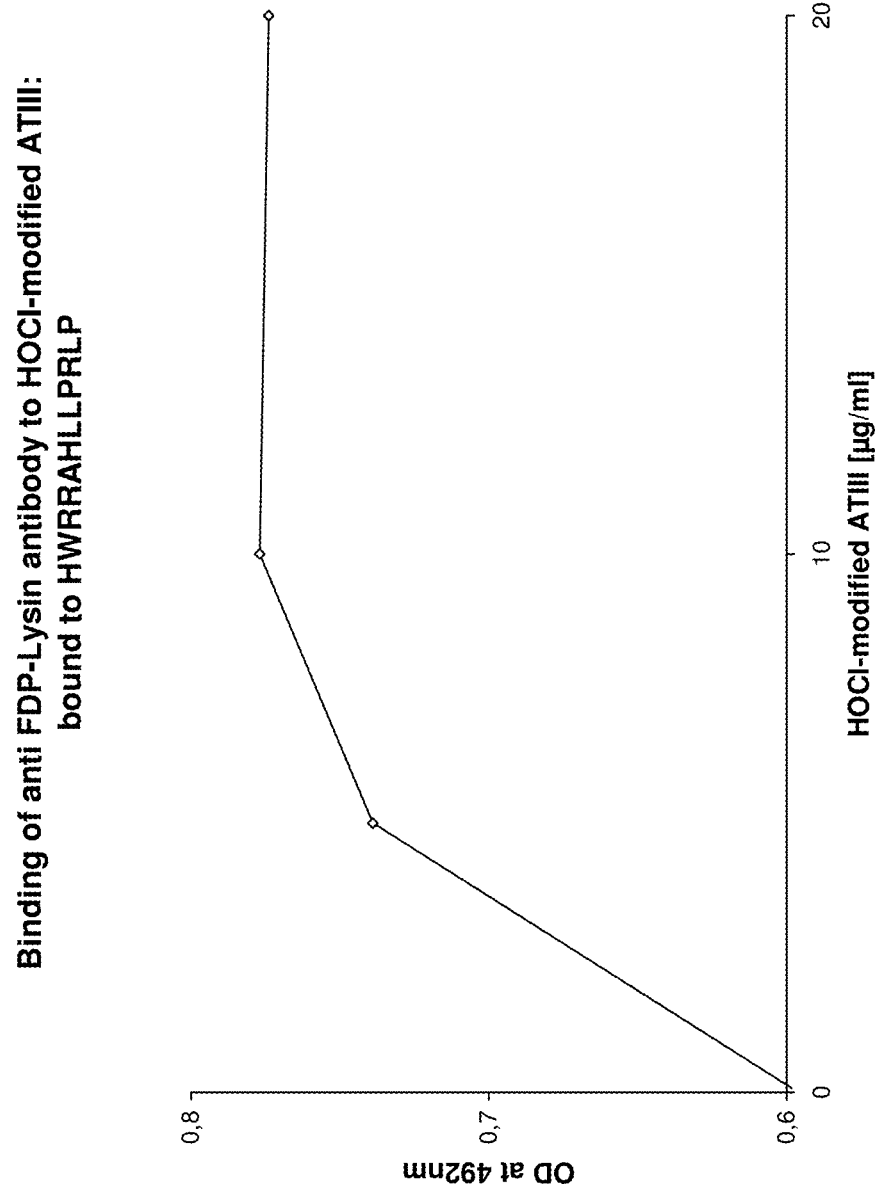

Figure 15 continuance

Misfolded proteins in factor VIII products: binding to HWRRAHLLPRLP

SEQUENCE LISTING

<160> NUMBER OF SEQ ID NOS: 10

<210> SEQ ID NO 1
<211> LENGTH: 8

```
<212> TYPE: PRT
<213> ORGANISM: Artificial Sequence
<220> FEATURE:
<223> OTHER INFORMATION: TSP-1 peptide

<400> SEQUENCE: 1

Arg Phe Tyr Val Val Met Trp Lys
1               5

<210> SEQ ID NO 2
<211> LENGTH: 12
<212> TYPE: PRT
<213> ORGANISM: Artificial Sequence
<220> FEATURE:
<223> OTHER INFORMATION: ADAM15 peptide aa position 286-297

<400> SEQUENCE: 2

His Trp Arg Arg Ala His Leu Leu Pro Arg Leu Pro
1               5                   10

<210> SEQ ID NO 3
<211> LENGTH: 12
<212> TYPE: PRT
<213> ORGANISM: Artificial Sequence
<220> FEATURE:
<223> OTHER INFORMATION: ADAM15 peptide aa position 282-293

<400> SEQUENCE: 3

Glu Asn Phe Leu His Trp Arg Arg Ala His Leu Leu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: ADAM15 peptide aa position 278-289

<400> SEQUENCE: 4

Ala Val Thr Leu Glu Asn Phe Leu His Trp Arg Arg
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Plasminogen peptide

<400> SEQUENCE: 5

Pro Arg Lys Leu Tyr Asp Tyr
1               5

<210> SEQ ID NO 6
<211> LENGTH: 5
<212> TYPE: PRT
<213> ORGANISM: Artificial Sequence
<220> FEATURE:
<223> OTHER INFORMATION: precursor peptide for exemplary amyloid-like
      fibrils
<220> FEATURE:
<221> NAME/KEY: MISC_FEATURE
<222> LOCATION: (1)..(5)
<223> OTHER INFORMATION: repeating unit

<400> SEQUENCE: 6

Val Gly Gly Val Gly
1               5
```

```
<210> SEQ ID NO 7
<211> LENGTH: 5
<212> TYPE: PRT
<213> ORGANISM: Artificial Sequence
<220> FEATURE:
<223> OTHER INFORMATION: precursor peptide for exemplary amyloid-like
      fibrils
<220> FEATURE:
<221> NAME/KEY: MISC_FEATURE
<222> LOCATION: (1)..(5)
<223> OTHER INFORMATION: repeating unit

<400> SEQUENCE: 7

Val Gly Gly Leu Gly
1               5

<210> SEQ ID NO 8
<211> LENGTH: 4
<212> TYPE: PRT
<213> ORGANISM: Artificial Sequence
<220> FEATURE:
<223> OTHER INFORMATION: Plasminogen peptide

<400> SEQUENCE: 8

Leu Tyr Asp Tyr
1

<210> SEQ ID NO 9
<211> LENGTH: 4
<212> TYPE: PRT
<213> ORGANISM: Artificial Sequence
<220> FEATURE:
<223> OTHER INFORMATION: ADAM15 peptide aa position 286-289

<400> SEQUENCE: 9

His Trp Arg Arg
1

<210> SEQ ID NO 10
<211> LENGTH: 5
<212> TYPE: PRT
<213> ORGANISM: Artificial Sequence
<220> FEATURE:
<223> OTHER INFORMATION: ADAM15 peptide aa position 286-290 modified
      with proline

<400> SEQUENCE: 10

His Trp Arg Arg Pro
1               5
```

DETECTION AND REMOVAL OF MISFOLDED PROTEINS/PEPTIDES

CROSS-REFERENCE TO RELATED APPLICATIONS

This application is a U.S. national phase under the provisions of 35 U.S.C. §371 of International Patent Application No. PCT/EP12/52330 filed Feb. 10, 2012, which in turn claims priority of German Patent Application No. 102011003944.9 filed Feb. 10, 2011. The disclosures of such international patent application and German priority patent application are hereby incorporated herein by reference in their respective entireties, for all purposes.

OBJECT OF INVENTION

Using peptides, polypeptides and proteins to identify, quantify and remove misfolded proteins/peptides The invention concerns the field of detecting and quantifying misfolded proteins/peptides. In particular the detection and quantification of misfolded proteins/peptides in body fluids, on cell surfaces of humans and mammals, the detection of misfolded proteins/peptides in reagents to be tested for scientific research and/or diagnostic use and in pharmaceutical medication or their additives and it concerns as well the removal of misfolded proteins/peptides from reagents to be tested for scientific research and/or for diagnostic purposes and from pharmaceutical medication or their additives. Furthermore the invention includes substances to identify and methods to detect bio-films, one method to examine hemocompatibility of materials and a method to optimise therapeutical products, and to provide reagents microorganisms to charge with for more reliable diagnostics and quality control of biopharmaceuticals and identification substances for the screening for preliminary stages of amyloids that can be used for technical purposes.

BACKGROUND OF INVENTION

Protein folding is the process by which provides proteins with their three-dimensional structure.

In order to be able to perform their specific biological assignment proteins have to be folded into a three-dimensional structure. This structure though is not stable in many cases, proteins can in parts or as a whole unfold and thus be in part or as a whole become denatured. When misfolding, a protein will form a structure which does not correspond to its native state. The disposition of partly or complete unfolding or alternative folding of its structure is a genuine feature of all proteins.

Whereas the mechanisms of checking such intracellular misfolded proteins/peptides—especially after polypeptide-synthesis and with mutations—have been widely known, extracellular misfolded proteins and their function have just recently become the subject of research.

Cells are very good at quality controlling as to protein foldings and usually correct or recycle misfolded intracellular proteins through chaperones, ubiquitin proteasome system.

The release buttons for misfoldings with extracellular proteins can vary: e.g., contact of proteins/peptides with glass, lipids, cellular membranes[1], metals and metallic compounds and glucoses-polymere can cause such misfoldings[2]. Even pharmaceutical medication can be misfolded[3].

The phenomenon of misfolded proteins is of particular importance for the investigation of surfacial biocompatibility of graft blood vessels such as cardiac supportive systems and cardiac valve replacement. But protein/peptide misfolding can also be induced by post-translational protein-modification such as glycation[4,5], inevitably effecting "adevanced glycation" end-products or through modification with ROS[6], HOCl, aldehydes—such as acrolein (propenal), 4-hydroxy-2-nonenal—and malondyaldehyd[7], the impact of peptidyl-prolyl-cis/trans-isomerases and proteindisulfidisomerasis[8], enzymatic splitting[9], and through changes by glycolisation or glycolidases. The composition of the various peripherial conditions, detergents, the distribution of zinc[10], Cu, Pb, or ethanol, pH-number, the bio-molecular concentration, contact to membranes and also cholesterol and sphingolipid concentration within the membrane[11,12], and furthermore pressure, shear force and changes in temperature, even contact to other biomolecules have an impact on the misfolding of proteins. Microorganisms aimfully produce misfolded proteins in order to scotch-tape themselves to cellular hosts[13]. That is the way misfolded proteins take in the case of bacteriogenic, viral and mycotic infections, to enter into the blood circulatory system of their host. This same-self phenomenon might also play its part in the incidence of sepsis. Interesting enough, mammals, too, seem to make use of the misfolded proteins/peptides: the alpha-defensins of human granulocytics show effects like misfolded proteins in more than one way. They embed in contact to membranes, sequester the general bonding protein for misfolded proteins t-PA and bond—as we have recently succeeded in demonstrating—to the chaperone GRP78/BIP and furthermore they can activate thrombocytes[14].

In 1968 Levinthal[15] pointed out that the correct folding of a newly synthetised polypeptide would take a longer period of time than the lifespan of the universe itself, if all the possible conformations were tried out having been randomly searched for. As protein folding, however, will take just seconds or even milliseconds we assume that there are resilient interstages. The natural conformation of a protein is similar to the stage of the lowest possible (Gibbs) Enthalpy[16]. Minute variations as to surrounding elements can—as mentioned above—induce the partial generation of oligopeptides/polypeptides/proteins so that the latter again will take to resilient interstages. Partly unfolded/misfolded proteins show a certain disposition to associate with their likes which may induce oligomeric processes, aggregation and the forming of fibrils.

In the 1980s scientists found enzymes which managed to identify misfolded proteins and to cover up their hydrophobical surfaces, the so-called chaperones. To a limited extent these also have the ability to repair misfoldings by means of additional energy. This procedure may, though, induce new problems and the number of disorders based on misfolding proteins/peptides has been on the increase lately. This shows how important the correct protein folding is, and that the protein misfolding is a key mechanism to diseases, which result in serious impairment and disabilities. The misfolding of proteins has been found particularly with patients who suffer from neurodegenerative diseases such as the Alzheimer Disease, BSE, CJD (Creutzfeldt-Jakob-Disease), ALS (amyotrophic lateral sclerosis) or the Parkinson Disease[17].

Misfoldings of proteins and protein-aggregates has furthermore been regarded lately as a mechanism inducing other serious health problems such as arteriosclerosis—inducing peripheral vascular obliteration, myocardial infarction and apoplexy, amyloidosis in context with dialysis, preeclampsy—a hypertensive disease during pregnancy[18], and the immunogenicity of protein/peptide-holding pharmaceuticals[19].

With a large number of misfoldings which could be identified as causes of disease, proteins are converted into orderly aggregates and fibrillars (amyloids) which escape cellular quality control and protein degradation. We do know, though, that in particular the low-molecular intermediates, oligomeres and aggregates are to be seen the causes of serious diseases.

The risk of falling ill through misfoldings of proteins/peptides increases alongside with aging. Scientific researchers assume that the quality control system for protein foldings decreases by aging and that thus the number of illnesses entailed increases[20]. The knowledge we have today on such matters supports the assumption that all misfolded proteins share a common structural mechanism which in most cases is supposed to cause cytoxicity. So oligomeres from misfolded proteins with cellular membranes can have double-bind effects and build up structures which will destroy the selective ionic permeability, and this may induce the perishing of the cells. Misfolded proteins, however, also have an impact directly on fibrinolysis and the kallikrein system, as a fibronectins-type-1 domain in the serine proteases tissue-plasminogen—activator (tPa) and FXII immediately identifies such proteins[21,22].

The activation of fibrinolysis and of the contact-activating system could be seen as a mechanism to cut down or destroy dangerous extracellular misfolded proteins/peptides before they by means of fibrillas become more resistant against proteases[23,24]. In recent years chaperones like GRP78, also known as BIP, and others have been discovered on cellular surfaces. Whereas in the beginning GRP78 was assumed to be found on tumour cells exclusively, we have learned by now that GRP78 can also be detected on other cells under stress. Autoantibodies versus cell-membrane-hosted GRP78 are to be found with many tumour-affected patients particularly suffering from prostate adenocarcinoma, ovary or stomach cancer[25]. Subject to stress like hypoxia, shortage in or abundance of glucosis and the effects of shear force we find GRP78 for instance on endothelium cells, cardiomyocytes, monocytes/foam cells and muscle cells. GRP78 is mainly to be detected with advanced arteriosclerotic lesions and on the surface of the fibroid cap in apolipoprotein-deficient mice and with humans. GRP78 is particularly to be discovered at vascular sites which are rheologically particularly prone to arteriosclerotic disorders[26-28]. Chen et al. found out that statins (HMG-CoA) increase the expression of GRP78[29].

Excessive expression of GRP78 inhibits the proagulante activities of Tissue Factor[30]. GRP78 may e seen as the regulating agent of the Tissue Factor Dependant coagulation[31]. The two independently working teams of Lina Badimon and Beate Kehrel also detected GRP78 also on the plasma-membrane of thrombocytes[32,33]. Herczenik and others have succeeded in presenting evidence that thrombocytes have been activated by misfolded proteins[34]. The team of Beate Kehrel was able to demonstrate that the activating of thrombocytes has been initiated by the various misfolded proteins such as HOCl-modified albumin, EAP from *S. aureus*[35], an alpha-defensin on human neutrphil granulocytes[36] and amyloid renal atrophic TSP-1 peptide RFYVVMWK due to GRP78. GRP78 thus seems to be a receptor on thrombocytes for altered structures/misfoldings in proteins/peptides. The task of GRP78 depends on ATP[37]. Deng et al. have succeeded in showing that aspirin inhibits the activity of GRP78, in fibroblasts by inhibiting its ATP-activities[38]. Scientists of OxProtect GmbH have succeeded in presenting that aspirin/ASS by inhibiting the ATPase-activity of GRP78 also inhibits the activation of platelets by misfolded proteins. Therefore misfolded proteins can be specifically administered for monitoring the reaction of patients to a therapy with ASS/aspirin HOCl-modified misfolded proteins furthermore interact directly with the active metabolites of the thienopyridines. There are two assumptions of why HOCl-modified proteins can have a negative impact on the ADP-induced activating of thrombocytes. The one lies in the fact that HOCl-modified proteins actually can catch active metabolites of the thienopyridines so that less active metabolite is left for inhibiting the ADP-receptors P2Y12. Immobilised HOCl-modified proteins have actually been found in arteriosclerotic walls of blood vessels. Sugyama et al. have discovered HOCl-modified proteins directly under the thrombus at the plaque-erosion site when they examined the arteriosclerotic plaques which had caused the lethal stroke. Scientists of OxProtect GmbH have succeeded in identifying reactive groups on HOCl-modified proteins which bind with high affinity to free thiol groups. These react to the free thiol groups of the active metabolites of the thienopyridines like Clopidogrel and Prasugrel. As the thiol groups of active metabolites of the thienopyridine are essential to inhibiting for inhibiting P2Y12, there are fewer free metabolites for inhibiting P2Y12 in lower concentration. The other assumption is likely to refer to the fact that especially female patients who run a high risk of suffering from vascular incidents one day (myocardial infarction, stroke, peripheral vascular obliteration) have a higher concentration of HOCl-oxidated proteins in their blood; for these patients have been found to have higher concentrations of free myeloperoxidasis in plasma or serum, which is the one enzyme which is held to be responsible for the production of HOCl—as has been recently shown[40-52].

As HOCl-modified proteins in their function of misfolded proteins are a major thrombocyte-activating factor—as shown by means of EP 1 328 289—and as on the other hand misfolded proteins can react to GRP78 on the surface of arteriosclerotic plaques, they themselves are very likely to be envolved in the process of the diseases and that at least some part of the protective mechanisms of the thienopyridines and ASS/Aspirin is based on the inhibiting of the pathogen effects of misfolded proteins.

As to the invention presented here the inventors have furthermore succeeded in discovering that HOCl-modified proteins can be used within laboratory methods for monitoring a thienopyride-based therapy.

One receptor for misfolded proteins on endothelial cells, even muscular cells and monocytes/makrophages is that GRP78. Successful bindings of polypeptides such as Kringel5 from plasminogen or ADAM15 are decisive for apoptose or proliferation, for life or death of the endothelial cell concerned[53-55]. On makrophages GRP78 is associated with G alpha q11. Such activated alpha 2 macroglobulins release a signalling chain in makrophages and tumour cells via GRP78[56]. Autoantibodies binding GRP78 on monocytes induce the production of TNF alpha[57].

Misfolded proteins activate fibrinolysis. This may—as the case of endostatin has proved—lead to the detatching of the endothelial cells from the subendothelial matrix.[58].

It seems highly probable that the cellular functions of GRP78 are under the influence of its misfolded protein ligands and therewith the presence and the degree of concentration of misfolded proteins plays a vital part in such essential issues as cell proliferation or apoptosis, wound healing and the generation of thrombosis.

GRP78 is involved in the cellular internalization of microorganisms and proteins. Even peptides bound to GRP78 on cellular surfaces can get internalised[59].

This might induce stress in the reticuloendothelial system. ER-stress has recently been identified as a prime mover for arteriosclerosis, type-II diabetis, obesity and their secondary diseases[60-63]. Life without any GRP78 is not possible.

GRP78+/− heterozygous mice are resistant against diet-induced hyperinsulinemia, the generating of a steatohepatitis, inflammation within white adipose tissue and hyperglycemia. There is the interesting fact that these mice in spite of high-calorie, fatty diets did not put on weight[64,65]. In white adipose tissue GRP78 heterozygosity related to fatty diets induced an increase in adaptive response towards unfolded proteins (unfolded protein response (UPR)) and improved quality control of the endoplasmatic reticulum. That way obese and type II diabetic Grp78+/− mice recovered. These results clearly show the importance of quality control versus misfolded proteins for the homeostasis of energy-balance and glucose metabolism.

ER-stress may induce apoptosis of even muscular cells. Thus ER-stress is very likely to contribute a fair share in plaque-rupturing[66]. And it is also likely that by generating a ligand thereof. OxLDL being a misfolded protein, too, modulates or even regulates the generating of foam cells which then is one of the initial steps toward arteriosclerosis.

In addition to cellular chaperones there are extracellular soluble proteins which may carry out chaperone-like tasks[67]. Among these proteins we find e.g., the alpha2 macroglobulins, clusterin (apolipoprotein 3), serum amyloid P and haptoglobins[68-70]. These proteins bind to misfolded proteins and facilitate the intracellular absorption of those complexes through Scavanger receptors such as "low-density lipoprotein receptor related to protein" (LRP, CD68, CD91), CD36, Scavanger receptor A, Scavanger receptor B-I, and RAGE. Complexes on misfolded proteins and chaperone-like soluble proteins can be detected in blood, plasma, and serum.

But also apolipo-proteins in particular apolipo-protein E (apoE), complement factors such as C1q and heparan-sulfate-proteoglycans can sequester misfolded proteins and thus contribute to their displaying their malicious effects on living organism. This has at length been described for amyloid beta, the culprit agent of the Alzheimer Disease[71-73]. Isoforms and variations among species have an impact on the effect of ApoE as to the self-association/aggregation and removal of amyloid beta protein.

Complexes of apolipoproteins or complement factors and misfolded proteins might thus become useful markers for disorders where misfolded proteins are involved, and heparan-sulfate-proteoglycans should contribute to the identification of misfolded proteins. Whether ApoE contributes via reaction to extracellular misfolded proteins towards the generating of arteriosclerosis is at present still a highly speculative matter.

Arteriosclerosis and resulting vascular diseases such as myocardial infarction, stroke, periphere vascular obliteration and the Alzheimer disease are related diseases. They both are based on a reaction of inflammation, on the impact of cholesterol, and sphingolipids in the cellular membrane and on the symptomatical appearance of misfolded proteins[74].

In context with arteriosclerosis and diseases resulting thereof such as angina pectoris, myocardial infarction, TIA, stroke, peripheral vascular obliteration particularly the misfoldings of those proteins are of interest which have been induced by reaction to a product of myeloperoxidase or by sPLa2 and of particular interest on the grounds that these two enzymes themselves are excellent bio-markers of increased vascular risk[75-77]. Inhibitors of sPLA2 as therapeutical devices have already been put on clinical tests. Detection of sPLA2-activity induced misfoldings of LDL would therefore be highly desirable also for the monitoring of therapy with PLA-2 inhibitors. Amyloid insulin-residue have already been discovered with type-2 diabetics and other elderly patients.

Hyperinsulinemia- and hyperglycemia-induced resistance against insulin cause an increase in generating of plaque as to neuritis with Alzheimer Disease patients[78,79]. A dangerous feature of insulin is the disposition it shows of generating amyloid fibrillars. Misfolded insulin in the form of fibrillar insulin residue has been discovered with diabetic patients[80,81]. Insoluble insulin fibrillars may lead to a blockage of hypodermic needles for injections in the attempt of applying pharmaceutical insulin medication and are also held responsible for immunologic intolerance reactions which at times occur during therapy with pharmaceutical insulin medication[82,83]. Preliminary stages of fibrillars from misfolded proteins serve as a sort of solidification nucleus for the generation of larger aggregates and fibrillars. In addition to residue with type-II diabetics the generation of fibrillars forms, however, a big problem in production, storage, and application of soluble insulin in diabetic medication. Preliminary stages of fibrillars through misfolded proteins serve as a solidification nucleus for the generation of larger aggregates and fibrillars. Thus it is essential for the insulin production and for the application to the patient, to identify even partly unfolded/misfolded insulin and to eliminate this from medication and its preliminary stages as well. WO/2004/013176 describes such a method of cleansing preproinsulin which considerably reduces the forming of insulin fibrillars.

As misfoldings of extracellular proteins is such an essential phenomenon in the pathogenesis of diseases but misfolded proteins are also very useful as nano-materials, methods of detection of misfolded proteins/peptides have been described.

Misfolded proteins show some disposition for associating within their own kind[84]. In this procedure they can form oligomers, amorphous aggregates of various size or regularly ordered fibrillars. Such fabrillars are called amyloids. Some authors have already described misfolded proteins/peptimonomers, -oligomers and -aggregates as amyloids. In-vitro-generated fibrillars from misfolded proteins are also called amyloids by some other authors[85]. Fibrillars usually are of ca. 10 nm in diameter and can be of various lengths. Extracellular amyloid residue as to be found with the ordinary amyloidosis can be identified by the color of congo red when exposed to polarised light which then leads to a greenish double-refraction ("apple-green bi-refringence" so-called dichroism)[86,87]. Other methods of detection for discovering amyloid fibrillas are thioflavin S-fluorescence or the analysis of fibrillars by means of x-ray-diffraction. Both methods, though, are poor at detecting misfolded protein/peptide-monomers, -oligomers and aggregates or altogether fail in that respect.

In the beginning just filibrary structures were recognised in their pathogenic function, which form the basis of classic amyloidosis[88,89]—such as immunoglobulin-light chains[90], amyloid A[91], transthyretin[92], cystatin C, apolipoprotein A-I[93], gelsolin, fibrinogen Aalpha-chain, lysozyme, apolipoprotein A-II (2001), Islet amyloid polypeptidide (IAPP)[94,95], leucocytes, chemotactic factor 2, LECT2[96], Alzheimer amyloid beta-peptides[97], prion protein[98-100], beta2 microglobulin[101].

But now, after discovering that the misfoldings of proteins is not limited to just a few proteins but that it is a general feature it is absolutely essential to identify non-fibrillar conformations of misfolded proteins as well; and we have determined to find out about mechanisms which may be useful for all misfolded proteins/peptides or at least for a large part of these proteins/peptides for purposes of identification, sequestering, concentration and elimination.

Misfolded proteins according to the invention are very heterogeneous. They include monomer misfolded proteins/ peptides, the range of small to large oligomers of misfolded proteins/peptides, large amorphous-looking aggregates of misfolded proteins/peptides up to large well-ordered fibrillar structures. They have in common—no matter what their amino acid sequence is—certain qualities which are very helpful in scientific research, medicine or for commercial use.

EP 1 380 290 describes the bond of misfolded proteins to the tissue-plasminogen-activator (tPa), the activating of the fibrinolysis by misfolded proteins and the use of fibrinolysis for fighting misfolded proteins.

EP 2 007 800 describes methods of identifying beta-structured misfolded proteins by bondings to chaperones, in particular to GRP78/BIP, clusterin, HSP72 or hapoglobins. In this respect others have been already mentioned as possible bonding proteins such as HSP60, HSP90, DNAK, HGFA, tPA, plasmogen, factor XII, IVIg, and the cellular receptors low density lipoprotein receptor related protein (LRP, CD91), CD36, Scavenger receptor Am, Scavenger receptor B-I, and RAGE.

EP 1 820 806 gives a description of an antibody which is able to identify misfolded proteins.

EP 2 058 000 describes the intensification of immune response by misfolded proteins and the use of misfolded proteins to support an immune response.

WO2007/008073 gives an insight into the impact of detecting and quantifying by comparing the contents of misfolded proteins in a sample with that in a corresponding sample after the test sample has been altered in a way which makes the alteration in the contents of misfolded proteins foreseeable. The method of identifying then is described as the activating of fibrinolysis via tPA and the activating of the kallikrein systems via FXIIa which in turn shares homologuous elements with tPA. That survey describes further binding substances for misfolded proteins such as thioflavin T (ThT), congo red, ThT, recombinant finger domains of tPA, FXII, HGFA, and fibronectins; serum amyloid P component (SAP), antibody versus misfolded proteins and a soluble fragment of the receptor "advanced glycation end-products" (sRAGE).

PROBLEMS WHICH CAN BE SOLVED BY THE INVENTION

As to methods for detecting, quantifying, imaging, concentrating proteins/peptides, depleting/diminishing the concentration of proteins/peptides, for the monitoring of therapies which are based on the bond of a sample reagent with a misfolded protein/peptide it is more favorable if the test reagent itself is not a protein/peptide. Proteins being used as test reagents themselves as described in the above-mentioned application for a patent can become misfolded by a number of circumstances such as storage, oxidation, temperature, impact of lipids in particular free essential fatty acids and cholesterol, glycation, the influence of membranes, the impact of methods of virus activation like solvent-detergent-(S/D) approaches, pasteurization, dry heating, pH4-procedures, nanofiltration, ionic strength, exposure to irradiation, increase in concentration, freezing and defrosting, contact to unfavourable materials. By using a protein or polypeptide as binding partner agent for misfolded proteins the malformation of the binding substance in the test (analyt, indicator) induces a variable, non-reproducible results. With the patent application DE60202008 a similar problem was described as to a method for detecting and quantifying "advanced glycation end-products". Furthermore in such a procedure of detecting, quantifying, imaging, and concentrating of proteins/peptides, of depletion/diminishing the concentration of proteins/peptides, the monitoring of therapies no additive reagent must contain/hold misfolded proteins/peptides. Complete proteins or larger parts thereof as they are suggested to be used in the above-mentioned patent applications, are furthermore expensive because they have to be produced in the recombinant way or have to be cleansed from biologic material. As to methods of cleansing pharmaceutical medication from proteins/peptides, and as to adsorption of ligands from misfolded proteins from body fluids and as to the application in the body e.g., as to imaging it is essential that the test substance will not induce defense action/production of antibodies. For the procedure of imaging within the body of mammals or humans a small-size test reagent is of advantage.

The importance of extracellular misfolded proteins/peptides for biochemic and pathobiochemical procedures in organisms especially in mammals and humans has been widely recognised. Unfortunately many pharmaceutical medications and medical additives hold misfolded proteins. These have to be detected and the pharmaceutical and/or the additive thereof. Also in the processes of production, cleansing, storage, and virus-decontamination misfoldings may occur on various grounds in pharmaceutical products and the preliminary stages thereof. So a method would be desirable which identifies misfolded proteins so that all procedures leading to the production of a pharmaceutical medication product can be examined for misfolded proteins/peptides and their quantity measured. Particularly with blood samples or proteins/peptides produced in a recombinant method even the basic raw material of the production of pharmaceutical medication can hold misfolded proteins. The impact of misfolded proteins on the various physiological and pathophysiological processes has been under intensive survey. To avoid false conclusions as to the tests and their results the concentration of misfolded proteins in all the reagents has to be known. Favourably none of the additive reagents should hold misfolded proteins. Reagents as well as additives in cellular structure, additive proteins for stabilizing or inhibiting of undesirable interactions such as—but not limited to—serum or growth factor for the cell culture, albumins or skim milk powder for inhibition are particularly affected thereof. The binding reagent of misfolded proteins has to be particularly qualified of detecting and quantifying misfolded proteins as well as of applying methods to deplete/diminish misfolded proteins, but it also has to be suitable for the accumulation thereof, if such proteins/peptides are to be used effectively.

BILL OF DISCOVERY OF THE INVENTION

The object of the invention presented here are ADAM15 (Metargidin), the metalloprotease domain of ADAM15 and in particular of peptides which hold the sequence His, Trp, Arg, Arg, Ala, His, Leu, Leu, Pro, Arg, Leu, Pro (HWRRAHLL-PRLP) corresponding to the ADAM15 sequences 286-297, the sequence Glu, Asn, Phe, Leu, His, Trp, Arg, Arg, Ala, His, Leu, Leu (ENFLHWRRAHLL) ADAM15 sequences 282-293, or the sequence Ala, Val, Thr, Leu, Glu, Asn, Phe, Leu, His, Trp, Arg, Arg ADAM15 sequences 278-289 or His, Trp, Arg, Arg (HWRR).

In patent applications WO 2005039616 and WO 2008047370 the above-mentioned ADAM15 peptides in their capacity to bind directly to GRP78 are described as therapeutic medication for the increase of angiogenesis. In WO 2010/052715 ADAM15 sequences, its metalloid protease-domain and the above-mentioned ADAM15 sequences have been mentioned as therapeutics for local treatment of cardiovascular disorders. The patent application WO/2010/052715 explains the use of peptides with implantable devices such as stents for attracting endothelial progenitors, for locally intensifying angiogenesis and for inhibiting endothelial cellular apoptosis in abnormally altered sites of the cardiovascular system. The instructions in the patent application points out that ADAM15 and its above-mentioned peptides directly bind to GRP78/BIP on endothelial cells and thus achieve its protection. These peptides can be used for recruiting endothelial preliminary cells e.g., from the umbilical cord and from peripheral blood. Their effect on endothelial preliminary cells is a chemo-tactic one and increase the proliferation of endothelial cells. As the three inventors as to the latter three patent applications have considered the protein GRP78/BIP as a direct binding partner and as a protein that is to be held responsible for the increase in angiogenesis there was no search for further or alternative binding partners and the use of peptides for diagnosing was not considered.

All the more surprised we found out that ADAM15 (Metargidin), the metalloid protease-domain of ADAM15 and in particular peptides with sequence His, Trp, Arg, Arg, Ala, His, Leu, Leu, Pro, Arg, Leu, Pro (HWRRAHLLPRLP) corresponding to the ADAM15 sequences 286-297, hold the sequence Glu, Asn, Phe, Leu, His, Trp, Arg, Arg, Ala, His, Leu, Leu (ENFLHWRRAHLL) ADAM15 sequences 282-293, or the sequence Ala, Val, Thr, Leu, Glu, Asn, Phe, Leu, His, Trp, Arg, Arg ADAM15 sequences 278-289, or the sequence His, Trp, Arg, Arg, Pro or His, Trp, Arg, Arg (HWRR) are general binding partners with a high degree of affinity for misfolded proteins.

A further object of our findings is related to the Kringel 5 domain of plasminogen and in particular peptides with the sequence Pro, Arg, Lys, Leu, Tyr (PRKLYDY) or peptides holding the sequence PRKLYDY.

US2004138127 describe the Kringel 5 domain and his fusion products as therapeutic medication for inhibiting angiogenesis. US 20030211519 describe that the Kringel 5 domain of plasminogen binds to GRP78/BIP on endothelial cells and that thus GRP/BIP alongside with the Kringel 5 domain of plasminogen can be used as inhibitors to of angiogenesis which imitate the effects of plasminogen on GRP78, so-called K5 mimetics. The patent application identifies the peptide from the Kringel 5 domain, PRKLYDY as a direct marker sequence for GRP78/BIP. WO 2006039173 describes the applying of GRP78/BIP or of some other endothelial cell receptors to which binds the Kringel 5 domains of the plasminogen as a device to identify pharmaceutical medications which inhibit angiogenesis.

Surprisingly enough we have found out that also the Kringel 5 domain of plasminogen and in particular the amino acid sequence PRKLYDY or amino acid sequences holding sequence PRKLYDY are general binding partners with high affinity to misfolded proteins.

The object of the invention presented are binding partners with a high degree of a natural, general affinity to misfolded proteins/peptides by means of which misfolded proteins/peptides can be detected and quantified. Object of the invention presented here are also binding partners for misfolded proteins/peptides used for surveying and monitoring of the therapeutic applications. Furthermore the inventory substances are of such nature as to deplete/diminish misfolded proteins/peptides from body fluids, pharmaceutical medication or additives in medication, from reagents for diagnostic purposes, from research reagents as well as from additives in research reagents and also from foods, from drink and tobacco, nutritional supplements and from drinkable or non-drinkable water as long as they hold misfolded proteins/peptides. Besides all this the subject of the invention presented here are substances and methods of monitoring, optimizing and quality control of biopharmaceuticals, of the exploration of biocompatibility of materials and of studying the influencing of supportive and quantifying systems for application within or at the bodies of mammals or humans in particular as to implantable supportive systems, on cells, tissue and body fluids by means of which such systems can be optimised. A favored performance as to the invention presented includes the use of one or several binding partners according to invention and methods of detecting, of intensifying and of immobilization of misfolded proteins/peptides for technical use.

Specific performances of the invention are going to be discussed in more detail now.

1. The Use of Binding Substances According to Invention for Detection and Quantification of Misfolded Protein/Peptides (Diagnostics of Disorders, Methods and Kits)

According to a highly favored performance of the invention presented ADAM15 (Metargidin), the metalloid protease-domain of ADAM15 and in particular peptides holding the sequence His, Trp, Arg, Arg, Ala, His, Leu, Leu, Pro (HWRRAHLLPRLP) corresponding to ADAM15 sequences 286-297, the sequence Glu, Asn, Phe, Leu, His, Trp, Arg, Arg, Ala, His, Leu, Leu (ENFLHWRRAHLL) ADAM15 sequences 282-293 or sequence Ala, Val, Thr, Leu, Glu, Asn, Phe, Leu, His, Trp, Arg, Arg ADAM15 sequences 278-289, His, Trp, Arg, Arg, Pro or His, Trp, Arg, Arg (HWRR) and also holding Kringel 5 domain of plasminogen and in particular the amino acid sequence PRKLYDY or the amino acid sequences which hold the sequence PRKLYDY, generally bind misfolded proteins with a high degree of natural/genuine affinity. They can therefore be used as binding substances in methods and kits for detection and quantification of misfolded proteins in body fluids or tissue abstracts of mammals and humans and for bio-imaging of misfolded proteins clinging to the walls of systems which are run through by blood, lymph, or liquor, e.g. for the bio-imaging of arteriosclerotic plaques and of residue in the brains with patients suffering from neurodegenerative disorders.

In a first performance these binding substances are according to invention part of a new diagnostic test system. In a particularly favored performance of the invention this invention is related to the making use of the above-mentioned proteins, protein fragments and peptides in as diagnostic devices in which at least one of the described proteins, protein fragments or peptides has been chosen. The knowledge of such systems is a household-number to the expert.

In a favored performance the identification of the misfolded proteins/peptides outside the human or animal body and the identification will take place in an ex-vivo/in vitro diagnosis. In a further performance of the invention this same-self invention refers to the application of the aforementioned proteins, protein fragments and peptides as diagnostic device, a process in which at least one of the disclosed proteins, protein fragments or peptides is chosen.

One particularly favored performance of our invention is the direct or indirect binding or fixation of the binding substance—according to invention—to a solid surface. After the washing out and blockage of possible unspecific bindings the solution put to test (preferably body fluids) like—but not exclusively—blood, serum blood plasma, lymph, sperm, vaginal fluid, amniotic fluid, cerebrospinal fluid, synovial fluid, urine, sputum, fluid from lavages such as bronchoalveolar fluid, peritoneal lavage fluid, has to be put in contact with a tissue abstract that has a solid surface and holds one or more binding substances according to invention so that potentially existing misfolded proteins/peptides get immobilised. These will then after further lavations be detected as ordinary misfolded proteins/peptides or be quantified. That procedure may according to a favored performance of invention be carried out by means of a Plasmon resonance method or by using in a sandwich assay another ordinary binding substance which then according to invention can be an already noted binding substance such as a chaperone, a Scavanger receptor, t-Pa, FXII, HGFA or Congo red or thioflavin. There may, however, also specific misfolded proteins be detected and quantified, one of the numerous proteins which have been discovered to show a disposition to misfolding or which are supposed to be of that disposition. Detection is then carried out by means of a detection reagent specific for the individual protein/peptide sought-after. Particularly convenient in this case are specifically marked antibodies against that individual protein/peptide. The range of choice of the various detection reagents depends on the disease which is to be prognosticated or detected. In a further performance also those misfolded proteins/peptides become measurable which hold a specific group that is reactive to a specific indicator substance such as—but not limited to—protein modifications via the effects or acrolein and other electrophile substances, glycations, proteolytic cleavage, phosphorylation, dephosphorylation, glycation, acetylation, S-nitrosylation, citrullination or sulfation. Reagents for detection of such reactive groups are well-known and available commercially.

In one performance the binding substances get—according to invention—bound or fixed to a solid surface which is part of an assay or of a diagnostic facility.

This in a favored performance can be a microtiter plate, a chip for a surfacial Plasmon resonance check-up, a microarray chip, a filter such as nitrocellulose, nylon or PVDF, a membrane, a magnetic or fluorophore-marked bead, a silicon-wafer, glass, metal, synthetic material, a chip, a mass spectrometric target or a matrix as well as beads for examination in flow cytometers.

According to this invention qualified performance is carried out by assays and devices such as ELISA, bead-based assay, Western Blot, affinity chronomatographic devices (such as so-called lateral flow affinity ligand assays) or similar single- or multiplex evidencing methods as well as Plasmon resonance. A microarray chip according to invention is the systematic assembly of binding substances on a solid surface for misfolded proteins and other substances to be evidenced which may give information on a disorder, the probability and risk of getting effected by a specific disease or of substances that are intended for the monitoring and the surveying of therapeutic treatment. The binding substances as disclosed here are to be printed on a modified microscopic slide in a specific site. The evidencing of possibly misfolded proteins/peptides on the bio-chip is carried out in two steps. In a first step of incubation the biochip covered with the binding substance according to invention is incubated by a human body fluid preferably blood, plasma or cerebrospinal fluid so that existing misfolded protein/peptide are bound on the biochip. In a second step of incubation the bound misfolded proteins/peptides get identified, detected and quantified by means of a second binding reagent for misfolded proteins/peptides which is linked to an identification system or by means of antibodies against a native epitope of the misfolded protein/peptide, this epitope being linked to an identification system or by special detection reagents against protein-modifications, that are linked to a identification system. The ratio of a specific protein/peptide in body fluid and one specific misfolded protein/peptide as identified by a method according to invention makes up the percentage amount of misfoldings for one particular protein/peptide and is part of the invention.

Visualization of the reciprocity—according to invention—of the here disclosed binding substances on the one hand and misfolded proteins/peptides on the other hand can be achieved by means of common procedures of verifying the successful binding e.g., by using fluorescent markers, by biotinylation, radioisotope marking or by colloidal gold- or latex-particle marking as well as through enzyme-reactions with signalling substrates or chemiluminescence devices in the ordinary way.

In one further performance of our invention the binding substances according to invention get marked by an identifying label. Marks or parts thereof such as one component of a specific binding pair, can be covalently bound to the molecule to be identified—a procedure experts have been familiar with and in many cases suitable reagents have been commercially available. Appropriate identifying labels can be—but not exclusively limited to—fluorescent markers, such as Dil, FITC, PE, PerCp Cy-, Alexa-, dyomics or similar fluorescent colorants, biotin, a HIS-tag, a GST-tag, a SEAP-tag, a maltose binding protein-tag (MBP-tag), or a FLAG-tag. Digoxigenin, a paramagnetic atom, a radio-active atom such as carbon-11, iodine-125/123, $^{99m}$Tc, Cu-64 or 111In, as well as reporter-enzymes like alkali phosphatase, red cole peroxidise, beta-galactosidase, glucose-oxidase, luciferase, beta-lactamase, urease or lysozyme etc. alongside with the corresponding colorimetric, fluorescent or chemoluminescent substrates. The identifying reactions related thereto such as the conversion of o-phenylenediamine, 4-chloro naphthol or tetramethylbenzidine by red cole-perioxidases, are also a household number to the expert.

With another favored performance the detection and quantification or semi-quantification is carried out within and on tissue and cells of the bodies of mammals and preferably humans. For this procedure marked binding partners according to invention are applied by means of the ordinary and to experts well-known methods of histo-chemistry or flow-cytometry in order to identify and quantify proteins/peptides.

With one furthermore favored performance the detection of misfolded proteins/peptides inside the human or animal body, and the detection is achieved with vivo-diagnosis by means of bio-imaging methods. This makes sense in particular with patients suffering from arteriosclerotic disorder of their blood vessels or from neurodegenerative diseases in order to diagnose a serious disease or stratify risks even before serious symptoms show up. A favored performance herewith is the bio-imaging of arteriosclerotic plaques.

With a yet further performance the identification of misfolded proteins/peptides is carried out by means of a DIP-stick used with the method of immobilization of one of the binding substances according to invention, preferably on a filter or a membrane. The DIP-stick is put in contact with the test sample so that by capillary forces the sample fluid will be drawn across the site where one of the binding substances has been firmly fixed. The identification will be carried out as described above for other methods as well by means of a further detection reagent which is linked to a visualization-system.

Methods according to invention can be used for diagnosing, stratifying and/or monitoring a disorder related to pathodenesis through misfolded proteins. These are in particular disorders related to the generation of amyloids such as the group of classic amyloidosis and neurodegenerative diseases but also diabetes, the metabolic syndrome, obesity, arteriosclerosis and their subsequent diseases, bleedings, thromboses, DIC, kidney failure, hemodialysis, cataract, multiple myeloma, lymphoma, sepsis, serious tissue trauma, status post on-pump coronary artery bypass, organ transplantation, status post implantation of cardiac supporting-systems, pancreatitis, status post reanimation, ischemia-reperfusion damage, and preeclampsia.

The term diagnosis includes clinical diagnostics and related examination, in particular in-vivo and laboratory diagnostics and in-vivo imaging. Risk-stratification or therapy control according to this invention means that our method according to invention will allow for therapeutic decisions concerning the treatment of the patient either hospitalization of the latter or application, effect and/or dosage of one or more pharmaceutical medication, a specific therapeutic procedure or the monitoring of the course of disease as well as the progress of therapy respectively etiology or classification of a disease e.g. in a new or an already existing sub-type or the differentiation of diseases and their respective victims. In a further performance of our invention the term "stratification" includes risk stratification in particular as well as the "outcome" of an unfavourable health incident. In the frame of this invention the "patient" is defined as any proband—be it human or mammal—understanding that the proband will undergo an examination in terms of disease or preliminary stage thereof, related to pathogenesis supposedly caused by misfolded proteins/peptides.

With a favored performance of the invention the procedure also includes the following steps:

1) comparison of alpha-shares—determined by means of a method according to invention corresponding to a reference value and/or an average value as found out in reference samples. A reference sample can be that of a healthy person or of other patients suffering or not suffering from the disorder tested for. Instead of actual reference samples previously established referential values can be applied as well;
2) quantification of misfolded proteins
3) comparison of the concentration of misfolded proteins or one specific misfolded protein of misfolded proteins which hold specific groups of chemical reaction in concentrations which were previously quantified with the same proband;
4) In some cases it may be useful to calculate the ratio of the concentration in misfoldings with a specifically tested protein by forming the quotient of concentration in one specifically tested protein and the concentration of the same-self protein when misfolded.

One further performance of invention is the targeted searching for convenient candidates among the misfolded proteins/peptides for diagnostic purposes as to diseases by means of the binding substances as disclosed here.

To achieve that aim at least one of the binding substances for misfolded proteins—as disclosed in this report of invention—will be immobilized to a solid surface, as described above. The coated material will then be incubated by a body fluid (see above) or a tissue abstract of patients suffering from the disease and require a method of identifying a specific misfolded protein/peptide as well as by comparison samples of healthy probands and specific bound proteins/peptides will be analysed and identified by means of common methods of proteomics. These include e.g., 2D-gel-electrophoesis Western blotting, immunoprecipitation, partial proteolysis and mass spectrometry of the fission products. Suitable misfolded candidates among the proteins/peptides for the arrangement of specific test methods as to specific diseases or their various formations/medical conditions are those that show a significantly higher concentration in the body fluid of the patients than in the body fluid of the control groups.

The method of detecting and quantifying misfolded proteins can—according to invention—also be applied in order to search in body fluids or tissue of apparently healthy probands for indicators of an early still pre-symptomatic or asymptomatic preliminary stage. In this respect a favored performance of our invention is to be seen e.g. in the detection and quantification of amyloid beta-oligomeres even before a loss of memory becomes obvious or in another case the detection and quantification of HOCl-modified proteins, misfolded fibrinogen, misfolded albumin, misfolded ceruloplasmin or of electronegative LDL (LDL(−)), before consequences of the arteriosclerosis through angina pectoris, TIA, stroke, myocardial infarction or peripheral vascular obliteration become obvious, or as to misfolded serpins, alpha1 antitrypsin in particular, before the clinical symptoms will lead to preeclampsia prior to being diagnosed or of misfolded proteins of that group of proteins which cause classic amyloidosis before inducing amyloid deposition.

The tasks of the disclosed invention will furthermore be solved at large by a diagnostic kit, which holds a least one of the binding substances for misfolded proteins/peptides.

Such a kit according to invention will have to meet with very specific requirements. All reagents used in this procedure have themselves to be absolutely free of misfolded proteins/peptides.

A reagent according to this invention is a bio-molecule used in an assay for detecting misfolded proteins,—a molecule that may undergo procedures that induce misfoldings of proteins/peptides, e.g. it may be effected by a buffer component, a stabilizing protein, a component for coating for blocking non-specific binders of the solid phase such as—but not limited to—bovine serum albumin, human serum albumin, skim milk powder, reagents used during production of the solid phase, an identifying reagent in particular if it is an antibody or some other protein—especially a recombinant protein. Only those reagents can be used that are absolutely or, at least almost, free of misfolded proteins/peptides.

The term solid phase materials and solid phase material components is used to describe solid phases or substrate that as a matter of routine are usually used in binding assays. With our current invention the term describes a method of production of a solid phase, and supporting reagents such as a blockage and identification reagent that is free of misfolded proteins/peptides, and methods of coating the solid phase component with a specific binding partner that is free of misfolded proteins/peptides and the washing out of the solid body component and the adding of a blocking or stabilizing solution which in itself is free of misfolded proteins/peptides and using an identification reagent/a binding-pair factor which is also free of misfolded proteins/peptides. Particular attention should furthermore be paid when using avidin, streptavidin, bovine serum albumin, albumin from humans, skim milk powder, as well as any kind of antibodies and identifying enzymes.

In one specific performance of our invention at least one of the here-disclosed binding substances for misfolded proteins/peptides will be immobilised at a sensor-chip for quantifying of Plasmon resonance in a miniature flow cell. Body liquids or diluted body fluids or tissue abstracts which may potentially hold misfolded proteins/peptides and thus interactive partners for the binding substances will be washed across the surface of this sensor-chip and interactions with the immobilised molecules get detected by way of an alteration of the index of refraction. Time-related alterations of the refractive index are registered and serve as determinators of kinetic parameters.

Misfolded extracellular proteins/peptides in the body form complexes with so-called extracellular chaperones. Among these are alpha2 macroglobulin, haptoglobin, and clusterin[102].

According to invention such complexes can be detected and quantified by means of a sandwich assay with which one of the two binding partners will be a binding substance for misfolded proteins/peptides as disclosed in this patent application or a so far notable binding substance such as t-PA, FXII, HGFa, fibronectin and the other binding partner will be a specific binding partner for the so-called extracellular chaperone such as a monoclonal antibody against alpha2 macroglobulins, a monoclonal antibody against clusterin or a monoclonal antibody against haptoglobin A favored performance of the invention is the detection and quantification of misfolded macroglobulins complexes alongside with other proteins by means of devices/binding substances and methods as disclosed in this invention disclosure. This is particularly suitable for diagnosing tumor diseases.

2. Therapeutic Monitoring and -Surveyance

One particularly preferential performance of the invention lies in the use of ADAM15 (trimetazidine), of the metalloprotease domain thereof and in particular of the peptides holding the sequence His, Trp (tryptophan), Arg, Arg, Ala, His, Leu, Leu, Pro, Arg, Leu, Pro (HWRRAHLLPRLP), the Sequence Glu, Asn, Phe, Leu, His, Trp, Arg, Arg, Ala, His, Leu, Leu (GNFLHWRRAHLL) or hold or include the sequence Ala, Val, Thr, Leu, Glu, Asn, Phe, Leu, His, Trp, Arg, Arg, or His, Trp, Arg, Arg, Pro or His, Trp, Arg, Arg (HWRR) and of the Kringel 5 domain of plasminogen and specifically of the amino acid sequences PRKLYDY or of amino acid sequences which present the sequence PRKLYDY for detection an quantification of misfolded proteins for the monitoring, surveying and controlling of pharmaceutical medication therapies. The term therapy control also includes the classification of patients in "responder and non-responder" related to a specific therapy or the course of therapy.

Misfolded proteins may activate thrombocytes via receptors CD36 and GPIb[103]. The activation of thrombocytes by misfolded proteins is independent of the generation of thromboxane A2 and the release of ADP. Both secondary agonists, however, increase the activation of thrombocytes through misfolded proteins as a feed-back reaction. Brodde and Kehrel have succeeded in showing that aspirin/ASS via inhibiting ATPase activity of the GRP78 also inhibits the activation of thrombocytes by misfolded proteins/peptides. Thus misfolded proteins/peptides can be specifically applied for monitoring the reaction of patients towards a therapy with ASS/aspirin.

Aspirin (synonym: acetylsalicylic acid (ASS)) is applied for the prevention of thrombotic, thromboembolic and specifically of cardiac-vascular incidents, inclusively stroke and peripheral vascular obliteration. Not all patients equally react to this medication. The phenomenon of the "aspirin non-responders" has been described at large and has been thoroughly looked into. The causes have not yet fully cleared up[104]. A poor reaction to aspirin after 24 hours is statistically related to inflammation markers, smoking and diabetes[105]. All these are reactions which in a body cause the misfolding of protein/peptides.

Interesting enough, a long-term aspirin therapy also provides some protection from solid tumors[106]. One of the most essential cellular receptors for extracellular misfolded proteins/peptides is GRP78/Bip. It rules such important procedures as the angiogenesis, autophagy and cellular proliferation.

Misfolded proteins can contribute to the "non-response" or to the underdosing with some patients by inducing the presentation of GRP78 on the surface of the thrombocytes. That pharmaceutical medication then is busy with the inhibition of the ATPase activity of the GRP78. So it is useful to detect and quantify the concentration of misfolded proteins/peptides in the blood of patients under aspirin medication.

According to invention a useful method would be as described above the method of detection and quantification of the whole amount of all misfolded proteins in blood or plasma such as Plasmon resonance measuring or a method of quantification in a sandwich procedure where the two binding substances applied are general binding partners for misfolded proteins/peptides and are therefore most likely to fulfil their task.

Also for pharmaceutical medication from the group of thienopyridines very divergent reactions have been observed which may be averse to a successful therapy[107].

HOCl-modified misfolded proteins/peptides furthermore interact through a reactive group—which on their part react to free SH-groups—directly to the active metabolites of the thienopyridines and thus have an impact on a thienopyridine-therapy such as clopidogrel and prasugrel. As the thiol groups of the active metabolites of the thienopyridines are essential for the inhibiting of P2Y12, free metabolites for inhibition of P2Y12 are available in a lower concentration. HOCl-modified misfolded proteins can catch the active metabolites of the thienopyridines and thus influence the aimful therapeutic inhibition of the ADP-induced thrombocyte-activation in a negative way (Brodde, Heptinstall, Kehrel; manuscript in progress).

The variety in reactions to clopidogrel among individual patients has been suspected of being due to the activity of paraoxonasis-1 in an enzyme in the HDL. Patients who were PON1 QQ192 homozygous ran a higher risk of stent-thromboses than PON1 RR192 homozygous patients. PON1 QQ192-homozygosity is related to a lower concentration of active metabolites of the clopidogrel and a lower level of inhibition of ADP-induced activity of platelets. The paraoxonase-1 is part of the bio-activating of clopidogrel. The enzyme gets inactivated by HOCl, acrolein and such reactive groups as proteins as have been altered by acrolein[109]. So HOCl-modified misfolded proteins are indeed very likely to be one cause of the poor reaction to pharmaceutical medication from the group of thienopyridines (clopidogrel, prasugrel, ticlopidin) as far as genetic disposition is not involved.

The quantification of HOCl-modified misfolded proteins/peptides, however, is also helpful because the afore-mentioned substances are very effective thrombocyte-activators which may entail thrombosis. As one of the groups responding to HOCl-modified misfolded proteins/peptides that on their part respond to free thiol groups, we have managed to identify FDP-lysine (N (epsilon)-(3-formyl-3,4-dehydropiperlidino)lysine on misfolded proteins. By means of specific commercially available monoclonal antibodies against this group such misfolded proteins/peptides as may effect therapy with thienopyridines can be detected and quantified in combination with binder substances for misfolded proteins/peptides. And also by combining a binder for misfolded proteins/peptides with detectors holding free SH-groups on their own part such misfolded proteins/peptides as effecting therapy with thienopyridines are quantifiable.

As one embodiment a reagent binding misfolded proteins/peptides—preferably a binder material according to invention but also a notably general binder such as a chaperone—in particular GRP78/BIP, t-PA, HGFA, fibronectin, FXII and others—gets immobilised to a solid surface and subsequently put in contact with a sample of blood, plasma or serum from a patient. Groups that bind to thiol can then be identified in various way such as by antibodies against FDP-lysine but also by detection reagents which in themselves hold free SH-groups like—but not limited to—reduced—glutathione-gold, reduced-glutathione-biotin alongside with an appropriate analysing system (see above).

By using a solid phase that holds free SH-groups like (but not limited to) microwell plates or beads to which glutathione has been immobilised—such as thermo-scientific pierce glutathione-coated plate, thermo-scientific pierce glutathione beads the sandwich assay can also be arranged vice versa. Many of such reagents are commercially available as having been designed for detection and/or purification of GST-marked recombinant proteins. So experts are familiar with their use.

The activation of thrombocytes by misfolded proteins/peptides may—as patent application DE 10 2010 043 733.6 describes—also be inhibited by plain pegylated liposomes have already been used in clinical research as a tool for transporting pharmaceutical medication. This justifies the assumption that pegylated liposomes themselves may be directly applied to mammals and humans. Detecting and quantifying methods of misfolded proteins/peptides can—according to invention—be applied for the monitoring of a therapy with pegylated liposomes to mammals—in particular animals used for pre-clinical research—as well as to humans.

In this context the same methods—according to invention—are suitable as those described earlier for the monitoring of aspirin in this patent application.

The activity of the secretory phospholiopase A2 (sPLA2) in patients' blood/plasma is a bio-marker for cardio-vascular disorders[110-114], the metabolic syndrome[115], and post-traumatic multiple organ failure[116,117]. The male gender, obesity and a high concentration of LDL cholesterol are statistically related to a high degree of sPLA2-activity, as has been evidenced in numerous surveys.

sPLA2-inhibitors such as varespladib methyl have been successfully used as a device in therapy surveys as to cardio-vascular diseases on the grounds of arteriosclerosis[118,119].

Among other functions SPLA can modify LDL in such a way that the latter becomes more atherogenic. The apolipoprotein B-100 in LDL gets altered and then displays a higher degree of affinity to glycosamini-glycans and proteo-glycanes. The close affinity to heparin glycosamini-glycans and proteo-glycans has been a frequently observed but yet rather unspecific phenomenon of misfolded proteins. Indeed does the calcium-dependent sPLA2 modify LDL into an electronegative LDL (LDL(-)); which distinctly holds misfolded protein as physicochemical methods, e.g. circular dichroism have clearly proved[120,121].

According to invention the task of therapy monitoring with sPLA2 inhibitors can be carried out by detecting and quantifying misfolded apolipoprotein B100. In an assay with two binder materials, one of which a substance with a high probability of recognizing apolipoprotein B-100, whereas the other binder is one of the binder materials for misfolded proteins/peptides, as disclosed in this patent application, or one of the other identified binding substances for misfolded proteins like (but not limited to) chaperones such as GRP78, tPA, HGFA, fibronectin, and FXII.

In a highly preferable performance of the invention one protein, polypeptide or peptide, as disclosed in this patent application, gets immobilized to a solid surface. Blood, plasma or serum of the patient or proband or of the mammal will be put into contact with that prepared surface so that misfolded proteins/peptides can dock at the binder substances. The identifying of apolipoprotein B100 among the bound proteins can be effected by means of a specific identification reagent for apolipoprotein B100 and a suitable identify system corresponding to those methods as described in the paragraph about diagnostics.

Extracellular misfolded proteins can dock at chaperones on the surface of cells. On stress-affected cells, particularly on tumour cells, endothelial cells, on monocytes, on smooth muscle cells, on cardiomyocytes, and many others GRP78/BIP has been discovered on their respective cellular surfaces.

This is supposed to be related to the reactivity of tumour cells to pharmaceutical chemotherapeutic medication[122].

As to the prostate carcinoma the extracellular prostate-specific antigen (PSA) has recently been found out to coalesce a complex with alpha2 macroglobulin and that this particular complex binds to GRP78 on the surface of the carcinoma cell. Misfolded alpha2 macroglobulin binds to GRP78 and sends a signal. That signal transmitted via GRP78 increases cell proliferation and migration of tumor cells and suppresses autophagy[123]. GRP78 receptors have been discovered on numerous tumour cells such as breast cancer, ovary carcinoma, liver and colon cancer, lung cancer and melanoma cells. Autoantibodies against GRP78 on melanoma cells promote tumor growth in mice[124]. So complexes from other proteins with misfolded alpha2 macroglobulins are also likely to play a vital part in the pathogenesis of yet more tumors.

GRP78 on the cellular surface has a share in the regulation of angiogenesis, endothelium proliferation, endothelium cellular migration, in attracting endothelial progenitor cells[125] for tissue repair and wound healing e.g. after coronary infarction[126] but also in tumour-neoangiogenesis[127]. Many of the substances having been used als inhibitors of angiogenesis in clinical surveys are themselves misfolded proteins/protein fragments/peptides[128].

The detection and quantification of misfolded proteins/peptides according to invention as well as the selection of one singular protein/peptide related to a specific disorder according to invention is therefore also useful for diagnostic and therapy monitoring purposes as to diseases which at present have not yet been assumed to be related to misfoldings of proteins/peptides such as a therapy for fostering or inhibiting of angiogenesis, chemotherapy against tumours or the therapy as to improve wound-healing of tissues and can be carried out by means of binder material for misfolded proteins/peptides as disclosed in our invention.

3. Segregation and Isolation of Misfolded Proteins/Peptides from the Bodies of an Animal or a Human Another type of achievement of our invention as is disclosed in this patent application is the use of the disclosed binders for misfolded proteins/peptide, i.e. ADAM15 (Metargidin), the metalloproteinase domain of ADAM15 and in particular peptides holding the sequence His, Arg, Arg, Ala, His, Leu, Leu, Pro, Arg, Leu, Pro (HWRRAHLLPRLP) corresponding to the ADAM15 sequences 286-297, the sequence Glu, Asn, Phe, Leu, His, Trp, Arg, Arg, Ala, His, Leu, Leu (ENFLHWRRAHLL) ADAM 15 sequences 282-293, or the sequence Ala, Val, Thr, Leu, Glu, Asn, Phe, Leu, His, Arg, Arg, ADAM15 sequences 278-289, His, Trp, Arg, Arg, Pro or His, Trp, Arg, Arg (HWRR) and the Kringel 5 domain of plasminogen and in particular the amino acid sequence PRKLYDY or amino acid sequences holding sequence PRKLYDY in order to remove misfolded proteins/peptides or to reduce the concentration of misfolded proteins/peptides.

Misfolded proteins/peptides hold a major share in the causes of many diseases. Therefore it may therapeutically make sense in some cases to withdraw misfolded proteins/peptides from the body; diseases as to which this may be helpful at the present stage of research might be e.g.—but not restricted to—Alzheimer's disease, disorders caused by prions such as Creutzfeld-Jakob disease, Gerstmann-Straussler-Scheinker syndrome, fatal familial insomnia Kuru; BSA, scrapie, neurodegenerative diseases such as Parkinson's disease, amylotrophic lateral sclerosis (ALS), familial encephalopathy with neuroserpin inclusion bodies, frontotemporal lobar degeneration with ubiquitin-proteasom system (FTLD-UPS), the large class of auto-immune deficiencies, rheumatic arthritis, inflammation diseases, multiple sclerosis, arteriosclerosis and its secondary diseases, infections in particular those with microorganisms which present misfolded proteins on their surfaces, sepsis, diabetes, wound healing disorders, preeclampsia, a disposition to bleedings, thrombosis, post-reanimation condition, post-hemodialysis condition, tumour diseases, amyloidoses such as AA amyloidoses, AL amyloidoses, AE amyloidoses, AB amyloidoses, AP amyloidoses, AS amyloidoses, and ATTR amyloidoses as well as cataract. The number of disorders which have been identified to be related to misfolded proteins/peptides has been growing lately.

In a very preferential performance of our invention the object of a procedure of removing or at least depleting misfolded proteins/peptides from the body fluids and in particular blood is either a mammal or a human.

The binder substances for misfolded proteins/peptides as disclosed in this invention will be immobilised to a solid base. This can e.g. be a substance which is well-tolerated by blood but in itself does not produce any misfoldings of proteins/peptides such as material for extracorporeal dialysis, a filter, a membrane, beads the inner surface of hose systems or similar. Blood from the animal or human patient will then flow across the immobilised binders so that the latter can then bind and catch the misfolded proteins/peptides. The blood then depleted of misfolded proteins/peptides will flow back into the body and can be further depleted of misfolded proteins/peptides in further repetitious steps. In other performances of our invention the patient's blood will be put into contact with the binder according to invention, a binder that is fixed to a solid surface so that the blood is immobilized. This blood will then be depleted of misfolded proteins/peptides by removal of the solid phase. This can be effected in various ways, e.g.—but not exclusively restricted to—simple drawing out of a coated membrane or a filter, the removal of magnetic beads by applying a magnet, etc. The blood depleted of misfolded proteins will then be returned to the patient's body.

By quantifying the concentration of misfolded proteins/peptide before and after the procedure by means of applying a method as described in this patent application and to be found in the paragraphs about diagnostics the success of this method can be assessed and recorded. In addition to blood also other body fluids can be depleted of misfolded proteins/peptides.

4. Detection, Segregation and Isolation of Misfolded Proteins/Peptides in/from Pharmaceutical Medication, their Additives and Pharmaceutical Compositions Inside/from Reagents and Supportive Reagents for Diagnostic Tests, Inside/from Research Reagents and in/from Foods and Liquids as Well as Control of Production Procedures and/or Procedures while Storage of Pharmaceutical Medication, their Additives, Reagents and Supporting Reagents for Diagnostic Test Purposes, Research Reagents and Bio-Films a) Pharmaceutical Medications, Pharmaceutical Additives, and Pharmaceutical Compositions The market for medications which contain proteins or peptides, especially products of blood or antibody-based therapeutics and other medications produced with recombinant methods has become a rapidly growing market.

One big problem in the production of recombinant proteins/peptides but also when using the proteins/peptides of organic material such as blood, plasma, or serum lies in the destabilization of that protein/peptide which then will induce misfoldings. This can happen at all stages of production e.g. in the cell culture, in the initial material, during cleansing procedures and by virus inactivation as well as in chemical formulation, storage in trade and when actually applied. One basic reason is the fact that proteins/peptides in non-hosting organisms get expressed and the concentration of the expressed proteins/peptides is rather high and the cellular material used for synthesis submitted to stress. In the cleansing procedure of the proteins/peptides there is a lack of natural associated material such as lipids, lipoproteins, and other proteins which in their natural surroundings stabilise the produced proteins/peptides. Some of the recombinant proteins/peptides are even cleaned up from inclusion bodies which have formed within the expressed organisms from misfolded protein/peptide, as inclusion bodies are easily separable from cellular material. Such proteins/peptides will then have to be returned into reasonably native conformation.

In the cleansing procedure further conditions will induce misfoldings. So some of the shear stress, dissolvents, detergents, ph-value, temperature, freezing and defrosting, and surface material the target protein is put in contact with, ionic strength, passages from one boundary layer to the next such as the boundary between air and fluids, lyophilization, cold, heat, pressure, irradiation (UV, IR, X-rays), "vortexes", "ultrasonics", stirring, shaking, high concentrations in protein and as well as chemical mutations have an impact on the stability of native protein/peptide conformation. Chemical modifications are e.g. proteolytic cleavage, oxidation, carbamylation, beta-elimination, racemization, deamidation, acylation of the produced or cleansed target protein. Cystein-containing proteins can form disulfide bridges. Especially globular proteins are rather instable in aqueous solutions and have a disposition to misfoldings and subsequent aggregation. Such proteins can precipitate and block chromatographic columns and filters. Misfolding in target proteins induces in many cases loss in activity and so reduction of the specific activity of a pharmaceutical medication. The mechanisms described can effect target proteins/peptides as well as associated proteins/peptides. Affinity chromatography uses specific interactions between the protein/peptide to be cleansed and its immobilised ligand. Elution conditions are often rather harsh. Ion exchange chromatography or hydrophobic interaction chromatography also cause stress for the protein-conformation.

The storage of pharmaceutical medication holding proteins or peptides as agents or additives can also induce misfoldings in the ingredients by physical and chemical processes.

Pharmaceutical medications originated in materials which have been obtained from animal or human bodies can contain misfolded proteins/peptides even through initial material, especially if the donator thereof suffers from one of the many disorders that go along with protein misfoldings and in particular if the disease has not yet become apparent and thus has neither been suspected by the patient nor by the doctor.

Among the medications holding proteins/peptides as agents or additives there are e.g., antibodies, vaccines, coagulation pharmaceuticals washed out of blood, hormones, cytokines, and growth factors, blood bank products such as plasma and cellular concentrates, recombinant proteins as immunosuppressive medication, recombinant proteins as anti-rheumatics and anti-inflammatory agents, recombinant proteins for osteoporosis, recombinant proteins as anti-rheumatics and anti-inflammatory agents, recombinant proteins with cancer, recombinant proteins to regulate blood coagulation, recombinant proteins with diabetes, recombinant and synthetic hypophysis and hypothalamus hormones, recombinant proteins to manipulate blood cell formation, recombinant proteins for wound-healing and psoriasis. Many of these products contain another protein for stabilizing such as albumin of human origin.

Changes in medications depending on storage can induce a significant impairment. Just one of the many examples is a blood bank pharmaceutical. Koch et al. describe that erythrocyte-concentrates can deteriorate in their effects during storage[129]. On the other hand destroying such medications after short-term storage cannot be an appropriate solution to the problem especially considering the shortage of such important medications. To find a method which allows to elicit those erythrocyte medication with poor results and undesirable side effect as described in the survey quoted here would be a big progress in medical science.

Medications containing proteins/peptides can also cause health disorders. As such have been described e.g. anaphylactic reactions, fever, hemostasis disorders, fibrinolysis, disseminated intravascular coagulation (DIC), thromboses, and (auto)antibodies. The byeffects as described here often depend on batches and also on the health condition of the patient, to whom these pharmaceuticals are administered. As misfoldings of proteins/peptides are directly related to changes in immune defense, antibodies and disorders of hemostasis/fibrinolysis misfolded proteins/peptides are very likely to play a major part in the pharmaceuticals or the additives thereof as to the decrease of product quality and the appearance of undesirable side-effects.

Hermeling et al describe the connection between the folding of a protein/peptide and its immunogenicity[130] Rosenberg reports that pharmaceutical medications containing oxidated or aggregated proteins are more immuno-genic[131]. Joubert et al describe an activation of the innate immune response by aggregated proteins in pharmaceutical medication[132].

Misfolding of proteins/peptides in medication can influence product quality and efficiency unfavorably[133].

Therefore methods are required which indicate such alterations[134-138].

The detection of aggregates, a performance of misfolded proteins/peptides has become a standard feature in pharmaceutical biotechnology. By means of methods monitoring the formation of aggregates production procedures get modified and optimised. Among these methods there are the rather lengthy physical methods such as analytic techniques: "dynamic light scattering (DLS)", multi-angle light laser scattering (MALLS), UV-spectroscopy, "light obscuration", "micro-flow imaging (MFI)", "nano particle tracking analysis (NTA)", and separation devices such as "size exclusion chromatography (SEC)", "field flow fractionation", "capillary electrophoresis (CE)" or analytical ultracentrifuge[139].

Another performance according to invention is the detecting of misfolded proteins/peptides even independent of their aggregation and thus optimizing the whole production process (see above) and thereby increasing the yields of pharmaceutical medication for the producer and improving the quality of that medication for the patient.

The target is to produce no more than just the inevitable minimum of misfolded proteins/peptides in the whole of the production process and/or to leave in medications.

By means of the binder substances according to invention misfolded proteins/peptides in the various steps of production and in the pharmaceutical medications can easily and quickly be detected. The method is applied in analogy to the method described in the paragraphs about diagnostics. However, instead of a body fluid sample a sample of the substance in any random step of production such as—but not limited to—the initial material, the cell culture, one of the cleansing methods, methods of virus-activation, formulation, storage, transport, trade, handling on the part of the consumer will be tested for misfolded proteins/peptides and recorded. A convenient testing method is, e.g. the microtiter-plate assay including the binder substance according to invention, but also Plasmon resonance, bead assay, turbimetry and many others which are a household number to the expert.

Elimination or depletion of misfolded proteins/peptides from production steps of pharmaceutical medications can—according to invention—be applied by immobilizing ADAM15 (Metargidin), the metalloproteinase domain of ADAM15 and in particular peptides holding the sequence His, Trp, Arg, Arg, Ala, His, Leu, Leu, Pro, Arg, Leu, Pro (HWRRAHLLPRLP) corresponding to ADAM15 sequences 286-297, His, Trp, Arg, Arg, Pro or His, Trp, Arg, Arg (HWRR) as well as the Kringel 5 domain of plasminogen and specifically the amino acid sequence PRKLYDY or amino acid sequences including sequence PRKLYDY will be immobilised to a solid surface. This may preferably be a filter system, a membrane, a hose system or a matrix as usually chosen for affinity-chromatography. The segregation of the misfolded proteins/peptides will be carried out in analogy to the method as described earlier about the depletion of misfolded proteins/peptides from body fluids—i.e. by means of having bound the misfolded proteins/peptides from the production materials or from the finished medication to the coated matrix and then separating the solubilised medication which then will contain a much lower concentration of misfolded proteins/peptides or will then contain none at all.

When—according to invention—the above-mentioned peptides are preferably used, the misfolded protein/peptide material can easily be eluted in a further step as a surplus of free peptide. This may come in useful for later analyses of the misfolded material which can be used for modification and optimization of the production procedures.

b) Reagents and Supportive Reagents for Diagnostic Tests

The invention also refers to methods of selection and/or quality control of reagents or coated solid phase components which are equally suitable for all analyses and assays for examining misfolded proteins.

A method or a kit for detection and quantification of misfolded proteins/peptides have to comply with specific requirements according to invention.

A commercially and/or appropriate assay requires among other features that results achieved by means of such assays are reproducible from laboratory to laboratory as well as to the procedure as a whole. Reagent- and kit-stability during delivery and/or storage are vital criteria for a safe method serving as a routine examination of assays for misfolded proteins/peptides.

Using reagents which themselves contain misfolded proteins leads to high variability among the batches, highly incalculable background reactions and poor kit-stability. Especially the stability of the solid phase component as used in the assays for misfolded proteins is extremely complex and crucial.

One particularly favorable performance of our invention is a range of methods using—according to invention—the binder substances for misfolded proteins/peptides which are applied in order to chose such reagents, or in particular solid phase components, for binding assays to identify misfolded proteins/peptides which are suitable for such binding assays in terms of identifying misfolded proteins/peptides, which are furthermore themselves free of misfolded proteins/peptides or in which such misfolded proteins/peptides occur in very low quantities and which can on those grounds be used in those assays for detecting and quantifying misfolded proteins/peptides.

A reagent—according to the presented invention—is a bio-molecule used in an assay for detecting misfolded proteins—a bio-molecule which may undergo procedures which may induce misfoldings in proteins/peptides, e.g. of a buffer component, a stabilizing protein, a component for coating or for the blocking of non-specific binders of the solid phase such as—but not limited to—bovine serum albumin, human albumin, skim milk powder, reagents used for reagents in the production process of the solid phase, an identifying reagent in particular when being an antibody or any other protein but especially if the latter happens to be a recombinant protein. Only proteins/peptides free of misfoldings or reagents at least essentially free of misfolded proteins/peptides will be selected and used.

The term solid phase materials/-component is used to describe solid phases or basic materials which are to be—as a routine—used in binding assays. As to the invention presented here a method will be described how to produce a solid phase component and supportive reagents such as blocking and identifying reagents free of misfolded proteins/peptides; the coating of the solid phase component with a specific binding partner which is also free of misfolded proteins/peptides; the washing out of the solid-body component and the adding of a blocking or a stabilizing solution which has to be free from misfolded proteins/peptides; the use of an identifying reagent/binding-pair partner which is also free of misfolded proteins/peptides. Particular attention should be paid to the use of avidin, streptavidin, bovine serum albumin, human albumin, skim milk powder, any type of antibodies and identification enzymes.

The application of the invention in terms of our invention is not restricted to reagents which are used in diagnostic tests for detection and quantification of misfolded proteins. On the contrary it is of general advantage in diagnostic tests in which proteins or peptides are applied that there are no misfolded proteins/peptides in these reagents as these may result in unspecific reactions and thus will unfavourably influence test results.

By means of bind substances according to invention misfolded proteins/peptides in the various production steps and in the diagnostic reagent can be simply and easily detected. The procedure is carried out in analogy to the method as described in the paragraph about diagnostics. Instead of a body fluid test substance one such can be chosen from any random production step like—but not restricted to—the initial material, cell culture, one of the cleansing procedures, virus-activating method, formulating, storage, transport, trade, and eventually the handling by the consumer or the diadnostic reagent itself—they all can be tested and this may be recorded. Adequate test methods are e.g. microtiter plate assay including the use of binder substances according to invention but also Plasmon resonance, bead-assay, turbimetry and many other methods that a common to the expert.

Elimination or depletion of misfolded proteins/peptides from production steps of the reagent for a diagnostic procedure or a diagnostic kit can—according to invention—also be carried out by a method as to which ADAM15 (Metargidin), the metalloprotease domain of ADAM15 and in particular peptides holding the sequence His, Trp, Arg, Arg, Ala, His, Leu, Leu, Pro, Arg, Leu, Pro (HWRRAHLLPRLP) corresponding to ADAM15 sequences 286-297, the sequence Glu, Asn, Phe, Leu, His, Trp, Arg, Arg, Ala, His, Leu, Leu (ENFLHWRRAHLL) ADAM 15 sequences 282-293, or the sequence Ala, Val, Thr, Leu, Glu, Asn, Phe, Leu, His, Trp, Arg, Arg ADAM15 sequence 278-289, His, Trp, Arg, Arg, Pro or His, Trp, Arg, Arg (HWRR) as well as the Kringel 5 domain of plasminogen and particularly the amino acid sequence PRKLYDY or such amino acid sequences as holding sequence PRKLYDY gets immobilized to a solid surface. This may preferably be a filter system, a membrane, a hose system or a matrix as they are usually applied for affinity-chromatography.

The segregation of misfolded proteins/peptides is to be carried out in analogy to the method referring to depletion of misfolded proteins/peptides from body fluids, by means of binding the misfolded proteins/peptides from the material of the various production steps of the medication or from the finished medication to the coated matrix and then separating the medication in soluble form which will subsequently show a lower level of concentration of misfolded proteins/peptides or none at all.

c) Research Reagents

In all scientific surveys concerning research as well as in all surveys for finding or testing therapeutics and diagnostics where other proteins are involved such as receptors to which misfolded proteins/peptides can bind or as to which the test reagents themselves are misfolded proteins/peptides it is indispensible for the true understanding of the achieved results that the accompanying reagents by which term reagents or additives are meant which themselves are not central to research, e.g. as is particularly true for cellular culture media, cellular culture media additives, and in particular serums from mammals like fetal calf serum, reagents for stabilizing proteins and here in particular additives like albumin, bovine serum albumin, skim milk powder, must not contain misfolded proteins. This is particularly important, if for the experiment a binder or the effect of a binder from one test substance to another protein is to be tested, one that is able to recognise misfolded proteins/peptides.

It is furthermore of vital interest in the understanding of research findings to the researcher to know, if one of the reaction partners is a misfolded protein/peptide.

Such a selection of suitable reagents or solid phase components is—according to invention—particularly essential for tests or screening of medications as well as testing as to the fields of fibrinolysis, tPA, plasminogen, activating contact phases, FXII, chaperones, phagocytes, apoptosis, cell proliferation, wound-healing, amyloidoses, effect of ADAMs, growth factors, extracellular matrix, infection, inflammation, ischemia, ischemia-reperfusion damage, rheumatism, quantification of auto-antibodies, generating of auto-antibodies, vaccine, coagulation, generating of antibodies, innate and adaptive defense, arteriosclerosis, neurodegenerative disorders, sepsis, multiple organ failure, biomarkers, biocompatibility of materials, reaction of tumours to chemotherapeutic medication, angiogenesis, neo-angiogenesis, shedding of superfacial proteins, quantification of segregated proteins/peptides, and generally speaking of all research on recombinant proteins as well as on microorganisms.

The invention presented here therefore is in a further performance also a method for selection and/or quality control of a research reagent and for removal of misfolded proteins from research reagents.

By means of the binder substances—according to invention—misfolded proteins/peptides can quickly and easily be detected. The procedure is carried out in analogy to the method as described in the paragraph about diagnostics. Instead of a body fluid as test substance, however, a substance sample from any random production step like—but not restricted to—the initial material, cell culture, one of the cleansing procedures, virus-inactivation procedures, formulation, storage, transport, trade, handling on the part of the consumer) of a research reagent or the research agent itself is to be screened for misfolded proteins/peptides and recorded thereafter. As testing method microtiter-plate assay has proved to be suitable using a binder substance according to invention, but also Plasmon resonance, bead-assay, turbimetry and many others as have been common to the expert. The method is also suitable for optimizing the stability of a research reagent and for testing the impact of storage conditions.

Elimination or depletion of misfolded proteins/peptides from production steps of the generating of the research reagent or of one preliminary stage of production can—according to invention—be carried out by a method that allows ADAM15 (Metargidin), the metalloprotease domain of ADAM15 and in particular peptides holding the sequence His, Trp, Arg, Arg, Ala, His, Leu, Leu, Pro, Arg, Leu, Pro (HWRRAHLLPRLP) corresponding to ADAM15 sequences 286-297, the sequence Glu, Asn, Phe, Leu, His, Trp, Arg, Arg, Ala, His, Leu, Leu (ENFLHWRRAHLL) ADAM 15 sequences 282-293, or the sequence Ala, Val, Thr, Leu, Glu, Asn, Phe, Leu, His, Trp, Arg, Arg ADAM15 sequences 278-289, His, Trp, Arg, Arg, Pro or His, Trp, Arg, Arg (HWRR) as well as the Kringel 5 domain of plasminogen and in particular the amino acid sequence PRKLYDY or amino acid sequences holding the sequence PRKLYDY to immobilise to a solid surface. This can be effected preferably by a filter system, a membrane, a hose system or a matrix as they are generally used for affinity-chromatography.

The segregation of misfolded proteins/peptides is to be carried out in analogy to the method described above about the depletion of misfolded proteins/peptides from body fluids; in this procedure misfolded proteins/peptides from the material of the production of the pharmaceutical medication or from the finished pharmaceutical are made to bind to the coated matrix and then the medication in soluble form which subsequently has a lower concentration of misfolded proteins/peptides or none at all is separated from the solid matrix.

d) Bio-Films

Bio-films develop when microorganisms like bacteria, algae, monads, fungi settle on boundary sites. They consist of a thin slimy, extracellular basic substance from polymers, in which microorganisms are embedded and they preferably develop in aqueous systems either on the surface of the liquid or in a boundary site to a solid phase[140]. They are to be found practically everywhere there is life possible for microorganisms, e.g. on nutrient-rich, flowing or on ponding water, in rivers, brooklets, lakes, on the surface of teeth, dentures, lenses and contact lenses, on foods, on materials to be administered within the body such as catheters, implants on surgical instruments, on domestic installations, and on groceries and on drink and tobacco. They can considerably contribute to the impairment of human and animal life, e.g.—but not restricted to—through infection and reduction of durability of foods[141]. If e.g. foods display visible films or smells develop through bio-films, it will be too late for suitable methods such as monitoring of cooling systems to keep the proliferation of microorganisms at bay.

Therefore it is important to develop sensors and methods of detection and quantification of bio-films within a narrow frame of time. Misfolded proteins can as described above aggregate as amyloids. Amyloid adhesion proteins have been found in large quantities in natural bio-films[142]. Thus bio-films contain misfolded proteins/protein fragments/peptides.

The binding substances—according to invention—can be linked to an identifying system and serve as sensors for bio-films.

A further performance of our invention is therefore the detection and quantification of bio-films by means of a method which uses a binder substance for misfolded proteins/peptides. This binder is to be preferably ADAM15 (Metargidin), the metalloprotease domain of ADAM15 and in particular peptides holding the sequence His, Trp, Arg, Arg, Ala, His, Leu, Leu, Pro, Arg, Leu, Pro (HWRRAHLLPRLP) corresponding to the ADAM15 sequences 286-297, the sequence Glu, Asn, Phe, Leu, His, Trp, Arg, Arg, Ala, His, Leu, Leu (ENFLHWRRAHLL) ADAM 15 sequences 282-293 or the sequence Ala, Val, Thr, Leu, Glu, Asn, Phe, Leu, His, Trp, Arg, Arg ADAM15 sequences 278-289, His, Trp, Arg, Arg, Pro or His, Trp, Arg, Arg (HWRR) as well as the Kringel 5 domain of plasminogen and in particular the amino acid sequence PRKLYDY or amino acid sequences including the sequence PRKLYDY.

An additional performance of the invention is the use of the above-described identification methods for assessing health risks as well as the qualification of hygiene- and quality failure, favourably in the field of health care, food processing, food storage and food trade.

5. Detection and Quantification of Misfolded Proteins/Peptides for Research Purposes as to Biological Tolerance and Bio-/Hemo-Compatibility of Materials and for Research on the Influence of Pharmaceutical Medications on the Production of Misfolded Proteins/Peptides. Application of that Method to Optimise Pharmaceutical Medication Particularly demanding requirements have to be imposed on materials which are put in contact with blood, plasma or tissue. They have to be biologically tolerant and bio-compatible. If they are to be in short-term, long-term or permanent contact with blood, they also have to be hemo-compatible; are they meant to be in contact with cells and tissue, they have to be cyto-compatible. The term bio-compatibility—according to invention—means the compatibility of materials with tissue of living creatures (bones, soft tissue, blood) from humans and animals. The material should be as inert as possible and not lead to decomposition or rejection and should as little as possible effect the metabolic system. Williams defined this in 2003, translated into German: The bio-compatibility of a medication for the long-term application relates to the quality of the product to carry out the targeted function at the desired degree of integration into the organism without causing there any undesirable local or systemic effect[143].

As to materials which are in short-term, long-term or permanent contact with blood very special requirements are to be complied with. Should the porous inside walls of artificial blood vessels allow for being sealed up by small-lump, microporous particles, the inner surface of artificial blood vessels, however, must not be thrombogenic as this may lead to thrombotic obliteration of the artificial or some natural vessel into which a thrombotic embolus may be carried. Heart valves and cardio-supportive systems on the one hand should not alter blood consistency so that internal bleedings might be avoided nor that thromboses may occur on the other hand.

Among the materials which can get into contact with blood we find e.g. a wide range of synthetic materials such as polyethylene, polypropylene, polyvinylchloride, polyester, polystyrene, polyurethane, silicon, polysulphone, polyamide, polytetrafluoroethylen, etc. but equally the derivates thereof and also ceramic devices as well as metal materials like stainless steel, titan, and their alloys.

Examples for therapeutical medication which get into short-term blood contact are catheters, artherectomy devices, blood monitors, guide wire, intravascular endoscope, intravascular ultrasonics, intravascular laser systems, retrograde coronary perfusion-catheter, heart-lung machine, circulatory devices, extracorporeal membrane-oxygenators, blood-dialysis and hemofiltration devices, dispensers, therapeutic apheresis devices, devices for absorption of specific substances from blood, interventional cardiology and vascular devices, percutaneous circulatory supporting systems, etc. Long-term and life-time devices as may be put into blood contact can be e.g. annuloplasty ring, prosthetic or bio-tissue/blood vessel implant, circulatory supportive systems (ventricular intra-aortic balloon pump), vena-cava interior filter, embolization devices, endovascular implants, implantable defibrillators and cardio converters, stents, vessel prosthesis, arterio-venous shunts, blood monitors, internal catheters for administering medications, artificial pacemaker-cords, intravascular membrane-oxygenators (artificial lung), leucocyte removal filter, and artificial heart valve.

According to ISO 10993-4 (DIN EN ISO 10993: Biological assessment of therapeutic medication products, Deutsches Institut für Normung, 2003) medical products as designed for contact with blood often have to be put to several tests from the following list: thrombosis, coagulation, thrombocytes, hematology, complementary supportive systems.

Usually the following simple tests have been carried out:
Thrombosis:
  thrombocyte adhesion and aggregation,
  adhering thrombocytes, fibrin, morphology of thrombocytes (light microscopy, scanning electron microscopy)
Coagulation:
  non-activated partial thromboplastin time, thrombocytes thrombin generating (TAT)
  D-Dimer
Thrombocytes: num quantification of thrombocytes (differential hemogram)
  thrombocyte-adhesion
  platelet factor 4 (PF4)
Hematology:
  num. quantification of leucocytes (differential hemogram)
  hemolysis with direct blood contact
  hemolysis with indirect blood contact
Complement System:
  complement factor C5a All these methods measure some of the effects a material can produce, but they actually offer little help in terms of selecting and optimizing bio-materials, as they do not get to the core of hemo-incompatibility.

To find suitable materials that are fully hemo-compatible for medical products is still one of the major problems we have to cope with[144].

In the interest of the patient's well-being there is an urgent need to optimise the pre-clinical evaluation-strategy of "medical devices" in blood contact. The problem in developing more biocompatible materials is that we have very little reliable features of the pathways of activating procedures.

To solve that problem we have to develop methods and sensors that are quick, uncomplicated, and reliable because they would have to start at the root of activating mechanisms.

Such a sensorial device is provided by the binder substances for misfolded proteins as presented in our invention.

As to the fostering or inhibiting of changes in blood so that a disposition either towards bleeding or towards thrombosis is effected on the patient, the protein-adsorption respectively interactions of proteins among their own kind and with the surfaces of the various materials play a decisive part. The quantity of protein-adsorption and the quality of interaction are furthermore effected by rheological features such as the velocity of flow, hematocrit, boundary transitions and the appearance of shearforce.

The complexity of procedures as to protein-adsorption and the interaction with the material are initial factors for coagulation and induce the activating of FXII and morphological changes of thrombocytes as has been observed so far[145].

Adsorption and denaturing of proteins on materials is therefore considered to be the measuring key to their biocompatibility. Until now that measuring has to be carried out in an elaborate way, such as the step-by-step analysis in the course of which proteins that are tagged to the material on the surface of test items are quantified and identified by means of enzyme-linked immunosorbent assay (ELISA), as has been described by Merrit et al.[146].

Specific proteins tagged to the surface of the material can be visualised by means of specific antibodies that are linked to an identifying system. Furthermore ellipsometry has been applied for the assessment of a layer of proteins on the surface of materials. For this optical measuring method linear polarized light is reflected by the material surface to be scrutinized and can then be quantified through a photo-detector. For identification purposes the adsorbed proteins can be detached and then identified by means of SDS-PAGE and Western blotting. Adsorbed proteins can, however, also be analysed by electron microscopic device.

But even with all these rather laborious, technically demanding and furthermore time consuming methods at hand there is one of the most essential parameters for bio-/hemo-compatibility of the material is still left aside: the quality of the material to induce misfoldings in adsorbed proteins.

Misfolded proteins activate, as described above, directly via FXII the kallikrein-system, they also influence via t-PA and plasminogen the fibrinolysis and they activate thrombocytes. Activated thrombocytes subsequently activate leucocytes and lymphocytes. Misfolded proteins/peptides are thus to be considered as adhesion-bridges for microorganisms and misfolded proteins/peptides play via their cell receptors a vital part among others in such essential processes a cell proliferation, apoptosis, autophagy, cellular migration, and immune defense.

The analysis of the problem whether a material generates misfoldings in adsorbed proteins or peptides is therefore an essential method for assessing the bio- and in particular the hemocompatibility.

According to invention the analysis of the bio- and in particular of the hemocompatibility can be carried out through devices which bind to misfolded proteins/peptides. This may be one of those proteins which by others have been described as general binder proteins for misfolded proteins/peptides, such as a chaperone, favourably GRP78/BIP, or tPA, or fibronectin, or HGFA, and very favourably it is a binder substance, according to the invention presented herewith, holding ADAM15 (Metargidin), the metalloprotease domain of ADAM15 and in particular peptides holding the sequence His, Trp, Arg, Arg, Ala, His, Leu, Leu, Pro, Arg, Leu, Pro (HWRRAHLLPRLP) corresponding to the ADAM15 sequences 286-297, the sequence Glu, Asn, Phe, Leu, His Trp, Arg, Arg, Ala, His, Leu, Leu (ENFLHWRRAHLL) ADAM 15 sequences 282-293 or the sequence Ala, Val, Thr, Leu, Glu, Asn, Phe, Leu, His, Trp, Arg, Arg ADAM15 sequences 278-289, His, Trp, Arg, Arg, Pro or His, Trp, Arg, Arg (HWRR) as well as the Kringel 5 domain of the plasminogen and in particular the amino acid sequence PRKLYDY or amino acid sequences including the sequence PRKLYDY.

The material to be analysed e.g. as sample bodies, sample platelets, sample beads or the medical product to be analysed will here be put into contact with a protein-/peptide solution, favourably a body fluid of an animal or human, in particular favourably with blood or plasma. According to invention it is recommendable to do so under static as well as—in a second test—under dynamic conditions.

The non-adsorbed material will be carefully washed out by means of suitable liquids such as—but not restricted to—physiologic saline solution or physiologic buffered solution. A binder substance which identifies misfolded proteins/peptides directly or indirectly, as dependent on an identifying system, binds to the misfolded protein/peptide and detects and quantifies misfolded proteins on the material surface to be analysed.

Misfolded protein can then be detected and quantified, e.g. fluorimetrically (flow cytometry on beads, fluorescence in plate systems), fluorescence-microscopically, electron-microscopically, enzymatically, by means of administering colorimetric substrates or chemiluminescence, turbidometrically or through any other random method that is common to the expert.

Identifying Reagent and Method of Analysis for Examining the Impact of a Medical Product on the Generating of Misfoldings in Proteins/Peptides An intensely preferable performance of the invention is an identifying reagent and a method of analysing the impact of a medical product—favorably one of an extracorporeal system which is put into contact with circulating blood or of an implant or part thereof, especially preferable of an extra- or intra-corporeal supportive system, heart valves, tissue prostheses or stents on the generating of protein/peptide misfoldings in proteins/peptides in fluid. These fluids are, if particularly favored, body fluids of humans or animals, and especially favored if they are blood or plasma of humans or animals.

As there are many more qualities like—but not restricted to—flow properties, shear-stress, boundary-site transitions, roughness of material of a medical product can cause the generating of misfoldings in proteins/peptides (see "biopharmaceuticals") it is necessary to assess the impact of such qualities on the generating of misfolded proteins/peptides.

The Invention Presented Here Describes Binder Substances for Misfolded Proteins/Peptides to be Used in Methods to Analyze the Influence of Medical Products on Proteins/Peptides and Methods to Analyse the Impact of Medical Products on Proteins/Peptides and Methods of Optimizing Such Medical Products According to invention a substance for analysing the impact of a medical product on the generating of misfoldings in proteins/peptides is defined as a binder substance for misfolded proteins/peptides, preferably a binder substance like ADAM15 (Metargidin), the metalloprotease domain of ADAM15 and in particular peptides which hold the sequence of His, Trp, Arg, Arg, Ala, His, Leu, Leu, Pro, Arg, Leu, Pro (HWRRAHLLPRLP) corresponding to ADAM15 sequences 286-297, the sequence Glu, Asn, Phe, Leu, His, Trp, Arg, Arg, Ala, His, Leu, Leu (ENFLHWRRAHLL) ADAM 15 sequence 282-293 or the sequence Ala, Val, Thr, Leu, Glu, Asn, Phe, Leu, His, Trp, Arg, Arg ADAM15 sequences 278-289, His, Trp, Arg, Arg, Pro or His, Trp, Arg, Arg (HWRR) as well as the Kringel 5 domain of plasminogen and in particular the amino acid sequence PRKLYDY or amino acid sequences holding the sequence PRKLYDY.

According to invention fluids which contain proteins/peptides, favorably body fluids containing protein, of humans or animals, especially favored blood or plasma which will flow or be pumped through a medical product. Specifically preferred are therewith purely rheological conditions and velocities of flow as they occur when blood flows through a human or animal body. Before allowing the protein-/peptide-holding fluid in as well as after circulation through the medical product fluid-samples are taken. In analogy to the above-mentioned detection of misfolded proteins in body fluids to be used for diagnostic purposes the samples are analysed before and after the flow of fluid through the medical product and the contents of misfolded proteins/peptides is to be detected and quantified.

To optimise such a medical product models of the latter are described in respect to the effect of misfolded proteins/peptides and are then compared to one another so that in the end that model or that procedure will undergo further development which has generated a product with lower rates of concentration in misfolded proteins/peptides from the same-self protein-solution—preferably blood or plasma.

A very favourable performance of the presented invention lies in the above-mentioned survey by means of using animal or human blood in combination with one or several analyses of the effect of a medical product as to the status of activating thrombocytes as well as the full impact of thrombocytes, the activating of coagulation, fibrinolysis, kallikrein-system, complement system from the same test samples or others generated in a parallel-designed procedure. Here the favourable feature are the quantifications of chaperones, preferably GRP78/BIP on the surface of the thrombocytes; also the presentation of CD62 and/or CD63 on the surface of thrombocytes; also the adsorption and storing of mepacrine in thrombocytes, also the binding of a reagent for identification of activated GPIIbIIIa with thrombocytes; also the assessment and/or quantification of microparticles from thrombocytes, leucocytes and lymphocytes; also the analysis and/or quantification of associates from thrombocytes with neutrophil granulocytes or with monocytes; also quantification of soluble cleavage products of thrombocytes like P-selectin, GPIb-fragment, GPV-fragment, PAR-1 cleavage, PAR-4 cleavage, the quantification of surface proteins on thrombocytes; also measuring of activating marker for thrombocytes after targeted activating with agonists; also measuring of change in shape of thrombocytes, also measuring of the adhesion capacities, the analysis of capacity of thrombocytes without and after targeted activation to bind fibrinogen, also decrease of the amount of thrombocytes, leucocytes, erythrocytes after their passing passage through the medical product; also measuring and hemolysis, also measuring of the capacity of thrombocytes without/or after targeted activation of von Willebrand factor for binding; also the concentration and the multimer-pattern of vWF; also activating marker for leucocytes; also assessment of capacity of leucocytes to transmigrate through a cellular layer; also measuring of substances like—but non restricted to—cytokine, growth factors, proteins, ATP, on blood cells; also measuring of activity markers of coagulation like—but not restricted to—thrombin-antithrombin-complex, fibrin-monomeres F1+2; also analysis of markers of activated fibrinolysis like—but not restricted to—DDimer, plasmin-antiplasmin-complex; also measuring of activation of FXII-kallekrein-pathways; also assessment of activity markers of the complement system like—but not restricted to—C3a, C5a, Bb, iC3b, C4b, SC5b-9, CH50, C3-convertasis, C5-convertasis.

6. Identification Reagent and Method of Detection of Misfolded Proteins/Peptides for Using these Substances Amyloids are an attractive kind of building material for many technical devices as they belong to the most important self-organizing nano-materials. They have a simple repetitively ordered structure, a robust design and they are a highly durable and inexpensive material. Amyloids are favorable candidates for the production of molecular nano-biomaterials such as wire, coatings, gellies, scaffolds, matrices and fluid crystals[147,148]. Feasible examples of nano-material from misfolded proteins/peptides are e.g. nano pipe conductors[149,150]. Such conductors can e.g. be processed from misfolded n-terminal and central-sections of the protein SU36p of ale yeast *saccharomyces cerevisiae*. Misfolded monomer or oligomere proteins/peptides are the preliminary stage of amyloids. A further performance of the invention presented here is the making use of one of the binder substances—according to invention—in order to search efficiently for misfolded proteins/peptides and thus for possible future building material for amyloid fibres in bio-materials.

Besides their technical appliances misfolded proteins/peptides can also be useful elsewhere like—but not restricted to—as an adjuvant in the generation of antibodies and vaccine (patent: amyloid proteins as vaccine scaffolds. Inventors: Amy Rosenberg (FDA), James E. Keller (FDA), Robert Tycko (NIDDK)).

The binder substances—according to invention—can therefore also be used to search for and find misfolded proteins in biomaterials for useful devices.

7. Enriching Microorganisms which Hold Misfolded Proteins on their Surface to Facilitate Diagnostic Procedures Many microorganisms, possibly even all of them that can tag to a host provide misfolded proteins/peptides on their surface[151]. If microorganisms are single items in the blood bags, preparations for parenteral use or in body fluids such as blood, liquor, synovial fluid and others from humans and animals diagnostics would become a very difficult matter.

The invention presented here allows for concentrating microorganisms from larger samples of material and thus supporting the process and result of diagnosing. To initiate this procedure one of the binder substrates—according to invention—as to misfolded proteins/peptides will be immobilised to a solid surface such as beads, basic materials like filters, membrane, and the body fluid will be put into contact. The microorganisms bind to the solid phase. After separating body fluid and solid phase the microorganisms on the solid phase have become enriched and can more easily be identified.

FIGURES

FIG. 1 shows the result of the measurement of the optical density at 492 nm for the binding of HOCl-modified albumin and of HOCl-modified ATIII to the peptide PRKLYDY from example 3a.

FIG. 6 shows the result of the measurement of the optical density at 492 nm for the binding of GPV-fragment respectively GPIb from platelet activation supernatant to the peptide PRKLYDY from example 3m.

FIG. 8 shows the result of the measurement of the optical density at 492 nm for the binding of HOCl-modified albumin and of HOCl-modified ATIII to the peptide HWRRAHLLPRLP from example 4a.

FIG. 12 shows the result of the measurement of the optical density at 492 nm for the binding of GPV-fragment respectively GPIb from platelet activation supernatant to the peptide HWRRAHLLPRLP from example 4m.

FIG. 13 shows the result of the measurement of the optical density at 492 nm for the binding of HOCl-modified ATIII to the peptide HWRRAHLLPRLP from example 4o.

EXAMPLES FOR THE INVENTION

1. Synthesis of the Peptides According to the Invention

The peptides PRKLYDY and HWRRAHLLPRLP were synthesized after the standard solid phase synthesis in an automatic peptide synthesizer. Hereby the strategy of the N-terminal Fmoc-protective group was used (cleavage of the protective group with piperidin after each coupling step). The solvent was dimethylformamide. The coupling was carried out with the use of TBTU (activator of carboxyl groups) and 4-methyl morpholine (deprotonation of amino groups).

After the final cleavage of the Fmoc protective groups the peptides were removed from the resin by trifluor acetic acid and thereafter purified by HPLC. The quality was controlled by MS.

2. Synthesis of Biotin Coupled Peptides According to the Invention a) biotinylated PRKLYDY: The peptide PRKLYDY was manufactured as mentioned in example 1. After the final cleavage of the Fmoc protective group it was conversed with Fmoc-amino hexane acid (as spacer). After a further Fmoc-cleavage it was incubated with biotin, afterwards again cleaved with trifluor acetic acid from the resin and subsequently purified by HPLC. Finally the quality was controlled by MS.

b) Biotinylated HWRRAHLLPRLP: the peptide HWRRAHLLPRLP was manufactured as mentioned in example 1. The N-terminal Fmoc-protective group was cleaved and the N-terminus was protected with a Boc-protectiv group. Then the DDE-protective groups on the C-terminal lysine were cleaved with hydrazine hydrate. Afterwards the epsilon-amino group of the lysine was incubated with biotin. The peptide was cleaved with trifluor acetic acid from the resin and subsequently purified by HPLC. Finally the quality was controlled by MS.

3. Detection and Measurement of Different Misfolded Proteins with Biotin-PRKLYDY in Plate Binding Assays a) Detection and Measurement of Misfolded HOCl-Modified Proteins Here as Examples Albumin, Fibrinogen, Antithrombin, LDL)

Biotinylated PRKLYDY was coated on a preblocked streptavidin plate for 1 hour at room temperature. After a washing step different concentrations of HOCl-modified albumin, or HOCl-modified fibrinogen, or HOCl-modified antithrombin, or HOCl-modified LDL (including negative control) were added for 1 hour at room temperature. After another washing step mouse anti HSA antibody was added to HOCl-modified albumin, rabbit anti fibrinogen antibody to HOCl-modified fibrinogen, rabbit anti antithrombin antibody to HOCl-modified antithrombin and mouse anti Apo B antibody to HOCl-modified LDL for 1 hour at room temperature. After another washing step the corresponding peroxidase coupled secondary antibody was added for 1 hour at room temperature. After a final washing step it was stained with o-phenylenediamine-substrate and the reaction was stopped after 30 min with 4 N sulphuric acid. The optical density was measured at 492 nm.

b) Detection and Measurement of Human Alpha Defensine (HNP1-4)

Figure 1:
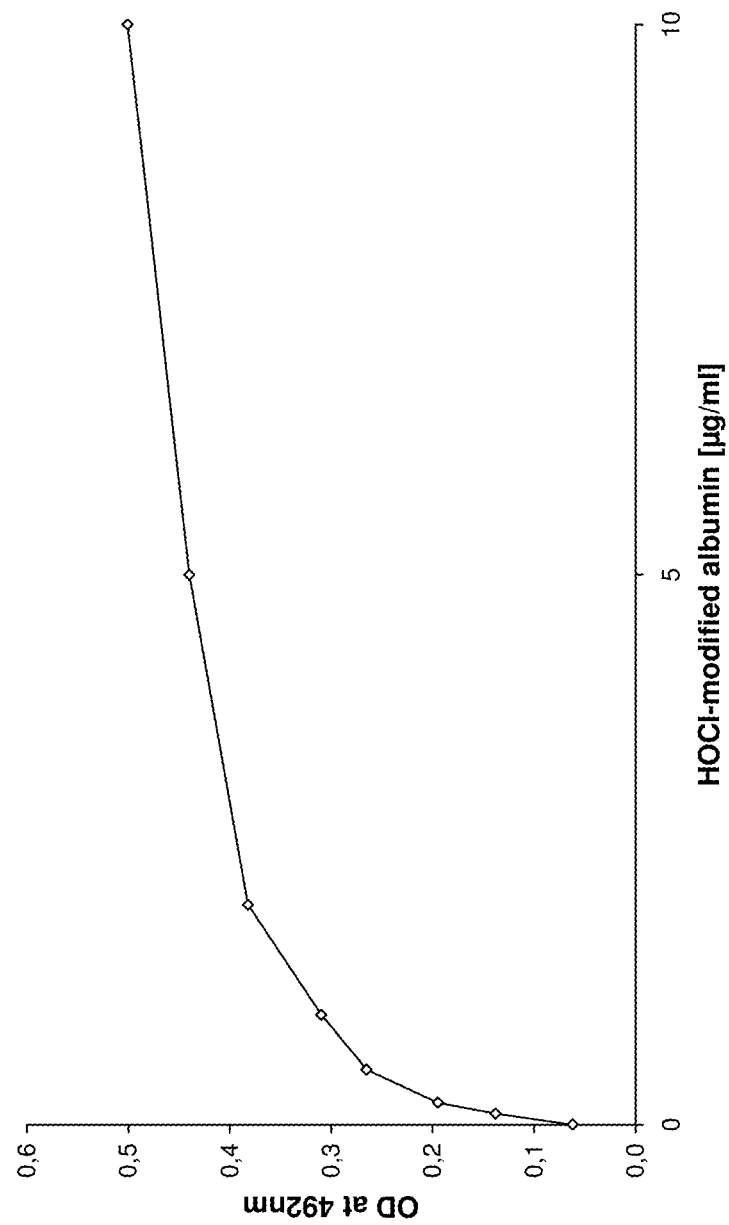

Biotinylated PRKLYDY was coated on a preblocked streptavidin plate for 1 hour at room temperature. After a washing step different concentrations of defensine (including negative control) were added for 1 hour at room temperature. After another washing step mouse anti defensine antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm. The result is illustrated in FIG. 1.

c) Detection and Measurement of AGE-Proteins (as Example AGE-BSA, AGE-HB, AGE-HSA)

Biotinylated PRKLYDY was coated on a preblocked streptavidin plate for 1 hour at room temperature. After a washing step different concentrations of AGE-BSA, or AGE-HSA, or AGE-HB (including negative control) were added for 1 hour at room temperature. After another washing step for AGE-BSA mouse anti BSA, for AGE-HSA mouse anti HSA and for AGE-HB chicken anti HB were added for 1 hour at room temperature. After another washing step the corresponding secondary antibody, coupled with peroxidase, was added for 1 hour at room temperature. After a final washing step it was stained with o-phenylenediamine-substrate and the reaction was stopped after 30 min with 4 N sulphuric acid. The optical density was measured at 492 nm.

d) Detection and Measurement of Misfolded Proteins of Microorganisms (Here as Example EAP from *S. Aureus*)

Figure 2:
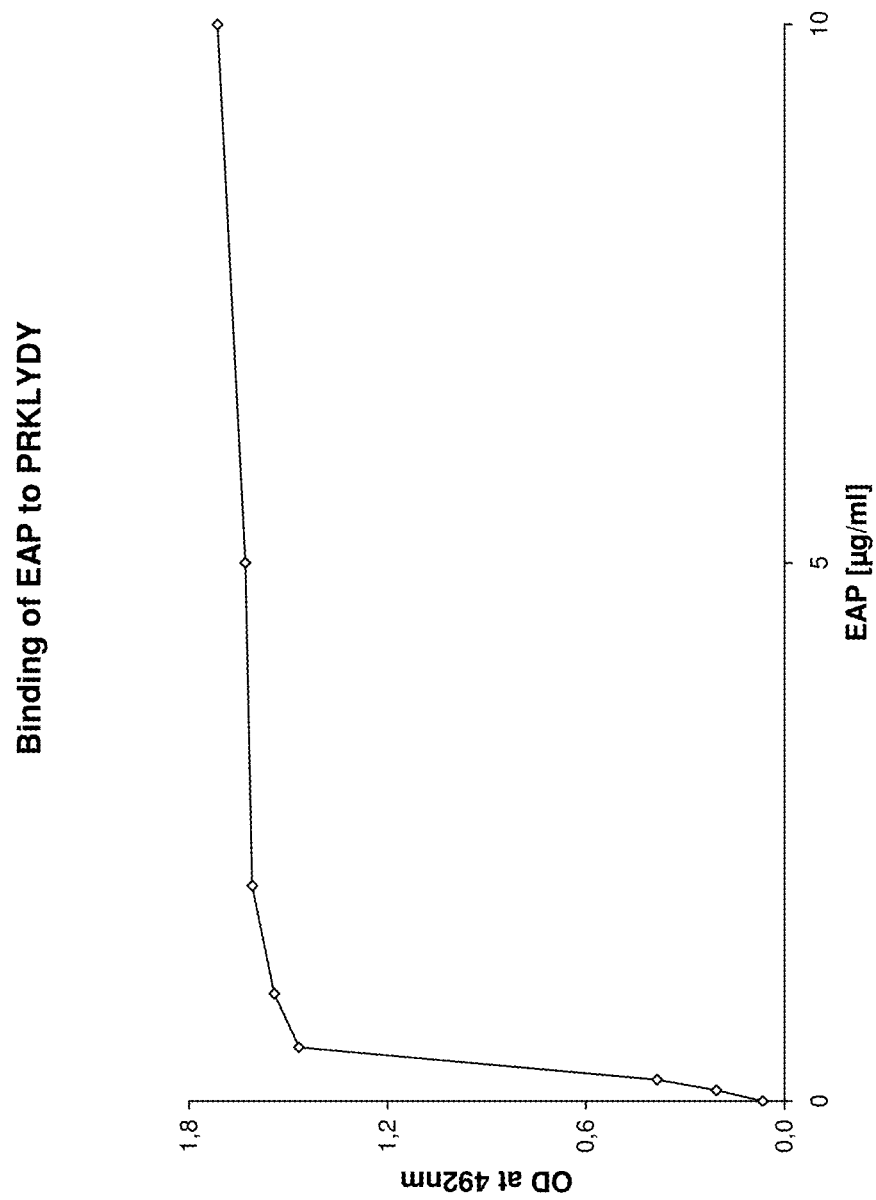
FIG. 2 shows the result of the measurement of the optical density at 492 nm for the binding of EAP to the peptide PRKLYDY from example 3d.

Biotinylated PRKLYDY was coated on a preblocked streptavidin plate for 1 hour at room temperature. After a washing step different concentrations of EAP (including negative control) were added for 1 hour at room temperature. After another washing step rabbit anti EAP antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 2).

e) Detection and Measurement of Misfolded Immunoglobulins (Here as Example KSCN Treated IgG, Urea-Treated IgG, Heat-Treated IgG, by Multiple Freezing and Thawing Treated IgG, HOCl Treated IgG)

Figure 3:
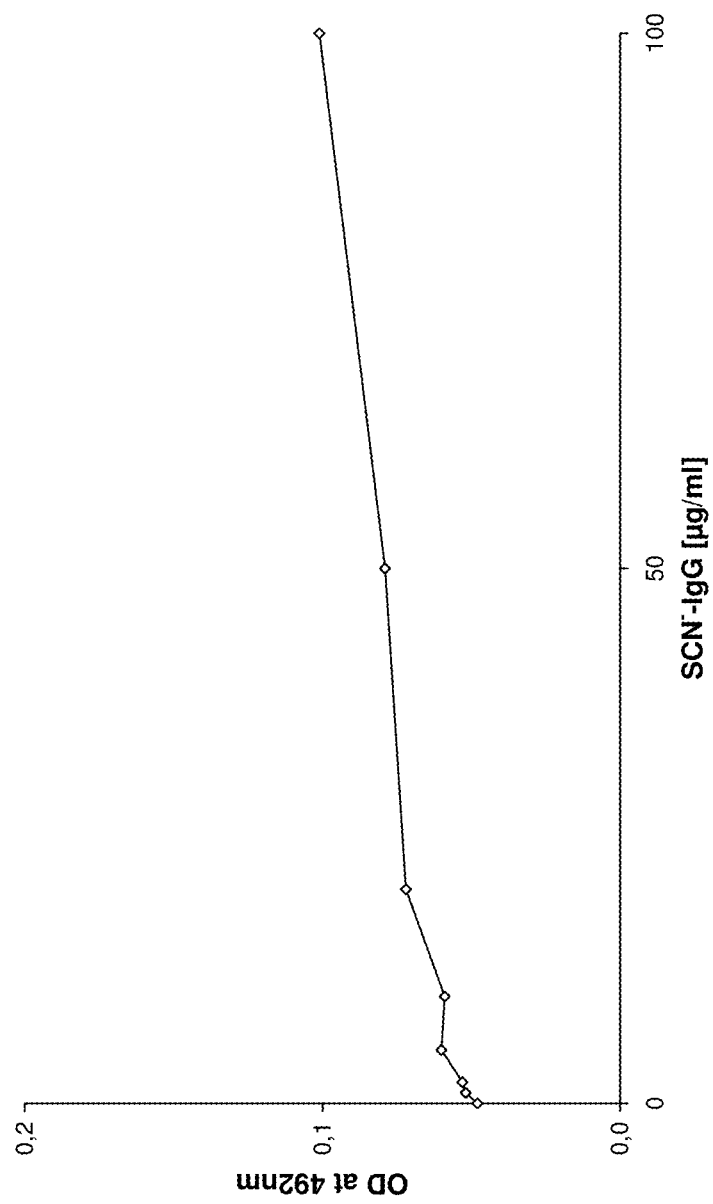
FIG. 3 shows the result of the measurement of the optical density at 492 nm for the binding of SCN⁻-IgG respectively of Urea-IgG to the peptide PRKLYDY from example 3e.

Biotinylated PRKLYDY was coated on a preblocked streptavidin plate for 1 hour at room temperature. After a washing step different concentrations of SCN⁻-treated IgG, or Urea-treated IgG, or heat-treated IgG, or by multiple freezing and thawing treated IgG, or HOCl-treated IgG (including negative control), were added for 1 hour at room temperature. After another washing step anti human IgG-POD antibody was added for 1 hour at room temperature. After a final washing step it was stained with o-phenylenediamine-substrate and the reaction was stopped after 30 min with 4 N sulphuric acid. The optical density was measured at 492 nm (FIG. 3).

f) Detection and Measurement of Amyloid Beta Peptide (1-42)

Biotinylated PRKLYDY was coated on a preblocked streptavidin plate for 1 hour at room temperature. After a washing step different concentrations of beta amyloid peptide (1-42) (including negative control) were added for 1 hour at room temperature. After another washing step mouse anti beta amyloid peptide antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

g) Detection and Measurement of Misfolded Peptide from Thrombospondin-1

Figure 4:
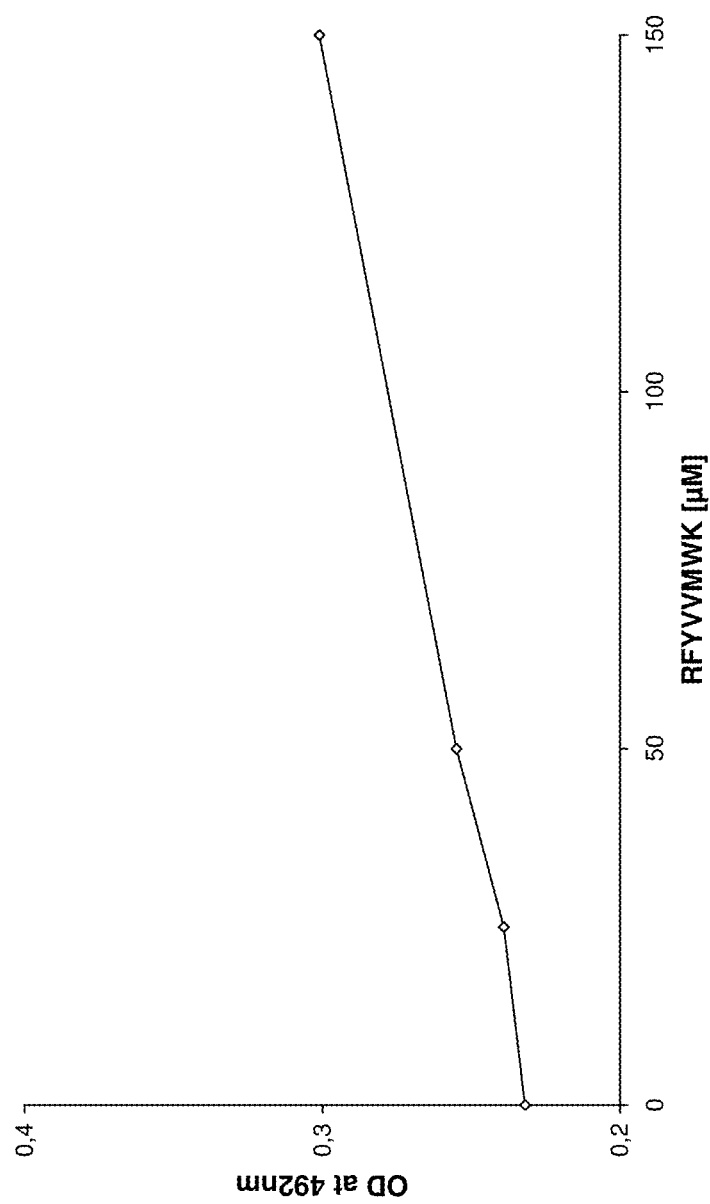
FIG. 4 shows the result of the measurement of the optical density at 492 nm for the binding of RFYVVMWK to the peptide PRKLYDY from example 3g.

Biotinylated PRKLYDY was coated on a preblocked streptavidin plate for 1 hour at room temperature. After a washing step different concentrations of TSP-1-peptide RFYVVMWK (including negative control) were added for 1 hour at room temperature. After another washing step rabbit anti TSP-1 antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 4).

h) Detection and Measurement of Amylin

Biotinylated PRKLYDY was coated on a preblocked streptavidin plate for 1 hour at room temperature. After a washing step different concentrations of amylin (including negative control) were added for 1 hour at room temperature. After another washing step human anti amylin antibody was added for 1 hour at room temperature. After another washing step the corresponding secondary antibody, anti human IgG POD, was added for 1 hour at room temperature. After a final washing step it was stained with o-phenylenediamine-substrate and the reaction was stopped after 30 min with 4 N sulphuric acid. The optical density was measured at 492 nm.

i) Detection and Measurement of Scrambled RNase

Biotinylated PRKLYDY was coated on a preblocked streptavidin plate for 1 hour at room temperature. After a washing step different concentrations of scrambled RNase (including negative control) were added for 1 hour at room temperature. After another washing step rabbit anti RNase antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm.

j) Detection and Measurement of "Activated" Alpha2 Macroglobulin

Alpha 2 macroglobulin was activated in two different ways.
A) Human alpha 2 macroglobulin was incubated for 2 h at 37° C. with 2 µM trypsin and the reaction was stopped by adding 100 µM (end concentration) p-nitrophenyl-p'-guanidinobenzoat-HCl.
B) Human alpha 2 macroglobulin was incubated over night at 37° C. with 200 mM ammonium carbonate and afterwards dialysed against PBS-buffer.

The in this way "activated" alpha 2 macroglobulins were added in different concentrations (including negative control) to a PRKLYDY coated, preblocked streptavidin plate and incubated for 1 hour at room temperature. After a washing step rabbit anti alpha 2 macroglobulin antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm.

k) Detection and Measurement of sPla2 Modified LDL

LDL isolated from human plasma was incubated for 24 hours at 37° C. with sPLA2 and the reaction was stopped by adding 10 mM EDTA. The in this way modified LDL was added in different concentrations (including negative control) to a with PRKLYDY coated, preblocked streptavidin plate and incubated for 1 hour at room temperature. After a washing step mouse anti Apo B antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulfuric acid. The optical density was measured at 492 nm.

l) Detection and Measurement of Misfolded Apo B100 Lipoprotein

Misfolded Apo B100 lipoprotein was added in different concentrations (including negative control) to a PRKLYDY coated, preblocked streptavidin plate and incubated for 1 hour at room temperature. After a washing step mouse anti Apo B antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

m) Detection and Measurement of Shedded Soluble Membrane Proteins (Here as Example sP-Selektin, sCD36, GPV-Fragment, GPVI-Fragment, GPIb-Fragment)

Figure 5:
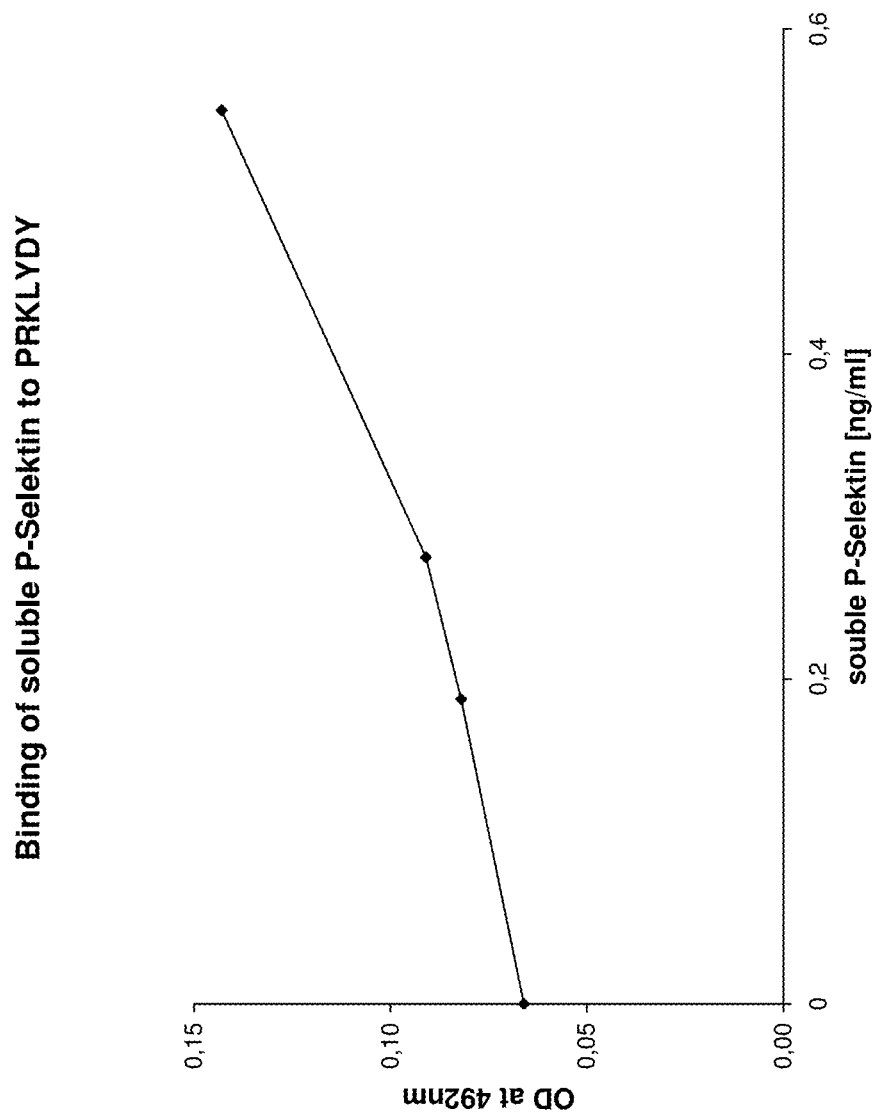
FIG. 5 shows the result of the measurement of the optical density at 492 nm for the binding of soluble P-Selektin to the peptide PRKLYDY from example 3m.
Figure 6:
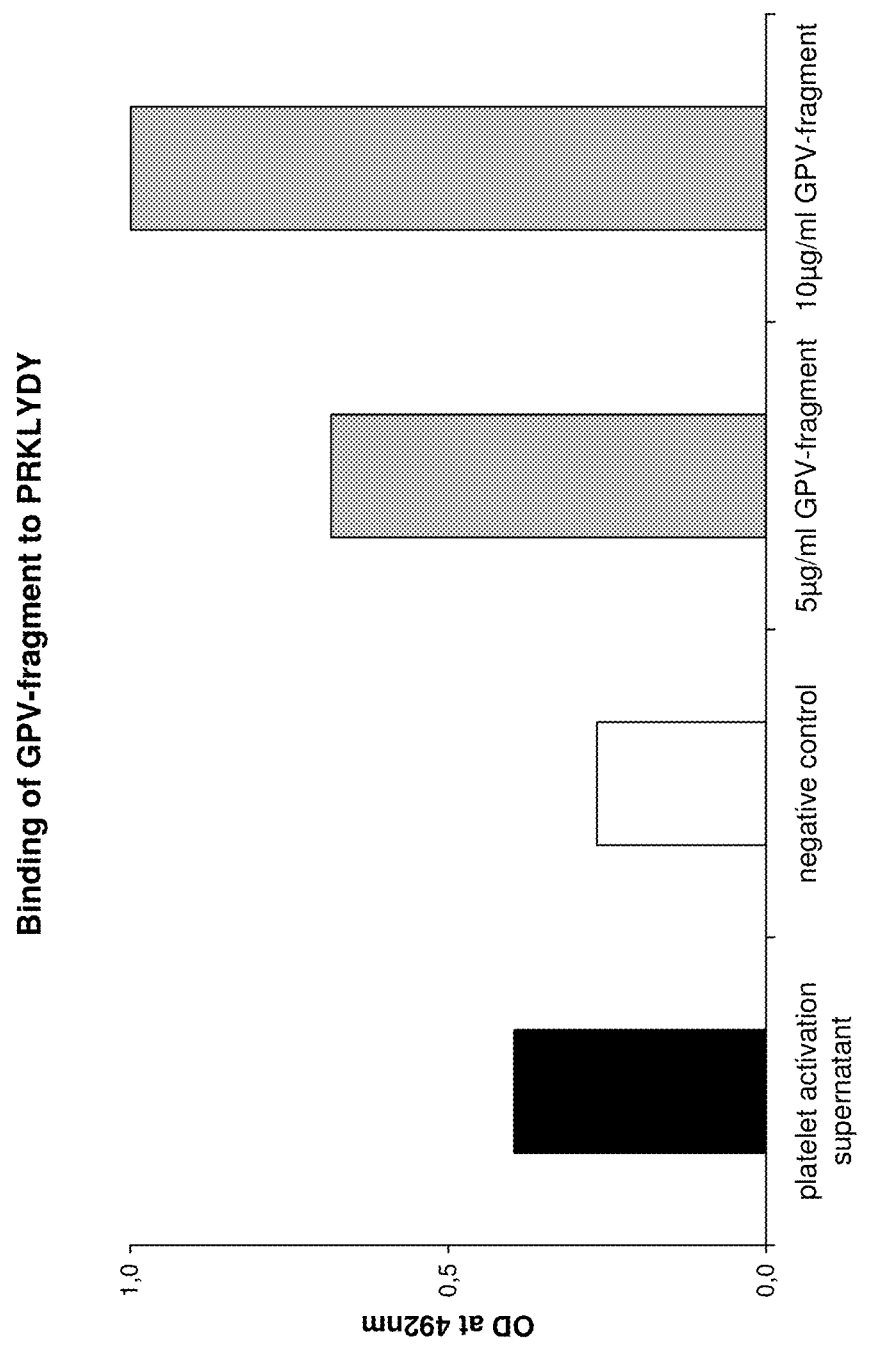

Soluble P-Selektin, soluble CD36, GPV-fragment or GPIb of with collagen and thrombin activated platelets (activation supernatant) were added in different concentrations (including negative control) to a PRKLYDY coated, preblocked streptavidin plate and incubated for 1 hour at room temperature. After a washing step P-Selektin was incubated with mouse anti CD62P, CD36 with mouse anti CD36, GPV with rabbit anti GPV, or GPIb with rabbit anti GPIb antibody for 1 hour at room temperature. After another washing step the corresponding secondary antibody, coupled with peroxidase, was added for 1 hour at room temperature. After a final washing step it was stained with o-phenylenediamine-substrate and the reaction was stopped after 30 min with 4 N sulphuric acid. The optical density was measured at 492 nm (FIGS. 5, 6).

n) Detection and Measurement of Misfolded Beta2-Microglobulin

Biotinylated PRKLYDY was coated on a preblocked streptavidin plate for 1 hour at room temperature. After a washing step different concentrations of misfolded beta 2 microglobulin (including negative control) were added for 1 hour at room temperature. After another washing step mouse anti beta 2 microglobulin antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

o) Detection and Measurement of Misfolded Serpines (Here as Example Antithrombin III, Alpha1 Antitrypsin)

Figure 7:
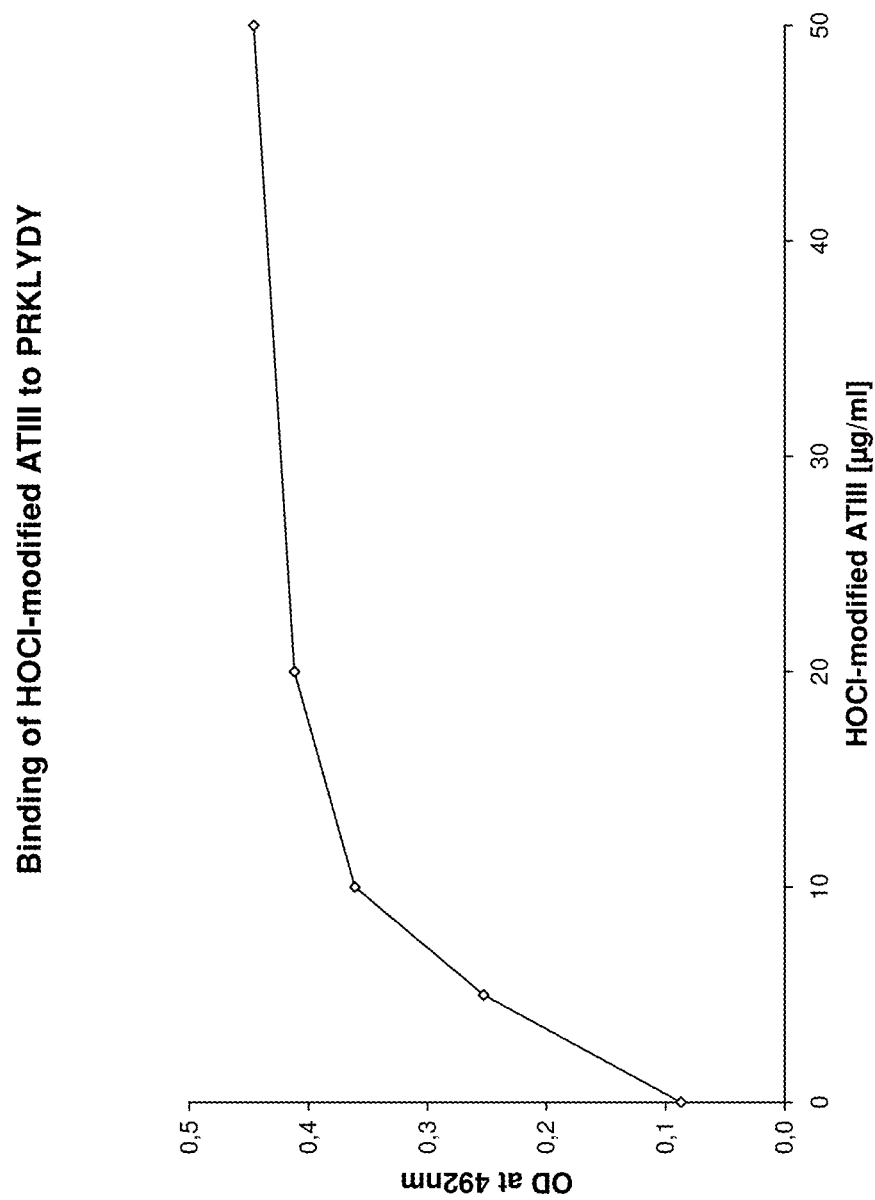
FIG. 7 shows the result of the measurement of the optical density at 492 nm for the binding of HOCl-modified ATIII to the peptide PRKLYDY from example 3o.

Biotinylated PRKLYDY was coated on a preblocked streptavidin plate for 1 hour at room temperature. After a washing step different concentrations of HOCl-modified ATIII, or HOCl-modified alpha 1 antitrypsin (including negative control) were added for 1 hour at room temperature. After another washing step rabbit anti ATIII was added to misfolded antithrombin and rabbit anti alpha 1 antitrypsin antibody was added to misfolded alpha 1 antitrypsin for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulfuric acid. The optical density was measured at 492 nm (FIG. 7).

4. Detection and Measurement of Different Misfolded Proteins with Biotin-HWRRAHLLPRLP in Plate Binding Assays a) Detection and Measurement of Misfolded HOCl-Modified Proteins (Here as Examples Albumin, Fibrinogen, Antithrombin, LDL)

Figure 8:
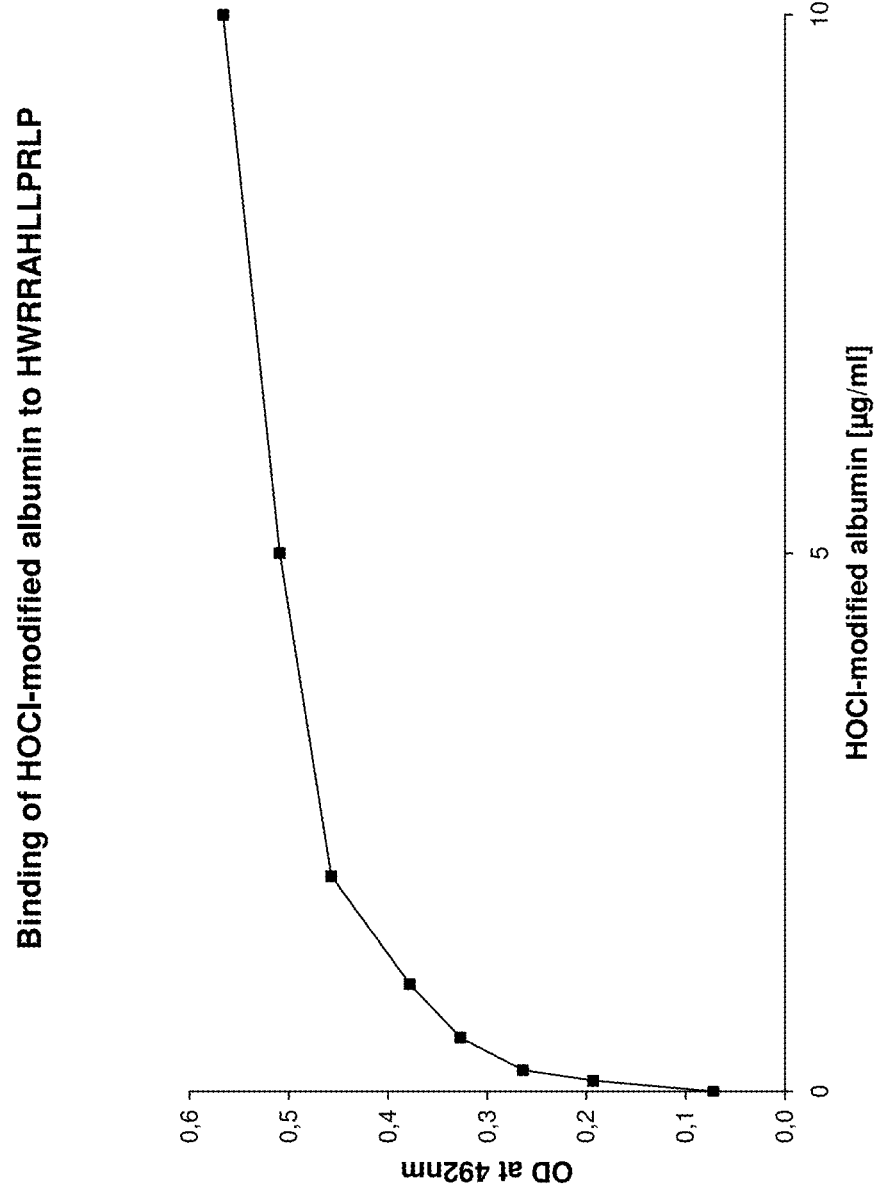

Biotinylated HWRRAHLLPRLP was coated on a preblocked streptavidin plate for 1 hour at room temperature. After a washing step different concentrations of HOCl-modified albumin, or HOCl-modified fibrinogen, or HOCl-modified antithrombin, or HOCl-modified LDL (including negative control) were added for 1 hour at room temperature. After another washing step mouse anti HSA antibody was added to HOCl-modified albumin, rabbit anti fibrinogen antibody to HOCl-modified fibrinogen, rabbit anti antithrombin antibody to HOCl-modified antithrombin and mouse anti Apo B antibody to HOCl-modified LDL for 1 hour at room temperature. After another washing step the corresponding peroxidase coupled secondary antibody was added for 1 hour at room temperature. After a final washing step it was stained with o-phenylenediamine-substrate and the reaction was stopped after 30 min with 4 N sulphuric acid. The optical density was measured at 492 nm (FIG. 8).

b) Detection and Measurement of Human Alpha Defensine (HNP1-4)

Biotinylated HWRRAHLLPRLP was coated on a preblocked streptavidin plate for 1 hour at room temperature. After a washing step different concentrations of defensine (including negative control) were added for 1 hour at room temperature. After another washing step mouse anti defensine antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

c) Detection and Measurement of AGE-Proteins (as Example AGE-BSA, AGE-HB, AGE-HSA)

Biotinylated HWRRAHLLPRLP was coated on a preblocked streptavidin plate for 1 hour at room temperature. After a washing step different concentrations of AGE-BSA, or AGE-HSA, or AGE-HB (including negative control) were added for 1 hour at room temperature. After another washing step for AGE-BSA mouse anti BSA, for AGE-HSA mouse anti HSA and for AGE-HB chicken anti HB were added for 1 hour at room temperature. After another washing step the corresponding secondary antibody, coupled with peroxidase, was added for 1 hour at room temperature. After a final washing step it was stained with o-phenylenediamine-substrate and the reaction was stopped after 30 min with 4 N sulphuric acid. The optical density was measured at 492 nm.

d) Detection and Measurement of Misfolded Proteins of Microorganisms (Here as Example EAP from *S. Aureus*)

Figure 9:
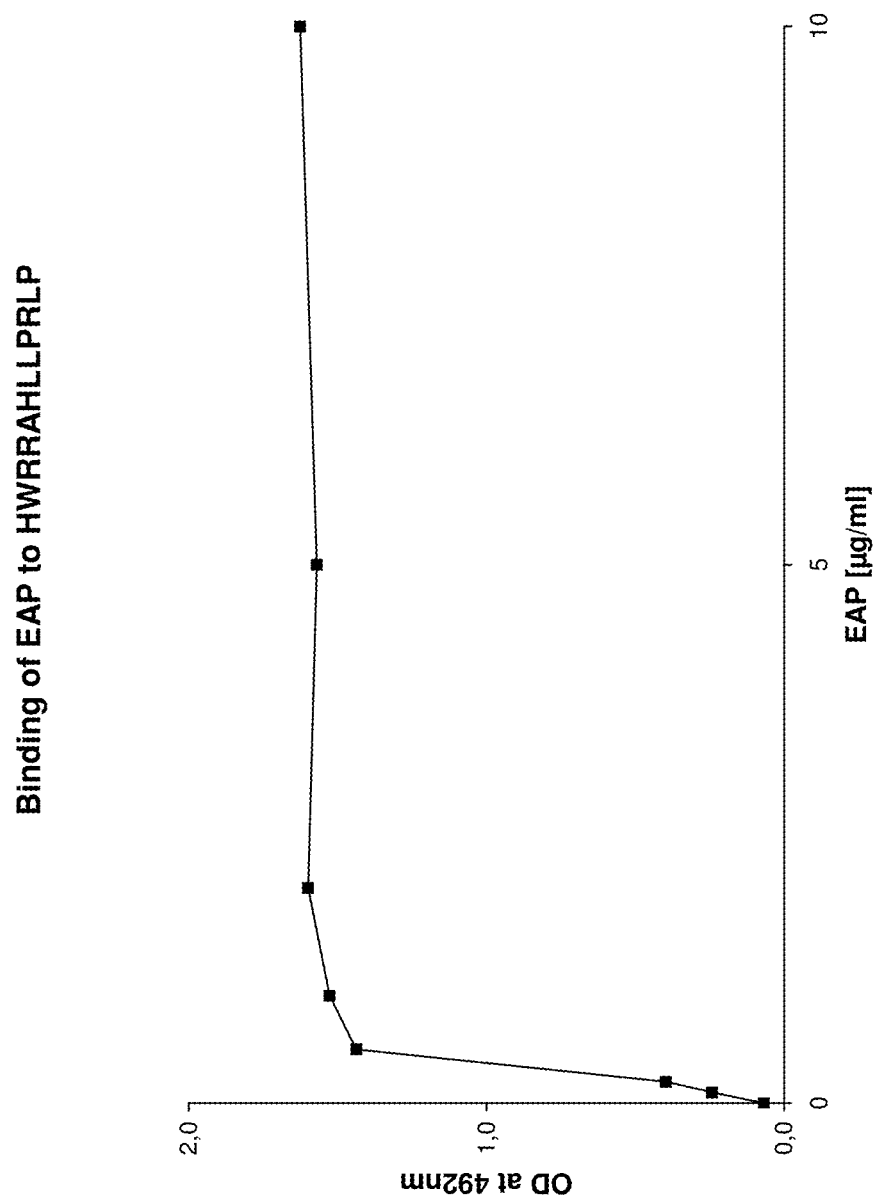
FIG. 9 shows the result of the measurement of the optical density at 492 nm for the binding of EAP to the peptide HWRRAHLLPRLP from example 4d.

Biotinylated HWRRAHLLPRLP was coated on a preblocked streptavidin plate for 1 hour at room temperature. After a washing step different concentrations of EAP (including negative control) were added for 1 hour at room temperature. After another washing step rabbit anti EAP antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 9).

e) Detection and Measurement of Misfolded Immunoglobulins (Here as Example KSCN Treated IgG, Urea-Treated IgG, Heat-Treated IgG, by Multiple Freezing and Thawing Treated IgG, HOCl Treated IgG)

Figure 10:
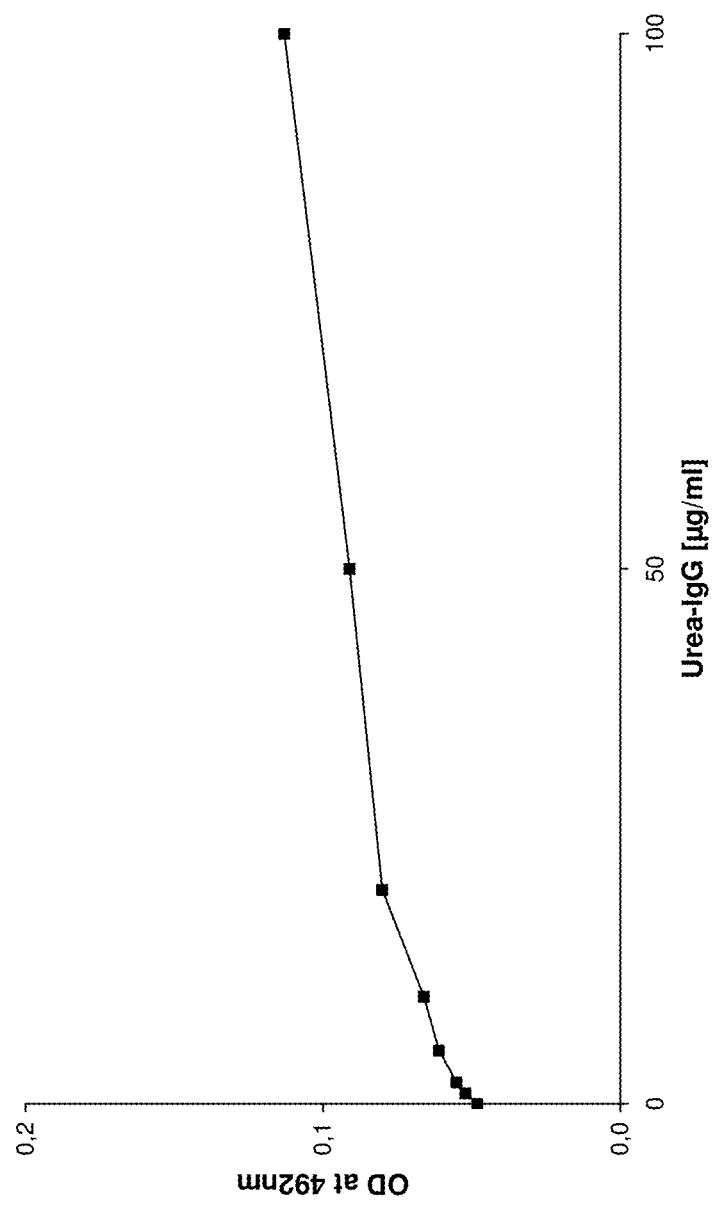
FIG. 10 shows the result of the measurement of the optical density at 492 nm for the binding of SCN⁻-IgG respectively of Urea-IgG to the peptide HWRRAHLLPRLP from example 4e.

Biotinylated HWRRAHLLPRLP was coated on a preblocked streptavidin plate for 1 hour at room temperature. After a washing step different concentrations of SCN⁻-treated IgG, or Urea-treated IgG, or heat-treated IgG, or by multiple freezing and thawing treated IgG, or HOCl-treated IgG (including negative control), were added for 1 hour at room temperature. After another washing step anti human IgG-POD antibody was added for 1 hour at room temperature. After a final washing step it was stained with o-phenylenediamine-substrate and the reaction was stopped after 30 min with 4 N sulphuric acid. The optical density was measured at 492 nm (FIG. 10).

f) Detection and Measurement of Amyloid Beta Peptide (1-42)

Biotinylated HWRRAHLLPRLP was coated on a preblocked streptavidin plate for 1 hour at room temperature. After a washing step different concentrations of beta amyloid peptide (1-42) (including negative control) were added for 1 hour at room temperature. After another washing step mouse anti beta amyloid peptide antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

g) Detection and Measurement of Misfolded Peptide from Thrombospondin-1

Figure 11:
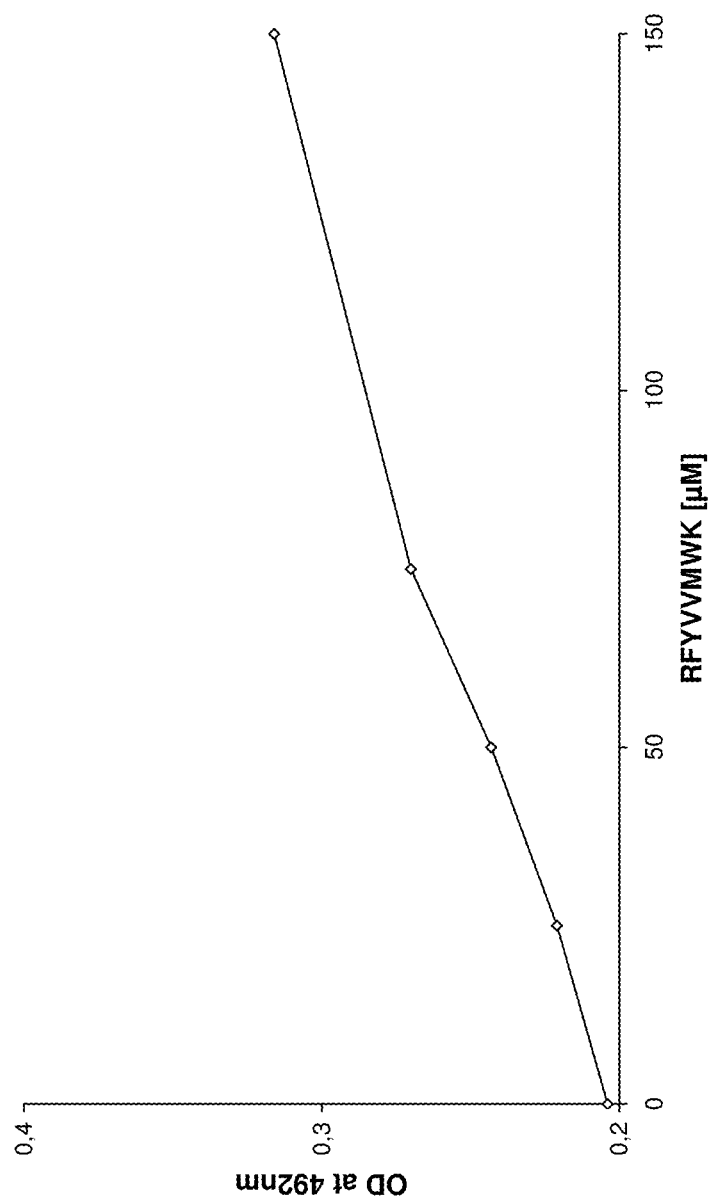
FIG. 11 shows the result of the measurement of the optical density at 492 nm for the binding of RFYVVMWK to the peptide HWRRAHLLPRLP from example 4g.

Biotinylated HWRRAHLLPRLP was coated on a preblocked streptavidin plate for 1 hour at room temperature. After a washing step different concentrations of TSP-1-peptide RFYVVMWK (including negative control) were added for 1 hour at room temperature. After another washing step rabbit anti TSP-1 antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 11).

h) Detection and Measurement of Amylin

Biotinylated HWRRAHLLPRLP was coated on a preblocked streptavidin plate for 1 hour at room temperature. After a washing step different concentrations of amylin (including negative control) were added for 1 hour at room temperature. After another washing step human anti amylin antibody was added for 1 hour at room temperature. After another washing step the corresponding secondary antibody, anti human IgG POD, was added for 1 hour at room temperature. After a final washing step it was stained with o-phenylenediamine-substrate and the reaction was stopped after 30 min with 4 N sulfuric acid. The optical density was measured at 492 nm.

i) Detection and Measurement of Scrambled RNase

Biotinylated HWRRAHLLPRLP was coated on a preblocked streptavidin plate for 1 hour at room temperature. After a washing step different concentrations of scrambled RNase (including negative control) were added for 1 hour at room temperature. After another washing step rabbit anti RNase antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm.

j) Detection and Measurement of "Activated" Alpha2 Macroglobulin

Alpha 2 macroglobulin was activated in two different ways.

A) Human alpha 2 macroglobulin was incubated for 2 h at 37° C. with 2 µM trypsin and the reaction was stopped by adding 100 µM (end concentration) p-nitrophenyl-p'-guanidinobenzoat-HCl.

B) Human alpha 2 macroglobulin was incubated over night at 37° C. with 200 mM ammonium carbonate and afterwards dialysed against PBS-buffer.

The in this way "activated" alpha 2 macroglobulins were added in different concentrations (including negative control) to a HWRRAHLLPRLP coated, preblocked streptavidin plate and incubated for 1 hour at room temperature. After a washing step rabbit anti alpha 2 macroglobulin antibody was added for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm.

k) Detection and Measurement of sPla2 Modified LDL

LDL isolated from human plasma was incubated for 24 hours at 37° C. with sPLA2 and the reaction was stopped by adding 10 mM EDTA. The in this way modified LDL was added in different concentrations (including negative control) to a with HWRRAHLLPRLP coated, preblocked streptavidin plate and incubated for 1 hour at room temperature. After a washing step mouse anti Apo B antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm l) Detection and Measurement of Misfolded Apo B100 Lipoprotein Misfolded Apo B100 lipoprotein was added in different concentrations (including negative control) to a HWRRAHLLPRLP coated, preblocked streptavidin plate and incubated for 1 hour at room temperature. After a washing step mouse anti Apo B antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

m) Detection and Measurement of Shedded Soluble Membrane Proteins (Here as Example sP-Selektin, sCD36, GPV-Fragment, GPVI-Fragment, GPIb-fragment)

Soluble P-Selektin, soluble CD36, GPV-fragment or GPIb of with collagen and thrombin activated platelets (activation supernatant) were added in different concentrations (including negative control) to a HWRRAHLLPRLP coated, preblocked streptavidin plate and incubated for 1 hour at room temperature. After a washing step P-Selektin was incubated with mouse anti CD62P, CD36 with mouse anti CD36, GPV with rabbit anti GPV, or GPIb with rabbit anti GPIb antibody for 1 hour at room temperature. After another washing step the corresponding secondary antibody, coupled with peroxidase, was added for 1 hour at room temperature. After a final washing step it was stained with o-phenylenediamine-substrate and the reaction was stopped after 30 min with 4 N sulphuric acid. The optical density was measured at 492 nm (FIG. 12).

n) Detection and Measurement of Misfolded Beta2-Microglobulin

Biotinylated HWRRAHLLPRLP was coated on a preblocked streptavidin plate for 1 hour at room temperature. After a washing step different concentrations of misfolded beta 2 microglobulin (including negative control) were added for 1 hour at room temperature. After another washing step mouse anti beta 2 microglobulin antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm.

o) Detection and Measurement of Misfolded Serpines (Here as Example Antithrombin III, Alpha1 Antitrypsin)

Figure 13:
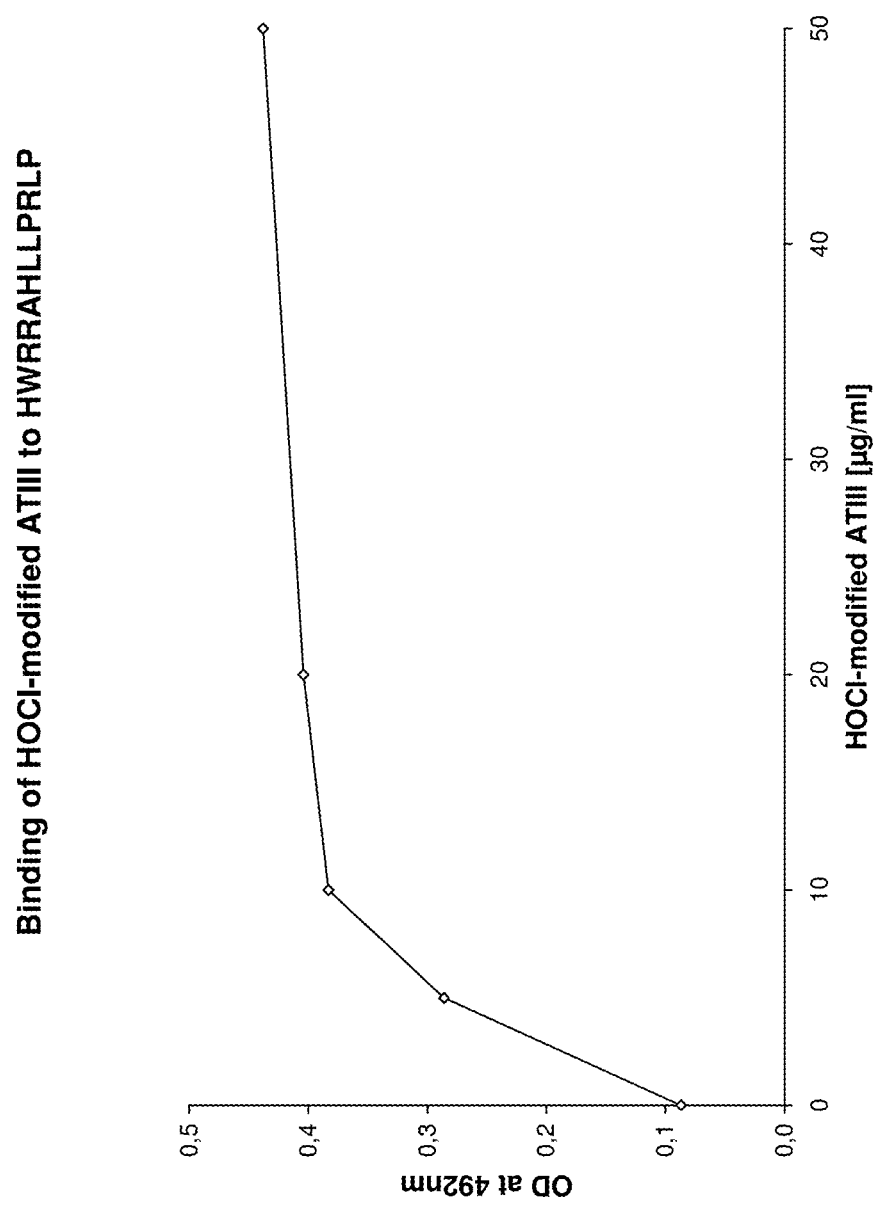

Biotinylated HWRRAHLLPRLP was coated on a preblocked streptavidin plate for 1 hour at room temperature. After a washing step different concentrations of HOCl-modified ATIII, or HOCl-modified alpha 1 antitrypsin (including negative control) were added for 1 hour at room temperature. After another washing step rabbit anti ATIII was added to misfolded antithrombin and rabbit anti alpha 1 antitrypsin antibody was added to misfolded alpha 1 antitrypsin for 1 hour at room temperature. After another washing step the corresponding secondary antibody, anti rabbit IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 13).

Figure 14:
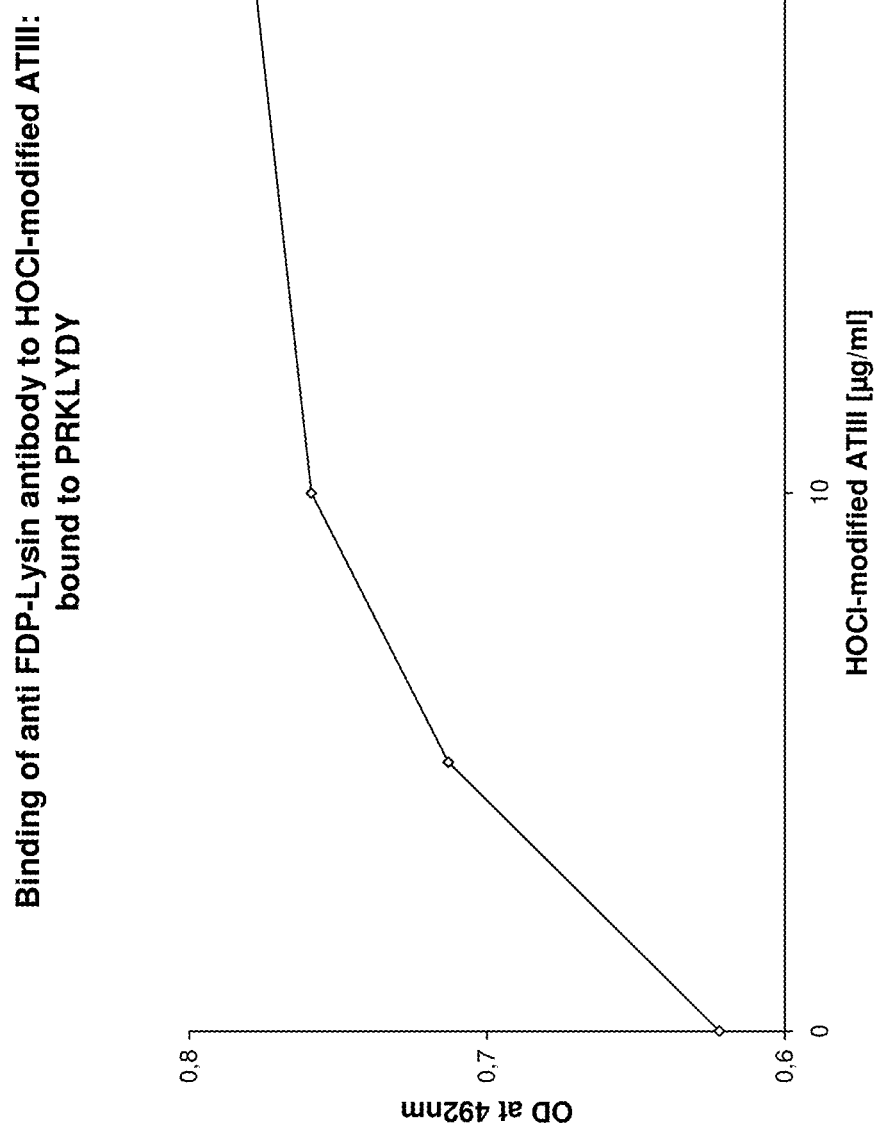
FIG. 14 shows the result of the measurement of the optical density at 492 nm for the binding of anti FDP-Lysine antibody to HOCl-modified ATIII bound to the peptide PRKLYDY respectively HWRRAHLLPRLP from example 5.

5. Detection and Measurement of Misfolded Proteins, which Carry FDP-Lysine Residues by Use of Biotin-PRKLYDY and HWRRAHLLPRLP-Biotin Biotinylated HWRRAHLLPRLP or biotinylated PRKLYDY was coated on a preblocked streptavidin plate for 1 hour at room temperature. After a washing step different concentrations misfolded proteins (including negative control) were added for 1 hour at room temperature (here as example HOCl-modified albumin and HOCl-modified antithrombin). After another washing step mouse anti FDP-Lysine antibody was added for 1 hour at room temperature. After another washing step the corresponding secondary antibody, anti mouse IgG POD, was added for 1 hour at room temperature. After a final washing step it was stained with o-phenylenediamine-substrate and the reaction was stopped after 30 min with 4 N sulphuric acid. The optical density was measured at 492 nm (FIG. 14).

6. Detection and Measurement of Misfolded Proteins in Complex with Alpha 2 Macroglobulin, Clustrin, Soluble GRP78, Haptoglobin Biotinylated HWRRAHLLPRLP or biotinylated PRKLYDY was coated on a preblocked streptavidin plate for 1 hour at room temperature. Factor VIIa, or fibrinogen, or HOCl-modified Albumin were incubated in solution with alpha 2 macroglobulin, or Clustrin, or GRP78, or haptoglobin, or human plasma and after that added in different concentrations (including negative control) for 1 hour at room temperature to the immobilised peptides. After another washing step rabbit anti alpha 2 macroglobulin, or rat anti clustrin, or rabbit anti GRP78/BiP or mouse anti haptoglobin was added for 1 hour at room temperature. After another washing step the corresponding secondary antibody, coupled to peroxidase, was added for 1 hour at room. After a final washing step it was stained with o-phenylenediamine-substrate and the reaction was stopped after 30 min with 4 N sulfuric acid. The optical density was measured at 492 nm.

7. Detection and Measurement of Misfolded Proteins/Peptides (Total) by Surface Plasmon Resonance Biotinylated PRKLYDY or biotinylated HWRRAHLLPRLP in borate buffer was bound in a Biacore 1000 machine to a sensor chip, on which streptavidin was covalently coupled to a 2D carboxymethyldextransulfate surface (SCB SAP). Different misfolded proteins were added with a flow rate of 10 µl/ml to the surfaces coupled with the peptides and their binding was visualized by an increase of response units.

8. Detection and Measurement of Misfolded Proteins/Peptides (Total) in Body Fluids by Surface Plasmon Biotinylated PRKLYDY or biotinylated HWRRAHLL-PRLP in borate buffer was bound in a Biacore 1000 machine to a sensor chip, on which streptavidin was covalently coupled to a 2D carboxymethyldextransulfate surface (SCB SAP). Different body fluids were added with a flow rate of 5 µl/ml to the surfaces coupled with the peptides and the binding of misfolded proteins was visualized by an increase of response units.

9. Comparison of the Amount of Misfolded Proteins in Plasma of Healthy Probands and in Blood of Patients (Examples: Acute Myocardial Infarction, Acute Stroke, Poorly Regulated Diabetes, Alzheimer's Disease, Sepsis, DIC)

Fresh plasma was made by centrifugation from blood of patients (here as example acute myocardial infarction, acute stroke, poorly regulated diabetes, Alzheimer's disease, sepsis, DIC). Parallel to this biotinylated PRKLYDY or biotinylated HWRRAHLLPRLP was coated to a preblocked streptavidin plate for 1 hour at room temperature.

The fresh plasma of the patients was incubated with the immobilised peptides for 1 hour at room temperature. After a washing step rabbit anti fibrinogen, or rabbit anti human albumin, or rabbit anti antithrombin was added for 1 hour at room temperature. After another washing step the corresponding secondary antibody, coupled to peroxidase, was added for 1 hour at room. After a final washing step it was stained with o-phenylenediamine-substrate and the reaction was stopped after 30 min with 4 N sulphuric acid. The optical density was measured at 492 nm and the amount of misfolded protein (here examined: misfolded fibrinogen, misfolded human albumin, misfolded antithrombin) was identified.

10. Detection and Measurement of Misfolded Proteins in Protein-/Peptide Containing Drugs Examples
  a) misfolded FVIIa
  b) misfolded fibrinogen
  c) misfolded FVIII
  d) misfolded insulin
  e) misfolded C1 inhibitor
  f) misfolded GM-CSF
  g) misfolded proteins in blood products (examples: PPSB, FEIBA, stored plasmas, coagulation factor concentrates, immunoglobulin concentrates, human albumin)

Figure 15:
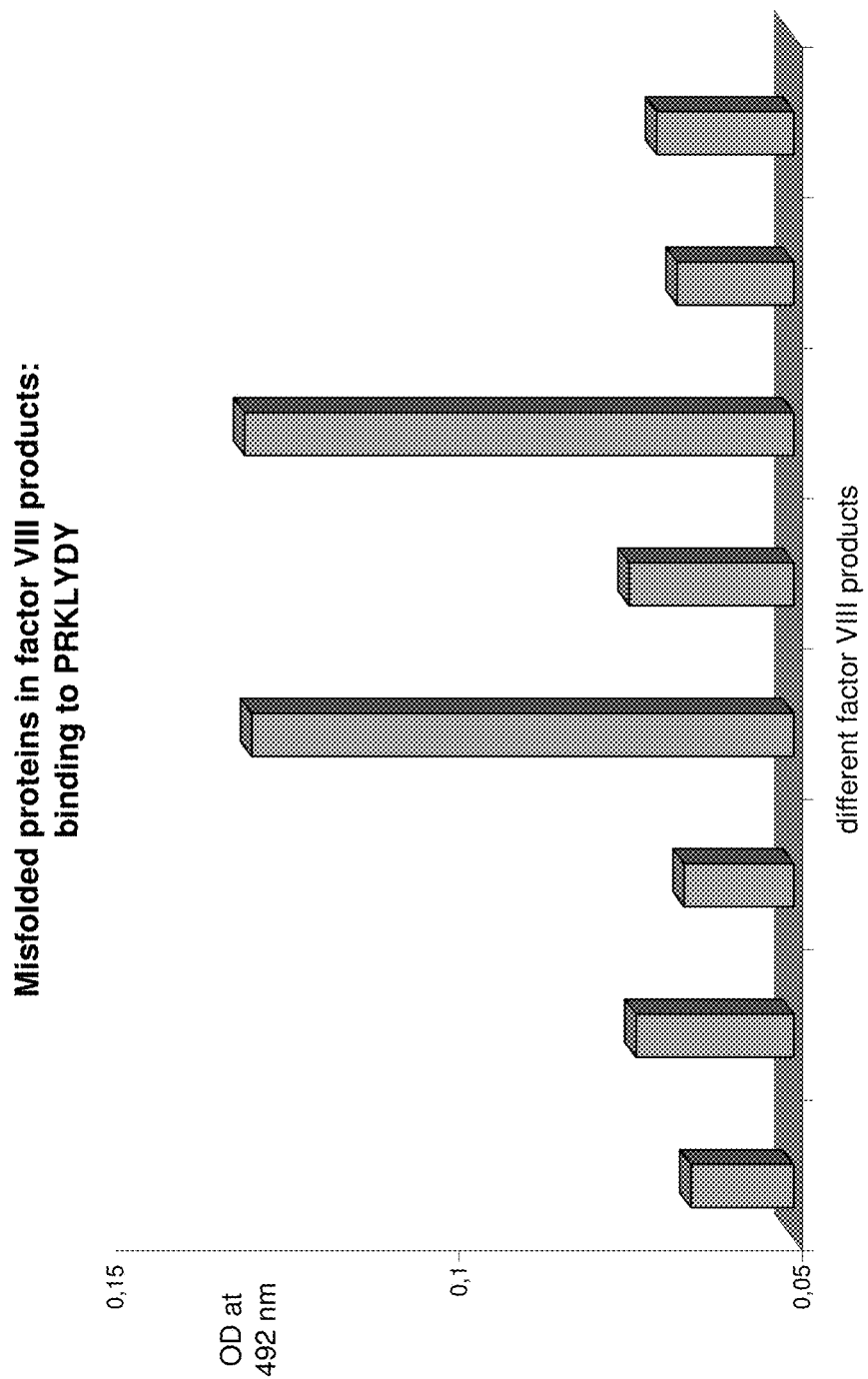
FIG. 15 shows the result of the measurement of the optical density at 492 nm of different misfolded proteins in factor VIII products to the peptides PRKLYDY respectively HWRRAHLLPRLP from example 10.

Biotinylated HWRRAHLLPRLP or biotinylated PRKLYDY was coated on a preblocked streptavidin plate for 1 hour at room temperature. Drugs containing a) factor VIIa, b) fibrinogen, c) FVIII, d) insulin, e) C1-inhibitor, f) GM-CSF g) different proteins from blood products (here examined PPSB-concentrates, coagulation factor concentrates, stored plasmas, immunoglobulin concentrates, human albumin supplements) were incubated for 1 hour at room temperature with the immobilised peptides. After a washing step in factor VIIa products anti FVIIa antibody, in fibrinogen products anti fibrinogen antibody, in FVIII-products anti FVIII-antibody, in insulin products anti insulin-antibody, in C1-inhibitor-products anti C1-inhibitor-antibody, in GM-CSF anti GM-CSF-antibody and in blood products several specific antibodies were added for 1 hour at room temperature. After another washing step the corresponding secondary antibody, coupled to peroxidase was added for 1 hour at room temperature. After a final washing step it was stained with o-phenylenediamine-substrate and the reaction was stopped after 30 min with 4 N sulphuric acid. The optical density was measured at 492 nm and the amount of misfolded protein in the drugs was identified (FIG. 15).

Misfolded proteins in drugs/blood products were parallel examined in surface plasmon resonance. For that purpose biotinylated PRKLYDY or biotinylated HWRRAHLLPRLP in borate buffer was bound in a Biacore 1000 machine to a sensor chip, on which streptavidin was covalently coupled to a 2D carboxymethyldextransulfate surface (SCB SAP). Different drugs were added with a flow rate of 5 µl/ml to the surfaces coupled with the peptides and the binding of misfolded proteins in the drugs/blood products was visualized by an increase of response units.

11. Influence of Treatment Conditions on the Concentration of Misfolded Proteins in Protein-/Peptide Containing Drugs Examples: Fibrinogen and FVIIa
  a) multiple freezing and thawing
  b) presence of $Ca^{++}$
  c) influence of minimal amounts of thrombin
  d) vortexing
  e) heating to 45 degrees for 24 h
  Fibrinogen and factor VIIa were a) 20 times freezing at −80° C. and thawed, b) added 2 mM $Ca^{2+}$ and incubated for 24 hours, c) added for 1 h 0.05 U/ml alpha thrombin, d) vortexed for 2 hours or e) heated for 24 hours to 45° C.

These different treated proteins were added to biotinylated HWRRAHLLPRLP or biotinylated PRKLYDY, coated before on a streptavidin preblocked plate for 1 hour at room temperature. After a washing step rabbit anti fibrinogen was added to the fibrinogen samples and sheep anti FVIIa to the factor VIIa samples for 1 hour at room temperature. After another washing step the corresponding secondary antibody, anti rabbit IgG POD or anti sheep IgG POD, was added for 1 hour at room temperature. After a final washing step it was stained with o-phenylenediamine-substrate and the reaction was stopped after 30 min with 4 N sulphuric acid. The optical density was measured at 492 nm.

12. Detection and Measurement of Misfolded Proteins in Reagents Generally Used in Diagnostics Examples
  a) avidin, streptavidin, neutravidin
  b) BSA
  c) skimmed milk powder (plasmon resonance)
  d) secondary antibodies Misfolded proteins in avidin, streptavidin, neutravidin, or in bovine serum albumin, or skimmed milk powder, or in secondary antibodies were examined in plasmon resonance parallel. For that purpose biotinylated PRKLYDY or biotinylated HWRRAHLLPRLP in borate buffer was bound in saturating concentrations in a Biacore 1000 machine to a sensor chip, on which streptavidin was covalently coupled to a 2D carboxymethyldextransulfate surface (SCB SAP). All free biotin binding points were capped. To this surfaces coupled with the peptides the substances above mentioned were added with a flow rate of 5 µl/min and the binding of misfolded proteins in diagnostic reagents visualized by an increase of response units.

13. Detection and Measurement of Misfolded Proteins in Reagents Often Used in Science a) fetal calve serum (FCS), newborn calve serum (NCS),
b) human serum
c) protein-containing/peptide-containing cell culture medium supplements Misfolded proteins in fetal calve serum, or newborn calve serum, or human serum, or protein-containing/peptide-containing cell culture medium supplements were examined parallel in plasmon resonance.

For that purpose biotinylated PRKLYDY or biotinylated HWRRAHLLPRLP in borate buffer was bound in a Biacore 1000 machine to a sensor chip, on which streptavidin was covalently coupled to a 2D carboxymethyldextransulfate surface (SCB SAP). Different science reagents were added with a flow rate of 5 µ/ml to the surfaces coupled with the peptides and the binding of misfolded proteins in the science reagents was visualized by an increase of response units.

14. Detection and Measurement of Misfolded Proteins/Peptides in Biofilms a) undefined biofilms attrited from teeth
b) undefined biofilms on stale, nutrition rich water (floral water after removal of the flowers, for example)
c) biofilms of *S. aureus*
d)

The biofilms, developing over the time, were transferred to sheets, where they can effectively adhere. To these sheets biotinylated PRKLYDY or biotinylated HWRRAHLLPRLP was added and incubated for 1 hour at room temperature. Afterwards a thoroughly washing step was done and the samples were analysed in two different manners:
1) Avidin-peroxidase was added for 1 hour at room temperature, and after washing peroxidase substrate was added. After 30 minutes incubation time the reaction was stopped with 4 N sulphuric acid, the coloured supernatant was transferred to an ELISA-plate and the optical density was measured at 492 nm. With negative controls and standard curves the amount of misfolded proteins/peptides was determined.
2) Avidin-FITC was added for 1 hour at room temperature and examined after a washing step in a fluorescence microscope.

15. Hemocompatibility of Materials

Comparison Polystyrol, TiO2-Specimens, with Protective Substance Treated TiO2 specimens
a) On the blood of a healthy donor, that was added to the different materials (specimens), shear stress was induced for 5 minutes (cone-and-plate aggregometer, $1700 \, s^{-1}$) (for control experiments the blood was in contact with the surfaces only under static conditions). The blood was carefully removed and incubated with biotinylated PRKLYDY, respectively with biotinylated HWRRAHLLPRLP. After another washing step the incubation was done with avidin peroxidase for 1 hour at room temperature. After another washing step peroxidase substrate was added and the reaction was stopped after 30 min with 4 N sulphuric acid. The optical density was measured at 492 nm.

With Negative Controls and Standard Curves the Amount of Misfolded Proteins/Peptides was Determined The activation status of the platelets and the leukocytes from the carefully removed blood was examined (binding of fibrinogen, anti CD62P, anti CD63, microparticles, microaggregates, Mac-1 expression and platelet-monocyte-associates), and the plasma was examined for complement fragments, kallekrein and classic coagulation parameters.

b) A fibrinogen solution was added to the specimens and sheared for 5 minutes at $1700s^{-1}$. After a washing step they were incubated with biotinylated PRKLYDY or biotinylated HWRRAHLLPRLP for 1 hour at room temperature. After another washing step an incubation for 1 hour with avidin peroxidase was done. After another washing step peroxidase substrate was added and the reaction was stopped after 30 minutes with 4 N sulphuric acid. The coloured supernatant was transferred to an ELISA-plate and the optical density was measured at 492 nm. With negative controls and standard curves the amount of misfolded fibrinogen was determined.

16. Optimization of Medical Devices

Example: heart assist pumps
Blood of healthy blood donors was each filled in two different systems with heart assist devices and pumped through the cycles for a defined time period. Before as well as 4 hours after the XXXXX 5 ml blood was taken and plasma was generated by centrifugation.

Parallel for that purpose biotinylated HWRRAHLLPRLP or biotinylated PRKLYDY was coated on a preblocked streptavidin plate for 1 hour at room temperature.

Figure 16:
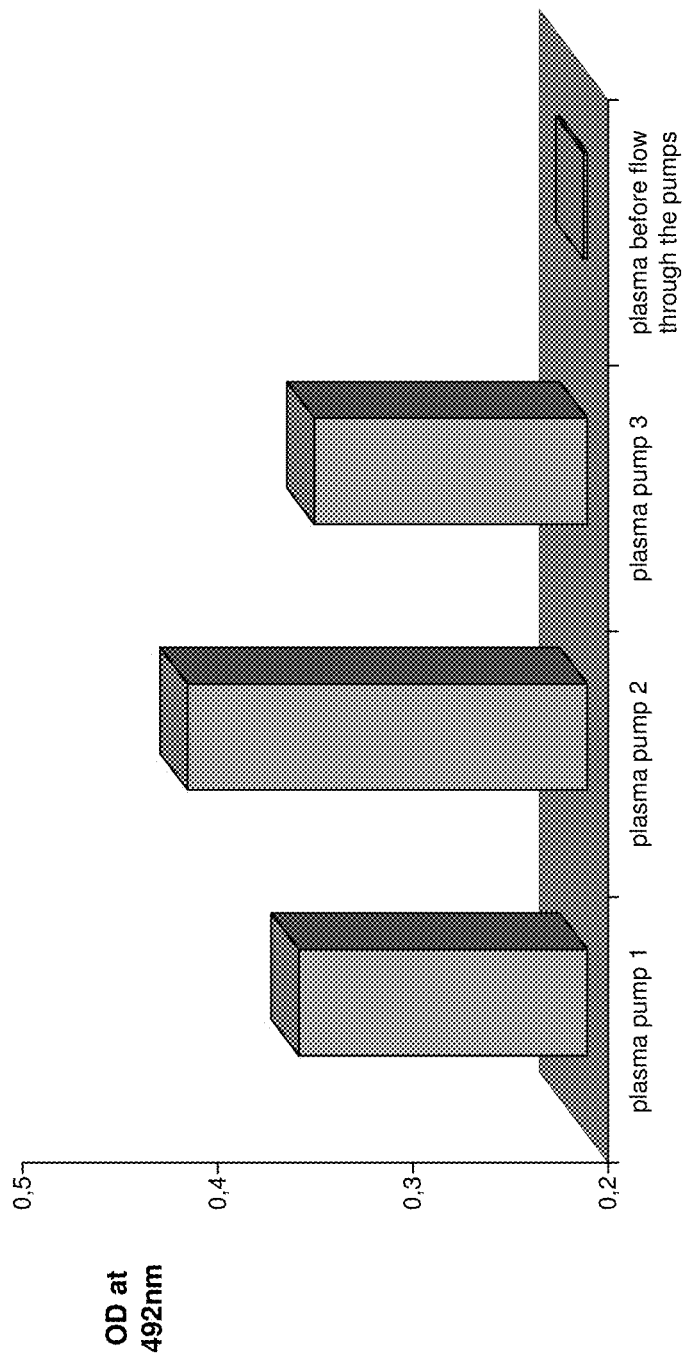
FIG. 16 shows the result of the measurement of the optical density at 492 nm of different misfolded proteins/peptides, generated by flow through heart assist devices depending on the constitution of the heart pumps. The measurement was conducted by binding to the peptides PRKLYDY respectively HWRRAHLLPRLP.
Figure 16:
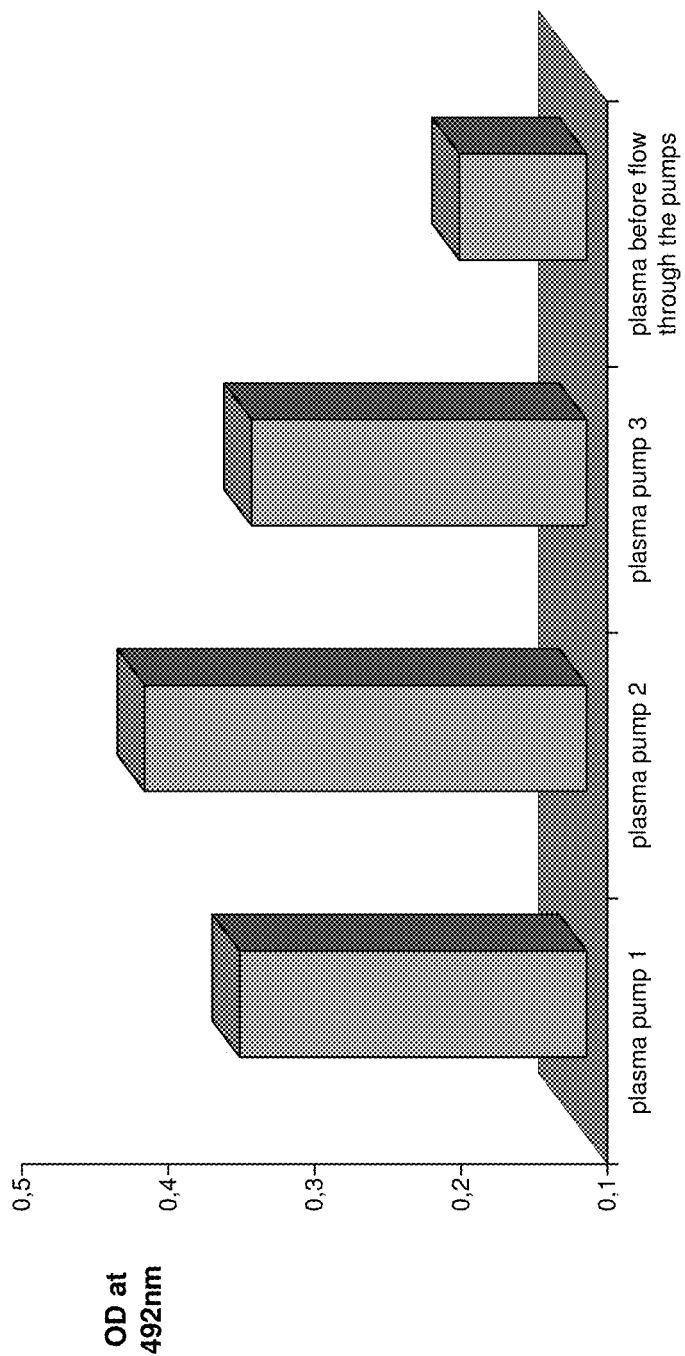

The fresh plasmas were incubated with the immobilized peptides for 1 hour at room temperature. After a washing step either rabbit anti fibrinogen, or rabbit anti human albumin, or rabbit anti antithrombin III was added for 1 hour at room temperature. After another washing step the corresponding secondary antibody, coupled to peroxidase was added for 1 hour at room temperature. After a final washing step it was stained with o-phenylenediamine-substrate and the reaction was stopped after 30 min with 4 N sulphuric acid. The optical density was measured at 492 nm and the amount of misfolded proteins (here examined: misfolded fibrinogen, misfolded human albumin, misfolded antithrombin) was identified. The less misfolded proteins were found, the better the heart assist device was designed (FIG. 16).

17. Binding of Microorganisms to HWRRAHLLPRLP-Biotin and Biotin-PRKLYDY

Biotinylated HWRRAHLLPRLP or biotinylated PRKLYDY was coated to a preblocked streptavidin plate for 1 hour at room temperature. After a washing step bacterial cultures, bacterial mixtures, *Staphylococcus aureus* or *Candida albicans* were added to the immobilised peptides (as negative control the microorganisms were added to plastic, where no peptides were coated) and incubated for 1 hour at room temperature. After a thoroughly washing step with PBS-buffer the adhered cells were a) directly and b) after 1 hour coloured.

18. Binding of Misfolded Proteins/Peptides Serving as Precursors for Technical Useful Amyloids Biotinylated HWRRAHLLPRLP or biotinylated PRKLYDY was coated to a preblocked streptavidin plate for 1 hour at room temperature. After a washing step with PBS-buffer solutions of biomaterials were added to the immobilized peptides, which could contain potential misfolded proteins/peptides. As an example we artificially spiked such a solution with potential materials, namely poly(ValGlyGlyLeuGly) or poly(ValGlyGlyValGly) (both materials are already technical used, covered by the application). The peptides according to the invention were able to bind both materials, as shown with surface plasmon resonance.

Bound peptides, proteins or protein fragments can be dissolved from such chips or other solid materials, on which our analytical substances were immobilised, and can be identified via proteomic techniques, well known to experts.

REFERENCES

1. Stefani M. Generic cell dysfunction in neurodegenerative disorders: role of surfaces in early protein misfolding, aggregation, and aggregate cytotoxicity. *Neuroscientist.* 2007 October; 13(5):519-31
2. Zhen Xu, Xi-Wei Liu, Yin-Sheng Ma and Hong-Wen Gao. Interaction of nano-$TiO_2$ with lysozyme: insights into the enzyme toxicity of nanosized particles. *Environ Sci Pollut Res Int.* 2010 March; 17(3):798-806. Epub 2009 Apr. 24.
3. Onoue S, Ohshima K, Debari K, Koh K, Shioda S, Iwasa S, Kashimoto K, Yajima T. Mishandling of the therapeutic peptide glucagon generates cytotoxic amyloidogenic fibrils. Pharm. Res. 21:1274-1283
4. Bouma B, Kroon-Batenburg L M, Wu Y P, Brünjes B, Posthuma G, Kranenburg O, de Groot P G, Voest E E, Gebbink M F. Glycation induces formation of amyloid cross-beta structure in albumin. J Biol Chem 2003; 278: 41810-9
5. Maas C, Govers-Riemslag J W, Bouma B, Schiks B, Hazenberg B P, Lokhorst H M, Hammarström P, ten Cate H, de Groot P G, Bouma B N, Gebbink M F. Misfolded proteins activate Factor XII in humans, leading to kallikrein formation without initiating coagulation. J Clin Invest. 2008; 118(9):3208-3218)
6. Rakhit R, Cunningham P, Furtos-Matei A, Dahan S, Qi X F, Crow J P, Cashman N R, Kondejewski L H, Chakrabartty A. Oxidation-induced Misfolding and Aggregation of Superoxide Dismutase and Its Implications for Amyotrophic Lateral Sclerosis, J Biol Chem 2002; 277 (49), 47551-47556
7. Marina Ramirez-Alvarado, Jeffery W. Kelly, Christopher M. Dobson, Johanna C. Scheinost, Daniel P. Witter, Grant E. Boldt, Paul Wentworth. Chapter 28. Role of Oxidative Stress in Protein Misfolding and/or Amyloid Formation. 2010
8. Hoffstrom B G, Kaplan A, Letso R, Schmid R S, Turmel G J, Lo D C, Stockwell B R. Inhibitors of protein disulfide isomerase suppress apoptosis induced by misfolded proteins. Nature Chemical Biology 2010; 6, 900-906
9. Park S Y, Ferreira A. The generation of a 17 kDa neurotoxic fragment: an alternative mechanism by which tau mediates beta-amyloid-induced neurodegeneration. J Neurosci 2005; 25:5365-75
10. Stewart N. Loh. The missing Zinc: p53 misfolding and cancer Metallomics, 2010, 2, 442-449
11. Byström R, Aisenbrey C, Borowik T, Bokvist M, Lindström F, Sani M A, Olofsson A, Gröbner G. Disordered proteins: biological membranes as two-dimensional aggregation matrices. *Cell Biochem Biophys.* 2008; 52(3):175-89
12. Taylor D R, Hooper N M. Role of lipid rafts in the processing of the pathogenic prion and Alzheimer's amyloid-beta proteins. *Semin Cell Dev Biol.* 2007 October; 18(5):638-48
13. Gebbink M F, Claessen D, Bouma B, Dijkhuizen L, Wösten H A. Amyloids—a functional coat for microorganisms. Nat Rev Microbiol 2005; 3:333-41
14. Horn M, Bertling A, Brodde M F, Schulte A, Roth J, Van Aaken H, Jurk K, Stürzel C, Heilmann C, Peters G, Kehrel B E. Human neutrophil alpha defensins activate platelets. Zur Publikation eingereicht
15. Levinthal J D, Rubin H. *Serum induced changes in the fine structure of primary chick embryo cultures.* 1968 Exp Cell Res. 1968 October; 52(2):667-72
16. Anfinsen, C B. Untersuchungen über die Ursachen der Faltung von Proteinketten (Nobel-Vortrag). Angewandte Chemie, 1973, 85: 1065-1074
17. Scott H. Protein-misfolding in neurodegenerative disease. The Internet Journal of Neurology. 2009 Volume 11 Number 2
18. Chelbi S T, Mondon F, Jammes H, Buffat C, Mignot T M, Tost J, Busato F, Gut I, Rebourcet R, Laissue P, Tsatsaris V, Goffinet F, Rigourd V, Carbonne B, Ferré F, Vaiman D. Expressional and Epigenetic Alterations of Placental Serine Protease Inhibitors SERPINA3 Is a Potential Marker of Preeclampsia. Hypertension. 2007; 49:76
19. Maas C, Hermeling S, Bouma B, Jiskoot W, Gebbink M F. A role for protein misfolding in immunogenicity of biopharmaceuticals. J Biol Chem 2007; 282:2229-36
20. Brignull H R, Morley J F, Morimoto R I. The stress of misfolded proteins: *C. elegans* models for neurodegenerative disease and aging. Adv. Exp. Med. Biol. 2007; 594, 167-189
21. Maas C, Schiks B, Strangi R D, Hackeng T M, Bouma B N, Gebbink M F, Bouma B. Identification of fibronectin type I domains as amyloid-binding modules on tissue-type plasminogen activator and three homologs. Amyloid 2008; 15:166-80
22. Maas C, Govers-Riemslad J W, Bouma B, Schiks B, Hazenberg B P, Lokhorst H M, Hammarström P, ten Cate H, de Groot P G, Bouma B N, Gebbink M F. Misfolded proteins activate factor XII in humans, leading to kallikrein formation without initiating coagulation. J Clin Invest 2008; 118:3208-18
23. Gebbink M F, Bouma B, Maas C, Bouma B N. Physiological responses to protein aggregates: Fibrinolysis, coagulation and inflammation (new roles for old factors). *FEBS Lett.* 2009 Aug. 20; 583(16):2691-9
24. Kranenburg O, Bouma B, Kroon-Batenburg L M, Reijerkerk A, Wu Y P, Voest E E, Gebbink M F. *Tissue-type plasminogen activator is a multiligand cross-beta structure receptor.* Current Biology 2002; 12, 1833-1839
25. Mintz P J, Kim J, Do K A, Wang X, Zinner R G, Cristofanilli M, Arap M A, Hong W K, Troncoso P, Logothetis C J, Pasqualini R, Arap W. Fingerprinting the circulating repertoire of antibodies from cancer patients. Nat. Biotechnol 2003; 21: 57-63
26. Liu C, Bhattacharjee G, Boisvert W, Dilley R, Edgington T. In vivo interrogation of the molecular display of atherosclerotic lesion surfaces. Am J Pathol 2003; 163: 1859-71
27. Zhou J, Werstuck G H, Lhoták S, de Koning A B, Sood S K, Hossain G S, Møller J, Ritskes-Hoitinga M, Falk E, Dayal S, Lentz S R, Austin R C. Association of multiple cellular stress pathways with accelerated atherosclerosis in hyperhomocysteinemic apolipoprotein E-deficient mice. Circulation 2004; 110: 207-213
28. Feaver R E, Hastings N E, Pryor A, Blackman B R. GRP78 upregulation by atheroprone shear stress via p38-, alpha2beta1-dependent mechanism in endothelial cells. ATVB 2008; 28: 1534-41

29. Chen J C, Wu M L, Huang K C, Lin W W. *HMG-CoA reductase inhibitors activate the unfolded protein response and induce cytoprotective GRP78 expression*. Cardiovasc. Res. 2008; 80: 138-150
30. Watson L M, Chan A K, Berry L R, Li J, Sood S K, Dickhout J G, Xu L, Werstuck G H, Bajzar L, Klamut H J, Austin R C. Overexpression of the 78-kda glucose-regulated protein/immunoglobulin-binding protein (GRP78/BIP) inhibits tissue factor procoagulant activity. J. Biol. Chem. 2003; 278:17438-17447
31. Bhattacharjee G, Ahamed J, Pedersen B, El-Sheikh A, Mackman N, Ruf W, Liu C, Edgington T S. Regulation of tissue factor-mediated initiation of the coagulation cascade by cell surface grp78. ATVB 2005; 25:1737-1743
32. Molins B, Peña E, Padro T, Casani L, Mendieta C, Badimon L. Glucose-regulated protein 78 and platelet deposition. ATVB 2010; 30: 1246-1252
33. Bertling A, Niemann S, Hussain M, Brodde M F, Pohl S, Schifferdecker T, Roth J, Jurk K, Müller A, Peters G, Heilmann C, Kehrel B E. Staphylococcal extracellular adherence protein (Eap) induces platelet adhesion, agglutination, aggregation and procoagulant activity. zur Publikation eingereicht
34. Herczenik E, Bouma B, Korporaal S J, Strangi R, Zeng Q, Gros P, Van Eck M, Van Berkel T J, Gebbink M F, Akkerman J W. Activation of Human Platelets by Misfolded Proteins. *Arterioscler Thromb Vasc Biol*. 2007 July; 27(7): 1657-65
35. Bertling A, Brodde M F, Van Aken H, Müller A, Hussain M, Roth J, Peters G, Heilmann C, Kehrel B E. Staphylococcal extracellular adherence protein (Eap) acts as a misfolded protein and interacts with the cell surface chaperone BiP. zur Publikation eingereicht
36. Horn M, Bertling A, Brodde M F, Schulte A, Roth J, Stürzel C, Heilmann C, Peters G, Van Aken H, Jurk K, Kehrel B E. Human neutrophil alpha-defensins activate platelets. zur Publikation eingereicht
37. Marcinowski M, Höller M, Feige M J, Baerend D, Lamb D C, Buchner J. Substrate discrimination of the chaperone BiP by autonomous and cochaperone-regulated conformational transitions. *Nat Struct Mol. Biol*. 2011 February; 18(2):150-8
38. Deng W G, Ruan K H, Du M, Saunders M A, Wu K K. Aspirin and salicylate bind to immunoglobulin heavy chain binding protein (BiP) and inhibit its ATPase activity in human fibroblasts. *FASEB J.* 2001 November; 15(13):2463-70
39. Sugiyama S, Kugiyama K, Aikawa M, Nakamura S, Ogawa H, Libby P. Hypochlorous Acid, a Macrophage Product, Induces Endothelial Apoptosis and Tissue Factor Expression. Involvement of Myeloperoxidase-Mediated Oxidant in Plaque Erosion and Thrombogenesis. Arterioscler Thromb Vasc Biol. 2004; 1309-1314
40. Baldus S, Heeschen C, Meinertz T, Zeiher A M, Eiserich J P, Münzel T, Simoons M L, Hamm C W; *CAPTURE Investigators*. Circulation Myeloperoxidase Serum Levels Predict Risk in Patients With Acute Coronary Syndromes. *Circulation*. 2003 Sep. 23; 108(12):1440-5
41. Matthijsen R A, Huugen D, Hoebers N T, de Vries B, Peutz-Kootstra C J, Aratani Y, Daha M R, Tervaert J W, Buurman W A, Heeringa P. Myeloperoxidase Is Critically Involved in the Induction of Organ Damage after Renal Ischemia Reperfusion Am. J. Pathol. 2007; 171(6): 1743-1752
42. Meuwese M C, Stroes E S, Hazen S L, van Miert J N, Kuivenhoven J A, Schaub R G, Wareham N J, Luben R, Kastelein J J, Khaw K T, Boekholdt S M. Serum Myeloperoxidase Levels Are Associated With the Future Risk of Coronary Artery Disease in Apparently Healthy Individuals: The EPIC-Norfolk Prospective Population Study. J. Am. Coll. Cardiol, 2007; 50(2): 159-165
43. Mocatta T J, Pilbrow A P, Cameron V A, Senthilmohan R, Frampton C M, Richards A M, Winterbourn C C. Winterbourn Plasma Concentrations of Myeloperoxidase Predict Mortality After Myocardial Infarction. J. Am. Coll. Cardiol. 2007; 49(20): 1993-2000
44. Ferrante G, Nakano M, Prati F, Niccoli G, Mallus M T, Ramazzotti V, Montone R A, Kolodgie F D, Virmani R, Crea F. High Levels of Systemic Myeloperoxidase Are Associated With Coronary Plaque Erosion in Patients With Acute Coronary Syndromes: A Clinicopathological Study; Circulation, 2010; 122(24): 2505-2513
45. Brennan M L, Reddy A, Tang W H, Wu Y, Brennan D M, Hsu A, Mann S A, Hammer P L, Hazen S L. Comprehensive Peroxidase-Based Hematologic Profiling for the Prediction of 1-Year Myocardial Infarction and Death Circulation. 2010; 122(1): 70-79
46. Naruko T, Furukawa A, Yunoki K, Komatsu R, Nakagawa M, Matsumura Y, Shirai N, Sugioka K, Takagi M, Hozumi T, Itoh A, Haze K, Yoshiyama M, Becker A E, Ueda M. Increased expression and plasma levels of myeloperoxidase are closely related to the presence of angiographically-detected complex lesion morphology in unstable angina Heart. 2010; 96(21): 1716-1722
47. Van der Zwan L P, Scheffer P G, Dekker J M, Stehouwer C D, Heine R J, Teerlink T. Hyperglycemia and Oxidative Stress Strengthen the Association Between Myeloperoxidase and Blood Pressure. Hypertension. 2010; 55(6): 1366-1372
48. Giovannini S, Onder G, Leeuwenburgh C, Carter C, Marzetti E, Russo A, Capoluongo E, Pahor M, Bernabei R, Landi F. Myeloperoxidase Levels and Mortality in Frail Community-Living Elderly Individuals. J Gerontol A Biol Sci Med. Sci. 2010; 65A(4): 369-376
49. Ali Z, Sarcia P, Mosley T H Jr, Kondraqunta V, Kullo I J. Association of serum myeloperoxidase with the ankle-brachial index and peripheral arterial disease Vascular Medicine. 2009; 14(3): 215-220
50. Liu H R, Tao L, Gao E, Qu Y, Lau W B, Lopez B L, Christopher T A, Koch W, Yue T L, Ma X L. Rosiglitazone inhibits hypercholesterolaemia-induced myeloperoxidase upregulation—a novel mechanism for the cardioprotective effects of PPAR agonists. Cardiovasc Res. 2009; 81(2): 344-352
51. Rudolph V, Andrié R P, Rudolph T K, Friedrichs K, Klinke A, Hirsch-Hoffmann B, Schwoerer A P, Lau D, Fu X, Klingel K, Sydow K, Didié M, Seniuk A, von Leitner E C, Szoecs K, Schrickel J W, Treede H, Wenzel U, Lewalter T, Nickenig G, Zimmermann W H, Meinertz T, Böger R H, Reichenspurner H, Freeman B A, Eschenhagen T, Ehmke H, Hazen S L, Willems S, Baldus S. Myeloperoxidase acts as a profibrotic mediator of atrial fibrillation Nature Medicine. 2010; 16, 470-474
52. Tang W H, Wu Y, Nicholls S J, Hazen S L. Plasma Myeloperoxidase Predicts Incident Cardiovascular Risks in Stable Patients Undergoing Medical Management for Coronary Artery Disease. Clin. Chem. 2011; 57(1): 33-39
53. Davidson D J, Haskell C, Majest S, Kherzai A, Egan D A, Walter K A, Schneider A, Gubbins E F, Solomon L, Chen Z, Lesniewski R, Henkin J. Kringle 5 of Human Plasminogen Induces Apoptosis of Endothelial and Tumor Cells through Surface-Expressed Glucose-Regulated Protein 78. Cancer Res. 2005; 65(11): 4663-72

54. McFarland B C, Stewart J Jr, Hamza A, Nordal R, Davidson D J, Henkin J, Gladson C L. Plasminogen kringle 5 induces apoptosis of brain microvessel endothelial cells: sensitization by radiation and requirement for GRP78 and LRP1. *Cancer Res.* 2009 Jul. 1; 69(13):5537-45

55. Raiter A, Weiss C, Bechor Z, Ben-Dor I, Battler A, Kaplan B, Hardy B. Activation of GRP78 on endothelial cell membranes by an ADAM15-derived peptide induces angiogenesis. *J Vasc Res.* 2010; 47(5):399-411

56. Misra U K, Pizzo S V. Heterotrimeric Galphaq11 co-immunoprecipitates with surface-anchored GRP78 from plasma membranes of alpha2M*-stimulated macrophages. J cell Biochem. 2008; 104, 96-104

57. Lu M C, Lai N S, Yu H C, Huang H B, Hsieh S C, Yu C L. Anti-citrullinated protein antibodies bind surface-expressed citrullinated Grp78 on monocyte/macrophages and stimulate tumor necrosis factor αproduction. *Arthritis Rheum.* 2010 May; 62(5):1213-23.

58. Reijerkerk A, Mosnier L O, Kranenburg O, Bouma B N, Carmeliet P, Drixler T, Meijers J C, Voest E E, Gebbink M F. Amyloid endostatin induces endothelial cell detachment by stimulation of the plasminogen activation system. *Mol Cancer Res.* 2003 June; 1(8):561-8

59. Zhang Y, Liu R, Ni M, Gill P, Lee A S. Cell Surface Relocalization of the Endoplasmic Reticulum Chaperone and Unfolded Protein Response Regulator GRP78/BiP J. Biol. Chem. 2010; 285:15065-15075

60. Hotamisligil G S. Endoplasmic reticulum stress and atherosclerosis. Nature Medicine 2010; 16, 396-399

61. Myoishi M, Hao H, Minamino T, Watanabe K, Nishihira K, Hatakeyama K, Asada Y, Okada K, Ishibashi-Ueda H, Gabbiani G, Bochaton-Piallat M, Mochizuki N, Kitakaze M. Increased endoplasmic reticulum stress in atherosclerotic plaques associated with acute coronary syndrome. Circulation. 2007; 116: 1226-1233

62. Zhou J, Lhoták S, Hilditch B A, Austin R C. Activation of the unfolded protein response occurs at all stages of atherosclerotic lesion development in apolipoprotein E-deficient mice. Circulation. 2005; 111: 1814-1821, 63. Özcan U, Yilmaz E, Özcan L, Furuhashi M, Vaillancourt E, Smith R O, Gorgun C Z, Hotamisligil G S. Chemical chaperones reduce ER stress and restore glucose homeostasis in a mouse model of type 2 diabetes. Science. 2006; 313: 1137-1140

64. Feaver R E, Hastings N E, Pryor A, Blackman B R. GRP78 upregulation by atheroprone shear stress via p38-, alpha2beta1-dependent mechanism in endothelial cells. *Arterioscler Thromb Vasc Biol.* 2008 August; 28(8):1534-41

65. Ye R, Jung D Y, Jun J Y, Li J, Luo S, Ko H J, Kim J K, Lee A S. Grp78 Heterozygosity Promotes Adaptive Unfolded Protein Response and Attenuates Diet-Induced Obesity and Insulin Resistance. *Diabetes.* 2010 January; 59(1):6-16

66. Dickhout J G, Colgan S M, Lhoták S, Austin R C. Increased Endoplasmic Reticulum Stress in Atherosclerotic Plaques Associated With Acute Coronary Syndrome A Balancing Act Between Plaque Stability and Rupture. *Circulation.* 2007 Sep. 11; 116(11):1214-6

67. Wilson M R, Yerbury J J, Poon S. Potential roles of abundant extracellular chaperones in the control of amyloid formation and toxicity. Mol. BioSyst. 2008; 4, 42-52

68. Naiki H, Nagai Y. Molecular Pathogenesis of Protein Misfolding Diseases: Pathological Molecular Environments Versus Quality Control Systems Against Misfolded Proteins. J. Biochem. 2009; 146 (6): 751-756

69. Yerbury J J, Rybchyn M S, Easterbrook-Smith S B, Henriques C, Wilson M R. The acute phase protein haptoglobin is a mammalian extracellular chaperone with an action similar to clusterin. Biochemistry 2005; 44: 10914-10925

70. Yerbury J J, Stewart E M, Wyatt A R, Wilson M R. Quality control of protein folding in extracellular space. EMBO Reports 2005; 6: 1131-1136

71. Wilhelmus M M, de Waal R M, Verbeek M M. Heat Shock Proteins and Amateur Chaperones in Amyloid-Beta Accumulation and Clearance in Alzheimer's Disease. Mol. Neurobiol. 2007 June; 35(3): 203-216

72. Strittmatter W J, Saunders A M, Schmechel D, Pericak-Vance M, Enghild J, Salvesen G S, Roses A D. Apolipoprotein E: high-avidity binding to beta-amyloid and increased frequency of type 4 allele in late-onset familial Alzheimer disease. Proc Natl Acad Sci USA 1993; 90:1977-1981

73. Strittmatter W J, Weisgraber K H, Huang D Y, Dong L M, Salvesen G S, Pericak-Vance M, Schmechel D, Saunders A M, Goldgaber D, Roses A D. Binding of human apolipoprotein E to synthetic amyloid beta peptide: isoform-specific effects and implications for late-onset Alzheimer disease. Proc Natl Acad Sci USA 1993; 90:8098-8102

74. Casserly I, Topol E. Convergence of atherosclerosis and Alzheimer's disease: inflammation, cholesterol, and misfolded proteins, Lancet 2004; 363:1139-46

75. Baldus S, Heeschen C, Meinertz T, Zeiher A M, Eiserich J P, Münzel T, Simoons M L, Hamm C W; *CAPTURE Investigators.* Myeloperoxidase Serum Levels Predict Risk in Patients With Acute Coronary Syndromes. *Circulation.* 2003 Sep. 23; 108(12):1440-5

76. Mallat Z, Lambeau G, Tedgui A. Lipoprotein-Associated and Secreted Phospholipases A2 in Cardiovascular Disease Roles as Biological Effectors and Biomarkers. *Circulation.* 2010 Nov. 23; 122(21):2183-200

77. Greco G, Balogh G, Brunelli R, Costa G, De Spirito M, Lenzi L, Mei G, Ursini F, Parasassi T. Generation in Human Plasma of Misfolded, Aggregation-Prone Electronegative Low Density Lipoprotein. *Biophys J.* 2009 Jul. 22; 97(2):628-35

78. Matsuzaki T, Sasaki K, Tanizaki Y, Hata J, Fujimi K, Matsui Y, Sekita A, Suzuki S O, Kanba S, Kiyohara Y, Iwaki T. Insulin resistance is associated with the pathology of Alzheimer disease: the Hisayama study. *Neurology.* 2010 Aug. 31; 75(9):764-70

79. Ho L, Qin W, Pompl P N, Xiang Z, Wang J, Zhao Z, Peng Y, Cambareri G, Rocher A, Mobbs C V, H of P R, Pasinetti G M. Diet-induced insulin resistance promotes amyloidosis in a transgenic mouse model of Alzheimer's disease. *FASEB J.* 2004 May; 18(7):902-4

80. Sie M P, van der Wiel H E, Smedts F M, de Boer A C. Human recombinant insulin and amyloidosis: an unexpected association. *Neth J. Med.* 2010 March; 68(3):138-40

81. Yumlu S, Barany R, Eriksson M, Röcken C. Localized insulin-derived amyloidosis in patients with diabetes mellitus: a case report. Hum Pathol. 2009; 40(11):1655-60

82. Brange J, Andersen L, Laursen E D, Meyn G, Rasmussen E. Toward understanding insulin fibrillation. *J Pharm Sci.* 1997 May; 86(5):517-25

83. Ratner R E, Phillips T M, Steiner M. *Persistent cutaneous insulin allergy resulting from high-molecular-weight insulin aggregates.* Diabetes. 1990 June; 39(6):728-33

84. Xu S. *Aggregation drives "misfolding" in protein amyloid fiber formation.* Amyloid. 2007 June; 14(2):119-31.

85. Maurer-Stroh S, Debulpaep M, Kuemmerer N, Lopez de la Paz M, Martins I C, Reumers J, Morris K L, Copland A, Serpell L, Serrano L, Schymkowitz J W, Rousseau F. Exploring the sequence determinants of amyloid structure using position-specific scoring matrices. *Nat. Methods.* 2010 March; 7(3):237-42

86. Puchtler H, Sweat F, Levine M. On the binding of Congo red by amyloid. J Histochem Cytochem 1962; 10: 355-64
87. Westermark G T, Johnson K H, Westermark P. Staining methods for identification of amyloid in tissue. Meth Enzymol 1999; 309: 3-25
88. Merlini G, Bellotti V. Molecular mechanisms of amyloidosis. N Engl J Med 2003; 349: 583-596
89. Merlini G, Westermark P. The systemic amyloidoses: clearer understanding of the molecular mechanisms offers hope for more effective therapies. *J Intern Med.* 2004 February; 255(2):159-78
90. Glenner G G, Terry W, Harada M, Isersky C, Page D. Amyloid fibril proteins: proof of homology with immunoglobulin light chains by sequence analysis. Science 1971; 172: 1150-1
91. Gillmore J D, Lovat L B, Persey M R, Pepys M B, Hawkins P N. Amyloid load and clinical outcome in AA amyloidosis in relation to circulating concentration of serum amyloid A protein. Lancet 2001; 358: 24-9
92. Westermark P, Sletten K, Johansson B, Cornwell G G III. Fibril in senile systemic amyloidosis is derived from normal transthyretin. Proc Natl Acad Sci USA 1990; 87: 2843-5
93. Obici L, Bellotti V, Mangione P, Stoppini M, Arbustini E, Verga L, Zorzoli I, Anesi E, Zanotti G, Campana C, Viganò M, Merlini G. The new apolipoprotein A-I variant Leu (174)->Ser causes hereditary cardiac amyloidosis, and the amyloid fibrils are constituted by the 93-residue N-terminal polypeptide. Am J Pathol 1999; 155: 695-702
94. Kayed R, Bernhagen J, Greenfield N, Sweimeh K, Brunner H, Voelter W, Kapurniotu A. Conformational transitions of islet amyloid polypeptide (IAPP) in amyloid formation in vitro. J Mol Biol 1999; 287: 781-96
95. Janson J, Ashley R H, Harrison D, McIntyre S, Butler P C. The mechanism of islet amyloid polypeptide toxicity is membrane disruption by intermediate-sized toxic amyloid particles. Diabetes 1999; 48: 491-8
96. Benson M D. LECT2 amyloidosis. Kidney Int. 2010 May; 77(9):757-9.
97. Selkoe D J. The origins of Alzheimer disease: a is for amyloid. JAMA 2000; 283: 1615-7
98. Cohen F E, Pan K-M, Huang Z, Baldwin M, Fletterick R J, Prusiner S B. Structural clues to prion replication. Science 1994; 264: 530-1
99. Wille H, Baldwin M A, Cohen F E, DeArmond S J, Prusiner S B. Prion protein amyloid: separation of scrapie infectivity from PrP polymers. Ciba Found Symp. 1996; 199:181-99; discussion 199-201.
100. Chichester: John Wiley & Sons, 1996; 181-201
101. Drüeke T B. Beta2-microglobulin and amyloidosis. Nephrol Dial Transplant. 2000; 15 Suppl 1:17-24
102. Wilson M R, Yerbury J J, Poon S. Potential roles of abundant extracellular chaperones in the control of amyloid formation and toxicity. *Mol. Biosyst.* 2008 January; 4(1):42-52
103. Herczenik E, Bouma B, Korporaal S J, Strangi R, Zeng Q, Gros P, Van Eck M, Van Berkel T J, Gebbink M F, Akkerman J W. Activation of Human Platelets by Misfolded Proteins. Arterioscler Thromb Vasc Biol. 2007 July; 27(7):1657-65
104. Sweeny J M, Gorog D A, Fuster V. *Antiplatelet drug 'resistance'. Part 1: mechanisms and clinical measurements.* Nat Rev Cardiol. 2009 April; 6(4):273-82
105. Henry P, Vermillet A, Boval B, Guyetand C, Petroni T, Dillinger J G, Sideris G, Bal Dit Sollier C, Drouet L. 24-hour time-dependent aspirin efficacy in patients with stable coronary artery disease. *Thromb Haemost.* 2011 Feb. 1; 105(2):336-44.
106. Rothwell P M, Fowkes F G, Belch J F, Ogawa H, Warlow C P, Meade T W. Effect of daily aspirin on long-term risk of death due to cancer: analysis of individual patient data from randomised trials. *Lancet.* 2011 Jan. 1; 377(9759): 31-41
107. Topol E J, Schork N J. Catapulting clopidogrel pharmacogenomics forward. *Nat. Med.* 2011 January; 17(1):40-1
108. Bouman H J, Schömig E, van Werkum J W, Velder J, Hackeng C M, Hirschhäuser C, Waldmann C, Schmalz H G, ten Berg J M, Taubert D. Paraoxonase-1 is a major determinant of clopidogrel efficacy. *Nat. Med.* 2011 January; 17(1):110-6
109. Sutherland W H, de Jong S A, Walker R J. Hypochlorous acid and low serum paraoxonase activity in haemodialysis patients: an in vitro study. *Nephrol Dial Transplant.* 2004 January; 19(1):75-82
110. Kastelein J J, Hack C E, Khaw K T. Serum levels of type II secretory phospholipase $A_2$ and the risk of future coronary artery disease in apparently healthy men and women: the EPIC-Norfolk prospective population study. Arterioscler Thromb Vasc Biol 2005; 25:839-846
111. Doi H, Sugiyama S, Yasue H. Circulating levels of secretory type II phospholipase $A_2$ predict coronary events in patients with coronary artery disease. Circulation 1999; 100:1280-1284
112. Liu P Y, Li Y H, Tsai W C, Chao T H, Tsai L M, Wu H L, Chen J H. Prognostic value and the changes of plasma levels of secretory type II phospholipase $A_2$ in patients with coronary artery disease undergoing percutaneous coronary intervention. Eur Heart J 2003; 24:1824-1832
113. Kugiyama K, Ota Y, Sugiyama S, Kawano H, Doi H, Soejima H, Miyamoto S, Ogawa H, Takazoe K, Yasue H. Prognostic value of plasma levels of secretory type II phospholipase $A_2$ in patients with unstable angina pectoris. Am J Cardiol 2000; 86:718-722
114. Porela P, Pulkki K, Voipio-Pulkki L M, Pettersson K, Leppänen V, Nevalainen T J. Circulating phospholipase $A_2$ in prediction of the prognosis of patients with suspected myocardial infarction. Basic Res Cardiol 2000; 95:413-417.
115. Mattsson N, Magnussen C G, Ronnemaa T, Mallat Z, Benessiano J, Jula A, Taittonen L, Käbönen M, Juonala M, Viikari J S, Raitakari O T. Metabolic Syndrome and Carotid Intima-Media Thickness in Young Adults: Roles of Apolipoprotein B, Apolipoprotein A-I, C-Reactive Protein, and Secretory Phospholipase A2: The Cardiovascular Risk in Young Finns Study. *Arterioscler Thromb Vasc Biol.* 2010 September; 30(9):1861-6
116. Partrick D A, Moore E E, Silliman C C, Barnett C C, Kuypers F A. Secretory phospholipase A2 activity correlates with postinjury multiple organ failure. *Crit. Care Med.* 2001 May; 29(5):989-93
117. Lausevic Z, Lausevic M, Trbojevic-Stankovic J, Krstic S, Stojimirovic B. Predicting multiple organ failure in patients with severe trauma. Can J. Surg. 2008 April; 51(2): 97-102
118. Jaross W, Eckey R, Menschikowski M. Biological effects of secretory phospholipase A(2) group IIA on lipoproteins and in atherogenesis. Eur J Clin Invest. 2002 June; 32(6):383-93
119. Rosenson R S, Elliott M, Stasiv Y, Hislop C; *for the PLASMA II Investigators.* Randomized trial of an inhibitor of secretory phospholipase A$_2$ on atherogenic lipoprotein subclasses in statin-treated patients with coronary heart disease. *Eur Heart J.* 2010 Nov. 16. [Epub ahead of print]
120. Greco G, Balogh G, Brunelli R, Costa G, De Spirito M, Lenzi L, Mei G, Ursini F, Parasassi T. Generation in human plasma of misfolded, aggregation-prone electronegative low density lipoprotein. Biophys J. 2009 Jul. 22; 97(2): 628-35
121. Asatryan L, Hamilton R T, Isas J M, Hwang J, Kayed R, Sevanian A. LDL phospholipid hydrolysis produces modified electronegative particles with an unfolded apoB-100 protein. *J Lipid Res.* 2005 January; 46(1):1 15-22
122. Lee E, Nichols P, Spicer D, Groshen S, Yu M C, Lee A S. GRP78 as a novel predictor of responsiveness to chemotherapy in breast cancer. Cancer Res 2006; 66: 7849-53
123. Misra U K, Payne S, Pizzo S V. Ligation of prostate cancer cell surface GRP78 activates a proproliferative and antiapoptotic feedback loop: a role for secreted prostate-specific antigen. *J Biol. Chem.* 2011 Jan. 14; 286(2):1248-59
124. de Ridder G G, Gonzalez-Gronow M, Ray R, Pizzo S V. Autoantibodies against cell surface GRP78 promote tumor growth in a murine model of melanoma. *Melanoma Res.* 2010 Dec. 15. [Epub ahead of print]
125. Hardy B, Raiter A. Peptide-binding heat shock protein GRP78 protects cardiomyocytes from hypoxia-induced apoptosis. *J Mol. Med.* 2010 November; 88(11):1157-67
126. Thuerauf D J, Marcinko M, Gude N, Rubio M, Sussman M A, Glembotski C C. Activation of the unfolded protein response in infarcted mouse heart and hypoxic cultured cardiac myocytes. *Circ Res.* 2006 Aug. 4; 99(3):275-82
127. Davidson D J, Haskell C, Majest S, Kherzai A, Egan D A, Walter K A, Schneider A, Gubbins E F, Solomon L, Chen Z, Lesniewski R, Henkin J. Kringle 5 of human plasminogen induces apoptosis of endothelial and tumor cells through surface-expressed glucose-regulated protein 78. Cancer Res 2005; 65: 4663-72
128. Gebbink M F, Voest E E, Reijerkerk A. Do antiangiogenic protein fragments have amyloid properties? Blood. 2004 Sep. 15; 104(6):1601-5
129. Koch C G, Li L, Sessler D I, Figueroa P, Hoeltge G A, Mihaljevic T, Blackstone E H. *Duration of Red-Cell Storage and Complications after Cardiac Surgery.* N Engl J. Med. 2008 Mar. 20; 358(12):1229-39.
130. Hermeling S, Crommelin D J, Schellekens H, Jiskoot W. Strukture-Immunogenicity relationships of therapeutic proteins. Pharm Res. 2004 June; 21(6):897-903
131. Rosenberg A S. Effects of protein aggregates. An Immunologic Perspective. *AAPS J.* 2006 Aug. 4; 8(3):E501-7
132. Joubert M K, Hokom M, Xie J, Deshpande M, Kaliyaperumal A, Chirmule N, Juan G, Goltz T, Narhi L, Jawa V, An innate immune response was induced from PBMCs following challenge with aggregated biotherapeutics. 2010 Workshop On Protein Aggregation and Immunogenicity, Posterpresentation
133. Gagnon P, Arakawa T. Aggregation detection and removal in biopharmaceutical proteins. Curr Pharm Biotechnol. 2009 June; 10(4):347
134. Wang W. Protein aggregation and its inhibition in biopharmaceutics. Int J. Pharm. 2005 Jan. 31; 289(1-2):1-30
135. Stefani M, Dobson C M. Protein aggregation and aggregate toxicity: new insights into protein folding, misfolding diseases and biological evolution. *J Mol. Med.* 2003 November; 81(11):678-99
136. Cromwell M, Hilario E, Jacobson F. Protein Aggregation and Bioprocessing. AAPS Journal. 2006; 8(3):E572-E579
137. Dische F E, Wernstedt C, Westermark G T, Westermark P, Pepys M B, Rennie J A, Gilbey S G, Watkins P J. Insulin as an amyloid-fibril protein at sites of repeated insulin injections in a diabetic patient. Diabetologia. 1988; 31(3): 158-61
138. Ahmad A, Millett I S, Doniach S, Uversky V N, Fink A L. Partially folded intermediates in insulin fibrillation. Biochemistry. 2003; 42(39):11404-16
139. Philo, J. S. A critical review of methods for size characterization of non-particulate protein aggregates. *Curr Pharm Biotechnol.* 2009 June; 10(4):359-72.
140. Costerton J W, Lewandowski Z, Caldwell D E, Korber D R, Lappin-Scott H M. Microbial biofilms. Annu Rev Microbiol. 1995; 49:711-45
141. Hall-Stoodley L, Costerton J W, Stoodley P. Bacterial Biofilms: from the natural environment to infectious diseases. Nat. Rev. Microbiol. 2004; 2: 95-108
142. Larsen P, Nielsen J L, Dueholm M S, Wetzel R, Otzen D, Nielsen P H. Amyloid adhesins are abundant in natural biofilms. *Environ Microbiol.* 2007 December; 9(12):3077-90.
143. Williams D. Revisiting the definition of biocompatibility. *Med Device Technol.* 2003 October; 14(8):10-3
144. Ratner B D. The catastrophe revisited: Blood compatibility in the 21st Century. *Biomaterials.* 2007 December; 28(34):5144-7
145. Wintermantel E, Ha S-W: Medizintechnik—Life Science Engineering, Springer-Verlag Berlin Heidelberg, 2009
146. Merritt K, Edwards C R, Brown S A. Use of an enzyme linked immunosorbent assay (ELISA) for quantification of proteins on the surface of materials. *J Biomed Mater Res.* 1988 February; 22(2):99-109
147. Cherny I, Gazit E. Amyloide: nicht nur pathologische Substanzen, sondern auch geordnete Nanomaterialien. Angewandte ChemieVolume 120, Issue 22, 2008
148. Reches M, Gazit E. Assembly of Peptide Nanostructures: Mechanism of Association and Potential Uses Current Nanoscience, 2006, 2, 105-111
149. Hamedi M, Herland A, Karlsson R H, Inganäs O. Electrochemical devices made from conducting nanowire networks self-assembled from amyloid fibrils and alkoxysulfonate PEDOT. *Nano Lett.* 2008 June; 8(6):1736-40
150. Scheibel T, Parthasarathy R, Sawicki G, Lin X M, Jaeger H, Lindquist S L. Conducting nanowires built by controlled self-assembly of amyloid fibers and selective metal deposition. *Proc Natl Acad Sci USA.* 2003 Apr. 15; 100(8): 4527-32
151. Gebbink M F, Claessen D, Bouma B, Dijkhuizen L, Wösten H A. Amyloids—a functional coat for microorganisms. *Nat Rev Microbiol.* 2005 April; 3(4):333-41

The invention claimed is:

1. A binding substance selected from proteins or peptides comprising the amino acid sequence HWRR (SEQ ID NO: 9) capable of binding to misfolded proteins or peptides, for treatment of diseases that are linked to misfolded proteins or peptides.

2. A method for binding misfolded proteins or peptides in a sample comprising contacting a sample containing said misfolded proteins or peptides with a binding substance capable of binding to said misfolded proteins or peptides, wherein the binding substance is selected from proteins or peptides comprising the amino acid sequence HWRR (SEQ ID NO: 9).

3. A method according to claim 2, wherein the binding substance is chosen from peptides comprising the amino acid sequence His, Trp, Arg, Arg, Pro (HWRRP) (SEQ ID NO:10), the amino acid sequence Ala, Val, Thr, Leu, Glu, Asn, Phe, Leu, His, Trp, Arg, Arg (SEQ ID NO: 4) corresponding to amino acids 278-289 of the ADAM 15 sequence, the amino acid sequence Glu, Asn, Phe, Leu, His, Trp, Arg, Arg, Ala, His, Leu, Leu (ENFLHWRRAHLL) (SEQ ID NO: 3) corresponding to amino acids 282-293 of the ADAM 15 sequence, the amino acid sequence His, Trp, Arg, Arg, Ala, His, Leu, Leu, Pro, Arg, Leu, Pro (HWRRAHLLPRLP) (SEQ ID NO: 2) corresponding to amino acids 286-297 of the ADAM 15 sequence, the metalloprotease domain of ADAM15 or ADAM15 (Metargidin).

4. A method according to claim 2, wherein the binding substance is immobilised on a solid phase.

5. A method according to claim 4, wherein the solid phase is chosen from a microtiter plate, a chip for surface plasmon resonance analyses, a filter, a membrane, a test stripe, magnetic or fluorophore-labelled beads, a silicon-wafer, glass, metal, plastic, a chip, a matrix or target for mass spectrometry, and beads for flow cytometric analyses.

6. A method according to claim 2, to determine whether a misfolded protein and/or peptide is present in a sample.

7. A method according to claim 6, wherein the determination includes qualitative and/or quantitative analyses.

8. A method according to claim 2, to remove or separate the misfolded proteins or peptides from a sample.

9. A method according to claim 6, wherein the sample is selected from the group consisting of body fluids, tissue extractions, blood, serum, blood plasma, lymph fluid, seminal fluid, vaginal fluid, amniotic liquor, cerebrospinal fluid, synovial fluid, urine, sputum, fluids from lavages, bronchial alveolar lavage, and peritoneal lavage.

10. A method according to claim 6, wherein the sample is selected from the group consisting of medical products, drugs, drug constituents, pharmaceutical compositions, reagents, additive reagents for diagnostic tests, research reagents, food, food supplements, semiluxary food, dietary supplements, drinking water, non drinking water, and biofilms.

11. A method for the analysis of misfolded proteins or peptides in a sample, comprising
    a) contacting one or more of the binding substances according to claim 2 with a sample; and
    b) conducting qualitative and/or quantitative analysis of bound misfolded proteins or peptides resulting from the contacting.

12. A method according to claim 11, wherein the sample is selected from the group consisting of body fluids, tissue extractions, blood, serum, blood plasma, lymph fluid, seminal fluid, vaginal fluid, amniotic liquor, cerebrospinal fluid, synovial fluid, urine, sputum, fluids from lavages, bronchial alveolar lavage, and peritoneal lavage.

13. A method according to claim 11, wherein the analysis of misfolded proteins or peptides includes reaction with a specific detection reagent for the misfolded protein or peptide.

14. A method according to claim 13, wherein the detection reagent includes another binding substance for the bound misfolded proteins or peptide.

15. A method according to claim 14, wherein the other binding substance is chosen from chaperones, scavenger receptors, t-PA, FXII, HGFA, congo red or thioflavin.

16. A method according to claim 13, wherein the detection reagent is chosen from specific antibodies against the proteins or peptides.

17. A method according to claim 13, wherein the detection reagent can be analyzed together with an indicator reagent for protein modifications as built by acrolein and other electrophilic substances, glycations, proteolytic cleavage, phorphorylation, dephosphorylation, glycosylation, acetylation, S-nitrosylation, citrullination or sulfatation.

18. A method according to claim 13, wherein the detection reagent is bound to an indicator label.

19. A method according to claim 18, wherein the indicator label is selected from the group consisting of fluorescence labels, DiI, FITC, PE, PerCp, Cy, Alexa-, Dyomics, fluorescence colours, biotin, a HIS-tag, a GST-tag, a SEAP-tag, a maltose binding protein-tag (MBP-tag), a FLAG-tag, digoxigenin, a paramagnetic atom, a radioactive atom, $C^{11}$, J-125/123, $^{99m}Tc$, $Cu^{64}$, $In^{111}$, reporter enzymes, alkalic phosphatase, horseradish peroxidase, beta-galectosidase, glucose oxidase, luciferase, beta-lactamase, urease and lysozyme.

20. A method according to claim 11, to control the manufacturing process of drugs, pharmaceutical compounds, reagents, additive reagents for diagnostic tests, research reagents, food or biofilms.

21. A method according to claim 11,
    as conducted for control of quality and hygiene in an application selected from the group consisting of research, health care, food production, food storage and trading.

22. A method for the removal of misfolded proteins or peptides from a sample or product, comprising
    a) contacting the sample or product with one or more of the binding substances as defined in claim 2, and
    b) clearing the bound misfolded proteins or peptides from the sample or product.

23. A method according to claim 22, wherein the sample is selected from the group consisting of body fluids, tissue extractions, blood, serum, blood plasma, lymph fluid, seminal fluid, vaginal fluid, amniotic liquor, cerebrospinal fluid, synovial fluid, urine, sputum, fluids from lavages, bronchial alveolar lavage, and peritoneal lavage.

24. A method according to claim 22, wherein the sample or product is selected from the group consisting of medical products, drugs, drug constituents, pharmaceutical compositions, reagents, additive reagents for diagnostic tests, research reagents, food, food supplements, semiluxary food, dietary supplements, drinking water, non drinking water, and biofilms.

25. A method for the preparation of misfolded proteins or peptides from a sample, comprising
    a) contacting the sample with one or more of the binding substances as defined in claim 2,
    b) separation of the bound misfolded proteins or peptides resulting from the contacting, and
    c) isolation of the misfolded proteins or peptides.

26. A method according to claim 25,
    wherein the sample is selected from the group consisting of body fluids, tissue extractions, blood, serum, blood plasma, lymph fluid, seminal fluid, vaginal fluid, amniotic liquor, cerebrospinal fluid, synovial fluid, urine, sputum, fluids from lavages, bronchial alveolar lavage, and peritoneal lavage.

27. A method for use in diagnosis, stratification and/or monitoring of diseases, which are affected by misfolded proteins or peptides, comprising the following steps
    a) provision of a sample,
    b) qualitative and/or quantitative analysis of misfolded proteins or peptides in this sample using a method comprising contacting one or more of the binding substances according to claim 2 with the sample; and conducting qualitative and/or quantitative analysis of bound misfolded proteins or peptides resulting from the contacting, and
    c) comparison of the results of the analysis in step b) with one or more defined reference samples.

28. A method according to claim 27,
    wherein the disease is chosen from diseases that are linked to the formation of amyloid-like proteins, like the group of the classical amyloidoses and neurodegenerative diseases, diabetes, metabolic syndrome, obesity, arteriosclerosis and its effected diseases, bleeding, thrombosis, DIC, renal failure, cataract, multiple myeloma, lymphoma, sepsis, severe tissue injury, condition after use of heart-lung-machine or organ transplantation, condition after implantation of heart assist devices, pancreatitis, condition after reanimation, ischemia reperfusion injury, and preeclampsia.

29. A method according to claim 27,
for monitoring, checking, and/or control of drug therapy.

30. A method according to claim 29,
wherein the drug therapy includes a treatment with ASS/Aspirin, thienopyridines as clopidogrel, prasugrel or ticlopidine, PEGylated liposomes and/or phospholipase A2 inhibitors.

31. A method for the analysis of the biocompatibility of a material, comprising:
  a) contacting the material with a test substance, that includes proteins or peptides,
  b) conducting qualitative or quantitative analysis of misfolded proteins or peptides in the test substance, using a method comprising contacting one or more of the binding substances according to claim 2 with the test substance; and conducting qualitative and/or quantitative analysis of bound misfolded proteins or peptides resulting from the contacting, and
  c) comparing misfolded proteins or peptides in the test substance before and after exposure to the material.

32. A method for the enrichment of microorganisms that carry misfolded proteins on their surface from a sample, including the steps
  a) contacting the sample with one or more binding substances as defined in claim 2, and
  b) preparation of the bound microorganisms from the sample.

33. A method according to claim 2, wherein the binding substance is chosen from peptides consisting of the amino acid sequence His, Trp, Arg, Arg, Pro (HWRRP) (SEQ ID NO:10), the amino acid sequence Ala, Val, Thr, Leu, Glu, Asn, Phe, Leu, His, Trp, Arg, Arg (SEQ ID NO: 4) corresponding to amino acids 278-289 of the ADAM 15 sequence, the amino acid sequence Glu, Asn, Phe, Leu, His, Trp, Arg, Arg, Ala, His, Leu, Leu (ENFLHWRRAHLL) (SEQ ID NO: 3) corresponding to amino acids 282-293 of the ADAM 15 sequence, the amino acid sequence His, Trp, Arg, Arg, Ala, His, Leu, Leu, Pro, Arg, Leu, Pro (HWRRAHLLPRLP) (SEQ ID NO: 2) corresponding to amino acids 286-297 of the ADAM 15 sequence, the metalloprotease domain of ADAM15 or ADAM15 (Metargidin).

34. A method of treating disease linked to misfolded proteins or peptides in a subject comprising depleting or removing misfolded proteins or peptides from a body fluid of the subject by contacting the body fluid with a binding substance capable of binding to said misfolded proteins or peptides, wherein the binding substance is selected from proteins or peptides comprising the amino acid sequence HWRR (SEQ ID NO: 9).

35. The method according to claim 34, wherein the disease is selected from the group consisting of Alzheimer's disease, prion diseases, Creutzfeldt-Jakob disease, Gerstmann-Sträussler-Scheinker-syndrome, fatal familial insomnia, Kuru, bovine spongiforme encephalopathy, scrappy, neurodegenerative diseases, Parkinson disease, Amyotrophic lateral sclerosis (ALS), familial encephalopathy with neuroserpin inclusion bodies, frontotemporal lobar degeneration with ubiquitin proteasome system (FTLD-UPS), auto immune disorders, rheumatic arthritis, inflammatory diseases, multiple sclerosis, arteriosclerosis, infections, infections by microorganisms which present misfolded proteins on their surface, sepsis, diabetes, wound healing problems, preeclampsia, bleeding tendency, thrombosis, condition after reanimation, condition after hemodialysis, cancers, amyloidoses, AA-amyloidoses, AL-amyloidoses, AE-amyloidoses, AB-amyloidoses, AP-amyloidoses, AS-amyloidoses, ATTR-amyloidoses, and cataract.

36. A diagnostic kit for the analysis of misfolded proteins or peptides, comprising
  a) the first binding substance as defined in claim 2, and
  b) a specific detection reagent for the misfolded protein or peptide, wherein the detection reagent is another binding substance as defined in claim 1 or a specific antibody against the protein or peptide, wherein one of the components a) and b) carries a detectable label and the other component a) and b) is immobilized to a solid phase.

* * * * *